(12) United States Patent
Hur et al.

(10) Patent No.: US 12,289,987 B2
(45) Date of Patent: Apr. 29, 2025

(54) ORGANIC LIGHT-EMITTING DEVICE AND APPARATUS INCLUDING THE SAME

(71) Applicant: Samsung Display Co., Ltd., Yongin-si (KR)

(72) Inventors: Jaeweon Hur, Yongin-si (KR); Kyungsik Kim, Yongin-si (KR); Sungwook Kim, Yongin-si (KR); Seulong Kim, Yongin-si (KR); Seungjin Chu, Yongin-si (KR); Hyein Jeong, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 772 days.

(21) Appl. No.: 16/935,004

(22) Filed: Jul. 21, 2020

(65) Prior Publication Data

US 2021/0202844 A1    Jul. 1, 2021

(30) Foreign Application Priority Data

Dec. 27, 2019    (KR) .................. 10-2019-0176264

(51) Int. Cl.
*H10K 85/60* (2023.01)
*C07D 209/88* (2006.01)
(Continued)

(52) U.S. Cl.
CPC ......... *H10K 85/633* (2023.02); *C07D 209/88* (2013.01); *C07F 7/0812* (2013.01); *H10K 85/40* (2023.02); *H10K 85/636* (2023.02); *H10K 50/15* (2023.02); *H10K 50/17* (2023.02); *H10K 50/18* (2023.02); *H10K 85/624* (2023.02);
(Continued)

(58) Field of Classification Search
None
See application file for complete search history.

(56) References Cited

U.S. PATENT DOCUMENTS 8,148,891 B2    4/2012  Tung et al.
8,927,980 B2    1/2015  Kashiwabara
(Continued)

FOREIGN PATENT DOCUMENTS

KR    10-2002-0055418 A    7/2002
KR    10-2013-0070201 A    6/2013
(Continued)

OTHER PUBLICATIONS

Philip K. Koech et al. "Design of new anchored p-dopants for high power efficiency OLEDs", Proc. of SPIE, vol. 7415, p. 741505 (Year: 2009).*
(Continued)

*Primary Examiner* — Seokmin Jeon
(74) *Attorney, Agent, or Firm* — Lewis Roca Rothgerber Christie LLP

(57) ABSTRACT

An organic light-emitting device in which a hole transport region includes a first hole transport stack, a second hole transport stack between the first hole transport stack and an emission layer, and an electron blocking layer between the second hole transport stack and the emission layer, wherein a HOMO energy level of the hole transport region satisfies a certain equations. The organic light-emitting devices according to embodiments of the present disclosure may have high efficiency and a long lifespan.

18 Claims, 1 Drawing Sheet

(51) Int. Cl.
    *C07F 7/08*     (2006.01)
    *H10K 50/15*     (2023.01)
    *H10K 50/17*     (2023.01)
    *H10K 50/18*     (2023.01)
    *H10K 85/40*     (2023.01)
    *H10K 101/30*     (2023.01)
    *H10K 101/40*     (2023.01)

(52) U.S. Cl.
    CPC ....... *H10K 85/626* (2023.02); *H10K 85/6572* (2023.02); *H10K 2101/30* (2023.02); *H10K 2101/40* (2023.02)

(56) References Cited

U.S. PATENT DOCUMENTS

| | | | |
|---|---|---|---|
| 10,297,777 | B2 | 5/2019 | Kim et al. |
| 2002/0121860 | A1* | 9/2002 | Seo ................ 313/506 |
| 2010/0001636 | A1* | 1/2010 | Yabunouchi ................ 313/504 |
| 2013/0153865 | A1 | 6/2013 | Kho et al. |
| 2014/0316134 | A1* | 10/2014 | Stoessel ............ H01L 51/0054 |
| 2015/0255723 | A1* | 9/2015 | Kim ................ H01L 51/0032 |
| 2015/0255741 | A1 | 9/2015 | Lee et al. |
| 2015/0270502 | A1* | 9/2015 | Fuchiwaki .......... H01L 51/0094 |
| 2015/0270506 | A1* | 9/2015 | Voges ................ H01L 51/5064 |
| 2016/0225993 | A1* | 8/2016 | Huh ...................... H01L 51/006 |
| 2016/0254459 | A1 | 9/2016 | Kawamura et al. |
| 2017/0062734 | A1 | 3/2017 | Suzuki et al. |
| 2017/0092887 | A1 | 3/2017 | Lee et al. |
| 2018/0358562 | A1 | 12/2018 | Takita et al. |
| 2019/0088896 | A1 | 3/2019 | Kim et al. |
| 2019/0115541 | A1* | 4/2019 | Xia .................... H01L 51/0055 |
| 2021/0367177 | A1* | 11/2021 | Seo .................... H01L 51/5004 |

FOREIGN PATENT DOCUMENTS

| | | |
|---|---|---|
| KR | 10-2014-0038296 A | 3/2014 |
| KR | 10-1482829 B1 | 1/2015 |
| KR | 10-2015-0105520 A | 9/2015 |
| KR | 10-2016-0035561 A | 3/2016 |
| KR | 10-2017-0038322 A | 4/2017 |
| KR | 10-2018-0017901 A | 2/2018 |
| KR | 10-2018-0044985 A | 5/2018 |
| KR | 10-2018-0095872 A | 8/2018 |
| KR | 10-2019-0033117 A | 3/2019 |
| KR | 10-2019-0090893 A | 8/2019 |

OTHER PUBLICATIONS

Huiqing Pang et al. "A full-color, low-power, wearable display for mobile applications", SPIE, Mar. 29, 2012 (Year: 2012).*
Jin-hong Liu et al. "Effect of Al:Ag alloy cathode on the performance of transparent organic light-emitting devices", Optoelectron. Lett. 2017, vol. 13, p. 175-178 (Year: 2017).*
English translation of JP 2015/13362 A and the original JP 2015/13362 A, Ichiro Imada (Year: 2015).*
Lee, Whonho, et al., "Improvement of charge balance, recombination zone confinement, and low efficiency roll-off in green phosphorescent OLEDs by altering electron transport layer thickness," Materials Research Express, vol. 5, No. 7, (2018), https://doi.org/10.1088/2053-1591/aacec6, 22 pages.

* cited by examiner

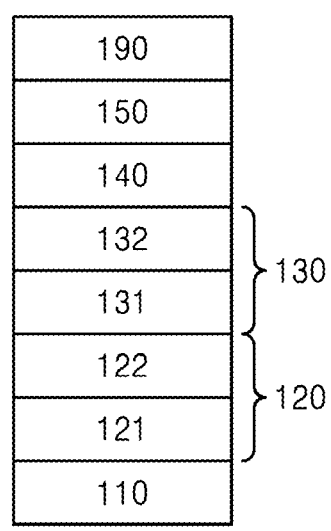

ORGANIC LIGHT-EMITTING DEVICE AND APPARATUS INCLUDING THE SAME

CROSS-REFERENCE TO RELATED APPLICATION

This application claims priority to and the benefit of Korean Patent Application No. 10-2019-0176264, filed on Dec. 27, 2019, in the Korean Intellectual Property Office, the entire content of which is incorporated herein by reference.

BACKGROUND

1. Field

One or more aspects of embodiments of the present disclosure relate to an organic light-emitting device and an apparatus including the same.

2. Description of Related Art

Organic light-emitting devices are self-emission devices that produce full-color images, and also have wide viewing angles, high contrast ratios, short response times, and excellent characteristics in terms of brightness, driving voltage, and/or response speed, compared to devices in the art.

The organic light-emitting device may include a first electrode on a substrate, and a hole transport region, an emission layer, an electron transport region, and a second electrode, which are sequentially on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state, thereby generating light.

SUMMARY

One or more aspects of embodiments of the present disclosure are directed toward an organic light-emitting device with a prolonged lifespan.

Additional aspects will be set forth in part in the description which follows and, in part, will be apparent from the description, or may be learned by practice of the presented embodiments of the disclosure.

An embodiment of the present disclosure provides an organic light-emitting device including a first electrode,
a second electrode facing the first electrode, and
an organic layer between the first electrode and the second electrode, the organic layer including an emission layer and a hole transport region between the first electrode and the emission layer,
wherein the hole transport region includes a first hole transport stack, a second hole transport stack between the first hole transport stack and the emission layer, and an electron blocking layer between the second hole transport stack and the emission layer,
the first hole transport stack includes a first hole injection layer and a first hole transport layer,
the second hole transport stack includes a second hole injection layer and a second hole transport layer,
the first hole injection layer is between the first electrode and the first hole transport layer,
the second hole injection layer is between the first hole transport layer and the second hole transport layer,
the first hole injection layer may include a first compound,
the first hole transport layer may include a second compound,
the second hole injection layer may include a third compound,
the second hole transport layer may include a fourth compound,
the electron blocking layer may include a fifth compound, and
the organic light-emitting device satisfies Equations 1 to 4:

$$HOMO(HTM1) \geq HOMO(HTM2) \quad \text{Equation 1}$$

$$HOMO(HTM3) \geq HOMO(HTM4) \quad \text{Equation 2}$$

$$HOMO(HTM1) - HOMO(HTM2) \leq 0.5 \text{ eV} \quad \text{Equation 3}$$

$$HOMO(HTM3) - HOMO(HTM4) \leq 0.5 \text{ eV}. \quad \text{Equation 4}$$

The HOMO(HTM1) is a lower energy level from among the HOMO energy level (eV) of the first compound and the HOMO energy level (eV) of the second compound,
the HOMO(HTM2) is a higher energy level from among the HOMO energy level (eV) of the third compound and the HOMO energy level (eV) of the fourth compound,
the HOMO(HTM3) is a lower energy level from among the HOMO energy level (eV) of the third compound and the HOMO energy level (eV) of the fourth compound,
the HOMO(HTM4) is the HOMO energy level (eV) of the fifth compound,
HOMO(HTM1), HOMO(HTM2), HOMO(HTM3), and HOMO(HTM4) are measured by photoelectron spectrometer.

In one embodiment, the first hole transport layer may be at an interface between the first hole injection layer and the second hole injection layer.

In one embodiment, the second hole injection layer may be at an interface between the first hole transport layer and the second hole transport layer.

In one embodiment, the electron blocking layer may be at an interface between the second hole transport layer and the emission layer.

In one embodiment, the first compound and the second compound are different from each other, the third compound and the fourth compound are different from each other, the first hole injection layer may consist of the first compound, and the second hole injection layer may consist of the third compound.

In one embodiment, the first compound and the second compound may be different from each other, the third compound and the fourth compound may be different from each other, HOMO(C1) may be greater than or equal to HOMO(C2), and HOMO(C3) may be greater than or equal to HOMO(C4), wherein HOMO(C1), HOMO(C2), HOMO(C3) and HOMO(C4) indicate the HOMO energy levels (eV) of the first compound, second compound, third compound and fourth compound, respectively.

In one embodiment, the first hole injection layer and the second hole injection layer may each further include a p-dopant. The p-dopant may be a charge-generating material having a lowest unoccupied molecular orbital (LUMO) energy level of less than −3.5 eV.

In one embodiment, each of the first hole injection layer and the second hole injection layer may further include a p-dopant, the first compound and the second compound are identical to each other, and the third compound and the fourth compound are identical to each other.

In one embodiment, the thickness of the first hole injection layer and the thickness of the second hole injection layer may each independently be in a range from about 10 Å to about 500 Å.

In one embodiment, the thickness of the first hole transport layer and the thickness of the second hole transport layer may each independently be in a range from about 100 Å to about 1500 Å.

In one embodiment, the first compound and the third compound may each independently be selected from compounds represented by Formulae 1-1 to 1-4 and Formula 2.

$$A_1 \!\!-\!\!\left[(L_1)_{a1}\!-\!(Ar_1)_{b1}\right]_{n1} \quad \text{Formula 1-1}$$

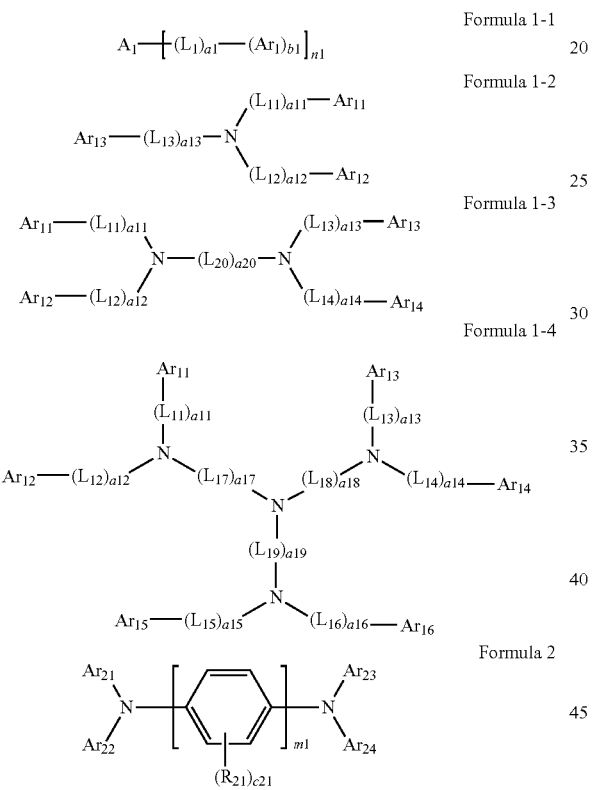

Formula 2 wherein, in Formulae 1-1 to 1-4, $A_1$ may be a $C_5$-$C_{60}$ carbocyclic group or a $C_1$-$C_{60}$ heterocyclic group, each independently unsubstituted or substituted with at least one $R_1$, $L_1$ and $L_{11}$ to $L_{19}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{20}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 and a11 to a19 may each independently be an integer from 0 to 3, a20 may be an integer from 1 to 10, $Ar_1$, $Ar_{11}$ to $Ar_{16}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 may be an integer from 1 to 5, n1 may be an integer from 0 to 5, wherein, in Formula 2, m1 may be an integer from 1 to 5, $Ar_{21}$ to $Ar_{24}$ may each independently be selected from a group represented by Formula 2A, a group represented by Formula 2B, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one of $Ar_{21}$ to $Ar_{24}$ is selected from groups represented by Formulae 2A and 2B,

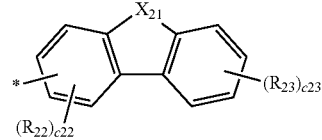

Formula 2A

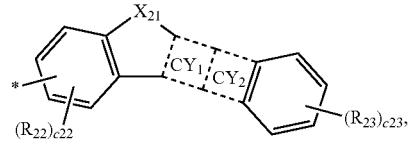

Formula 2B wherein, in Formulae 2A and 2B, $X_{21}$ may be selected from $C(R_{24})(R_{25})$, $Si(R_{24})(R_{25})$, $N(R_{24})$, O, and S, $CY_1$ ring may be a condensed benzene ring that is substituted with at least one $R_a$, CY$_1$ ring may be condensed with a neighboring X$_{21}$-containing 5-membered ring and a neighboring CY$_2$ ring (e.g., X$_{22}$-containing 5-membered ring), CY$_2$ ring may be a 5-membered ring represented by

X$_{22}$ may be selected from C(R$_{26}$)(R$_{27}$), Si(R$_{26}$)(R$_{27}$), N(R$_{26}$), O, and S, wherein, in Formulae 1-1 to 1-4, 2, 2A and 2B, R$_1$, R$_a$, and R$_{21}$ to R$_{27}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_1$)(Q$_2$), —B(Q$_1$)(Q$_2$), —C(=O)(Q$_1$), —S(=O)$_2$(Q$_1$), and —P(=O)(Q$_1$)(Q$_2$), c21 and c23 may each independently be an integer from 1 to 4, c22 may be an integer from 1 to 3, and Q$_1$ to Q$_3$ may each independently be selected from hydrogen, deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group.

In one embodiment, the second compound and the fourth compound may each independently be selected from compounds represented by Formulae 1-1 to 1-3.

In one embodiment, the fifth compound may be a compound represented by Formula 5.

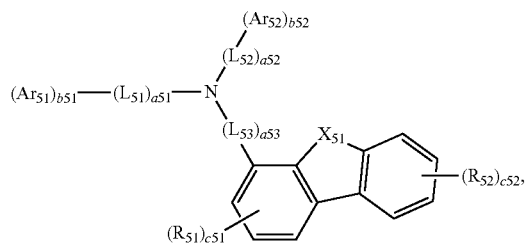

Formula 5 wherein, in Formula 5,

X$_{51}$ may be O or S,

L$_{51}$ to L$_{53}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, a51 to a53 may each independently be an integer from 0 to 3, Ar$_{51}$ and Ar$_{52}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, and —Si(Q$_1$)(Q$_2$)(Q$_3$), b51 and b52 may each independently be an integer from 1 to 5, R$_{51}$ and R$_{52}$ may each independently be selected from hydrogen, deuterium, —F, —Cl, —Br, —I, a hydroxyl group, a cyano group, a nitro group, an amidino group, a hydrazine group, a hydrazone group, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_1$)(Q$_2$), —B(Q$_1$)(Q$_2$), —C(=O)(Q$_1$), —S(=O)$_2$(Q$_1$), and —P(=O)(Q$_1$)(Q$_2$), c51 may be an integer from 1 to 3, and c52 may be an integer from 1 to 4.

In one embodiment, the organic layer may further include an electron transport region between the emission layer and the second electrode, and the electron transport region may include at least one selected from an electron injection layer, an electron transport layer, a hole blocking layer, and a buffer layer.

In one embodiment, the electron transport region may include a hole blocking layer.

In one embodiment, the electron transport region may include an electron transport layer and a hole blocking layer, and the hole blocking layer may be at the interface between the emission layer and the electron transport layer.

In one embodiment, the emission layer may include a host and a dopant, and an amount of the host of the emission layer may be greater than an amount of the dopant of the emission layer.

For example, the dopant may include at least one selected from a fluorescent dopant, a phosphorescent dopant, and a delayed fluorescent dopant.

Another embodiment of the present disclosure provides an apparatus including a thin-film transistor including a source electrode, a drain electrode, and an activation layer, and the organic light-emitting device, wherein the first electrode of the organic light-emitting device is electrically connected with one of the source electrode or the drain electrode of the thin-film transistor.

BRIEF DESCRIPTION OF THE DRAWING

The above and other aspects, features, and advantages of certain embodiments of the disclosure will be more apparent from the following description taken in conjunction with the drawing, which is a schematic view of an organic light-emitting device according to an embodiment.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof. Expressions such as "one of," "at least one selected from," and "selected from," when preceding a list of elements, modify the entire list of elements and do not modify the individual elements of the list. Further, the use of "may" when describing embodiments of the present disclosure refers to "one or more embodiments of the present disclosure."

Hereinafter, embodiments of the present disclosure will be described in more detail with reference to the accompanying drawings. The same or corresponding components will be denoted by the same reference numerals, and thus redundant description thereof will be omitted.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "on" or "onto" another layer, region, or component, it may be directly formed on the other layer, region, or component (without any intervening layers, regions, or components present) or indirectly formed on the other layer, region, or component (that is, for example, intervening layers, regions, or components may be present).

Sizes of elements in the drawings may be exaggerated for convenience of explanation. In other words, since sizes and thicknesses of components in the drawings are arbitrarily illustrated for convenience of explanation, the following embodiments of the present disclosure are not limited thereto.

The term "an organic layer" as used herein refers to a single layer and/or a plurality of layers between the first electrode and the second electrode of an organic light-emitting device. A material included in the "organic layer" is not limited to an organic material.

The expression "(an organic layer) includes a compound represented by Formula 1" as used herein may include a case in which (an organic layer) includes one compound of Formula 1 or two or more different compounds of Formula 1.

Hereinafter, embodiments of the present disclosure will be described in more detail with reference to the attached drawing.

DESCRIPTION OF THE DRAWING

The drawing is a schematic view of an organic light-emitting device 10 according to an embodiment. The organic light-emitting device 10 may include: a first electrode 110; a second electrode 190 facing the first electrode 110; and an organic layer between the first electrode 110 and the second electrode 190, the organic layer including an emission layer 150 and a hole transport region between the first electrode 110 and the emission layer 150, wherein the hole transport region may include a first hole transport stack 120, a second hole transport stack 130 between the first hole transport stack 120 and the emission layer 150, and an electron blocking layer 140 between the second hole transport stack 130 and the emission layer 150, The first hole transport stack 120 may include a first hole injection layer 121 and a first hole transport layer 122, the second hole transport stack 130 may include a second hole injection layer 131 and a second hole transport layer 132, the first hole injection layer 121 may be between the first electrode 110 and the first hole transport layer 122, the second hole injection layer 131 may be between the first hole transport layer 122 and the second hole transport layer 132, the first hole injection layer 121 may include a first compound, the first hole transport layer 122 may include a second compound, The second hole injection layer 131 may include a third compound, the second hole transport layer 132 may include a fourth compound, the electron blocking layer 140 may include a fifth compound, and Equations 1 to 4 are satisfied:

$$HOMO(HTM1) \geq HOMO(HTM2) \quad \text{Equation 1}$$

$$HOMO(HTM3) \geq HOMO(HTM4) \quad \text{Equation 2}$$

$$HOMO(HTM1) - HOMO(HTM2) \leq 0.5 \text{ eV} \quad \text{Equation 3}$$

$$HOMO(HTM3) - HOMO(HTM4) \leq 0.5 \text{ eV}. \quad \text{Equation 4}$$

In Equations 1 to 4, the HOMO(HTM1) is a lower energy level from among the HOMO energy level (eV) of the first compound and the HOMO energy level (eV) of the second compound, the HOMO(HTM2) is a higher energy level from among the HOMO energy level (eV) of the third compound and the HOMO energy level (eV) of the fourth compound, the HOMO(HTM3) is a lower energy level from among the HOMO energy level (eV) of the third compound and the HOMO energy level (eV) of the fourth compound, the HOMO(HTM4) is the HOMO energy level (eV) of the fifth compound, HOMO(HTM1), HOMO(HTM2), HOMO(HTM3), and HOMO(HTM4) are measured by photoelectron spectrometer AC-2 (Riken Keiki Co. Ltd.).

In one embodiment, HOMO(HTM1) may be the HOMO energy level (eV) of the second compound, and HOMO(HTM2) may be the HOMO energy level of the third compound. In one embodiment, when the first compound and the second compound are identical to each other, HOMO(HTM1) may be the HOMO energy level (eV) of the first compound and the second compound. In one embodiment, when the third compound and the fourth compound are identical to each other, and HOMO(HTM2) may be the HOMO energy level of the third compound and the fourth compound.

In one embodiment, the HOMO(HTM3) may be the HOMO energy level (eV) of the fourth compound. In one embodiment, when the third compound and the fourth compound are identical to each other, and HOMO(HTM3) may be the HOMO energy level of the third compound and the fourth compound.

Because the organic light-emitting device 10 includes the first hole transport stack 120 and the second hole transport stack 130 between the first electrode 110 and the electron blocking layer 140, the organic light-emitting device 10 may have a cascade structure in which HOMO energy levels are decreased in a stepwise manner from the first electrode 110 in the order of the first hole transport stack 120, the second hole transport stack 130, and the electron blocking layer 140, and thus, holes may be smoothly provided to the emission layer 150. As a result, the excitons accumulated in the light-emitting zone formed at the interface between the electron blocking layer 140 and the emission layer 150 may be diffused to adjust the concentration of excitons accumulated at the interface. Accordingly, as the excitons diffuse into the emission layer 150 (e.g., into the side of the emission layer) located toward the second electrode 190, the concentration of excitons at the interface between the electron blocking layer 140 and the emission layer 150 decreases, and exciton quenching at the interface between the electron blocking layer 140 and the emission layer 150 may be reduced.

In addition, the light-emitting zone, which is concentrated at the interface between the electron blocking layer 140 and the emission layer 150, may be extended toward the second electrode 190 to emit light in a wider region, thereby improving emission efficiency.

Because the organic light-emitting device 10 simultaneously (or concurrently) satisfies Equations 1 and 2, the organic light-emitting device 10 may have a cascade structure in which HOMO energy levels are decreased in a stepwise manner from the first electrode 110 in the order of the first hole transport stack 120, the second hole transport stack 130, and the electron blocking layer 140, and thus, holes can be smoothly injected into the emission layer 150. As a result, the concentration of excitons may be controlled at the interface between the electron blocking layer 140 and the emission layer 150. Accordingly, emission efficiency and lifespan improvement effects as described above may be obtained.

The minimum value of the HOMO energy gap between the first hole transport stack 120 and the second hole transport stack 130 may be 0.5 eV or less, and the minimum value of the HOMO energy gap between the second hole transport stack 130 and the electron blocking layer 140 may be 0.5 eV or less. When the organic light-emitting device 10 satisfies Equations 3 and 4, the hole injection barrier resulting from the difference in HOMO energy levels of the respective layers forming the hole transport region may be off-set. Accordingly, compared to a comparable organic light-emitting device that does not satisfy Equations 3 and 4, in the organic light-emitting device of the present embodiments, holes injected through the first electrode may not accumulate at the interfaces of the respective organic layers and may be smoothly injected into an emission layer. Thus, the organic light-emitting device may have high efficiency and a long lifespan.

In one embodiment, the first hole transport layer 122 may be positioned at the interface between the first hole injection layer 121 and the second hole injection layer 131.

In one embodiment, the second hole injection layer 131 may be positioned at the interface between the first hole transport layer 122 and the second hole transport layer 132.

When the organic light-emitting device 10 includes the electron blocking layer 140, the injection of electrons from the electron transport region may be prevented or reduced, and thus degradation of a hole transport material in a hole transport region may be prevented or reduced.

In one embodiment, the electron blocking layer 140 may directly contact the emission layer 150. For example, the electron blocking layer 140 may be positioned at the interface between the second hole transport layer 132 and the emission layer 150. When the electron blocking layer 140 directly contact the emission layer 150, excitons may be substantially confined in the emission layer 150, so that the excitons can sufficiently (or suitably) participate in emission.

In one embodiment, the first compound and the second compound are different from each other, the third compound and the fourth compound are different from each other, the first hole injection layer 121 may consist of the first compound, and the second hole injection layer 131 may consist of the third compound. According to the embodiment described above, the first hole injection layer 121 and the second hole injection layer 131 may each include a single material (e.g., a single kind of material).

In one embodiment, the first compound and the second compound may be different from each other, the third compound and the fourth compound may be different from each other, and the conditions of $HOMO(C1) \geq HOMO(C2)$ and $HOMO(C3) \geq HOMO(C4)$ may be satisfied. HOMO(C1), HOMO(C2), HOMO(C3) and HOMO(C4) are the HOMO energy levels (eV) of the first compound, second compound, third compound and fourth compound, respectively, and are measurements obtained by photoelectron spectrometer AC-2 (Riken Keiki Co. Ltd.).

According to the above example, in Formula 1, HOMO (HTM1) may be the same as HOMO(C2), and HOMO (HTM2) may be the same as HOMO(C3).

As described above, when the hole transport region of the organic light-emitting device 10 has a cascade structure in which HOMO energy levels are decreased in a stepwise manner in the order of the first hole injection layer 121, the first hole transport layer 122, the second hole injection layer 131, the second hole transport layer 132, and the electron blocking layer 140, the hole injection barrier into an emission layer is lowered, and thus, the injection of holes into the emission layer 150 may be efficiently (or suitably) achieved.

In one embodiment, each of the first hole injection layer 121 and the second hole injection layer 131 may further include a p-dopant. The amount of the first compound of the first hole injection layer 121 may be greater than the amount of the p-dopant included in the first hole injection layer 121, and the amount of the third compound of the second hole injection layer 122 may be greater than the amount of the p-dopant included in the second hole injection layer 122.

According to some embodiments, the first compound and the second compound may be identical to each other, and the third compound and the fourth compound may be identical to each other. Thus, the first hole injection layer 121 and the second hole injection layer 131 may each be a p-doping layer which includes a p-dopant, in addition to the hole transport material included in a corresponding one of the first hole transport layer 122 and the second hole transport layer 132. As such, an organic light-emitting device including two hole transport stacks (for example, the first and second hole transport stacks 120 and 130) and a hole transport region including the first and second hole injection layers 121 and 131, which are p-doped, may induce high charge movement and conductivity characteristics due to p-doping, and thus, holes injected through the first electrode 110 may not accumulate at the interface between organic layers and may be smoothly injected to an emission layer. Therefore, the emission efficiency and lifespan of the organic light-emitting device 10 may be improved.

The p-dopant will be described in more detail herein below. For example, the p-dopant may be a charge-generating material of which LUMO energy level is lower than −3.5 eV.

In one embodiment, the thickness of the first hole injection layer 121 and the thickness of the second hole injection layer 131 may each independently be from about 10 Å to about 500 Å, and the thickness of the first hole transport layer 122 and the thickness of the second hole transport layer 132 may each independently be from about 100 Å to about 1500 Å. When any of the above ranges are satisfied, the desired life improvement effect can be obtained without a substantial increase in driving voltage of an organic light-emitting device.

The first compound to the fifth compound may not be particularly limited, as long as they are materials that can collectively satisfy Equations 1 to 4. For example, a suitable hole transport material that can be included in a hole transport region, may be used as any of the first compound to the fifth compound.

In one embodiment, the first compound and the third compound may each independently be selected from compounds represented by Formulae 1-1 to 1-4 and Formula 2.

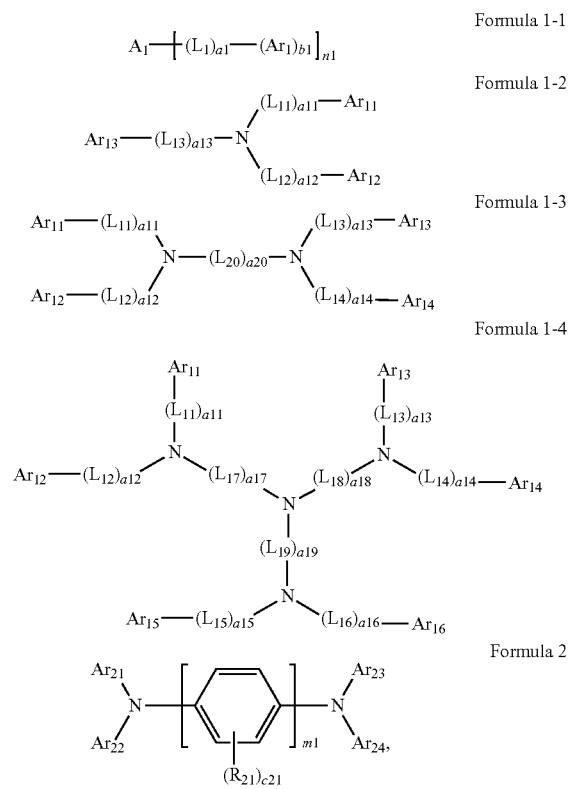

wherein, in Formulae 1-1 to 1-4, $A_1$ may be a $C_5$-$C_{60}$ carbocyclic group or a $C_1$-$C_{60}$ heterocyclic group, each independently unsubstituted or substituted with at least one $R_1$, $L_1$ and $L_{11}$ to $L_{19}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{20}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 and a11 to a19 may each independently be an integer from 0 to 3, a20 may be an integer from 1 to 10, $Ar_1$, $Ar_{11}$ to $Ar_{16}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 may be an integer from 1 to 5, and
n1 may be an integer from 0 to 5,
wherein, in Formula 2,
m1 may be an integer from 1 to 5,
$Ar_{21}$ to $Ar_{24}$ may each independently be selected from a group represented by Formula 2A, a group represented by Formula 2B, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group,
at least one of $Ar_{21}$ to $Ar_{24}$ is selected from groups represented by Formulae 2A and 2B, Formula 2A

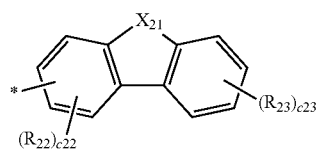

Formula 2B

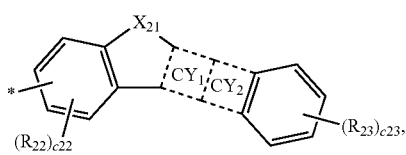

wherein, in Formulae 2A and 2B,
$X_{21}$ may be selected from $C(R_{24})(R_{25})$, $Si(R_{24})(R_{25})$, $N(R_{24})$, O, and S,
$CY_1$ ring may be a condensed benzene ring that is substituted with at least one $R_a$,
$CY_1$ ring may be condensed with a neighboring $X_{21}$-containing 5-membered ring and a neighboring $CY_2$ ring (e.g., $X_{22}$-containing 5-membered ring),
$CY_2$ ring may be a 5-membered ring represented by

$X_{22}$ may be selected from $C(R_{26})(R_{27})$, $Si(R_{26})(R_{27})$, $N(R_{26})$, O, and S,
wherein, in Formulae 1-1 to 1-4, 2, 2A and 2B,
$R_1$, $R_a$, and $R_{21}$ to $R_{27}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$,
c21 and c23 may each independently be an integer from 1 to 4, and
c22 may be an integer from 1 to 3.

In one embodiment, $A_1$ in Formula 1-1 may be selected from a carbazole group, a benzocarbazole group, a dibenzocarbazole group, an indole group, a benzoindole group, a furan group, a benzofuran group, a dibenzofuran group, a thiophene group, a benzothiophene group, a dibenzothiophene group, a 9,9-dihydroxyacridine group, a phenoxazine group, and a phenoxazine group, each independently unsubstituted or substituted with at least one $R_1$.

For example, $A_1$ in Formula 1-1 may be selected from groups represented by Formulae A1-1 to A1-3:

A1-1

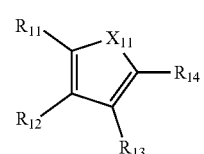

A1-2

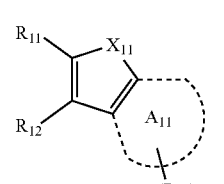

A1-3

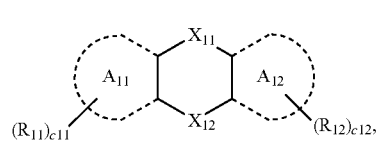

wherein, in Formulae A1-1 to A1-3,
$X_{11}$ may be selected from O, S, and $N(R_{15})$,
$X_{12}$ may be selected from a single bond, O, S, and $N(R_{16})$,
$A_{11}$ and $A_{12}$ may each independently be selected from a $C_5$-$C_{60}$ carbocyclic group and a $C_1$-$C_{60}$ heterocyclic group,
$R_{11}$ to $R_{16}$ may each independently be selected from a binding site to a group represented by *-$(L_1)_{a1}$-$(Ar_1)_{b1}$, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), c11 to c13 may each independently be an integer from 1 to 6, when c11 is 2 or more, two or more $R_{11}$(s) may be identical to or different from each other, when c12 is 2 or more, two or more $R_{12}$(s) may be identical to or different from each other, and when c13 is 2 or more, two or more $R_{13}$(s) may be identical to or different from each other.

In one embodiment, at least one of $Ar_{21}$ to $Ar_{24}$ in Formula 2 may be selected from groups represented by Formulae 2A and 2B-1 to 2B-6:

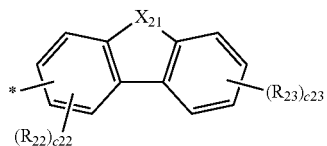

2A

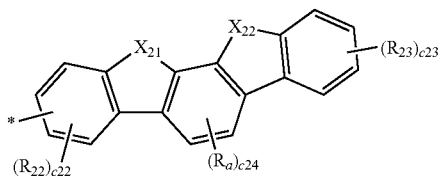

2B-1

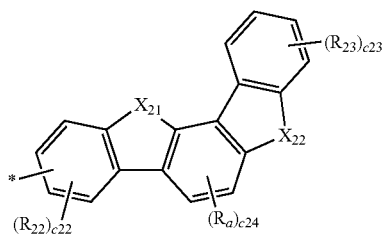

2B-2

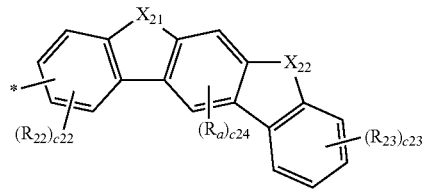

2B-3

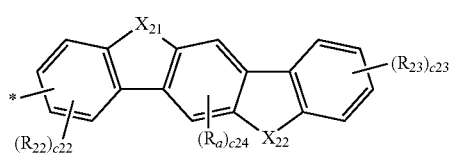

2B-4

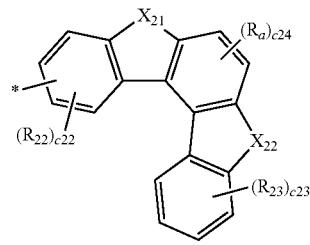

2B-5

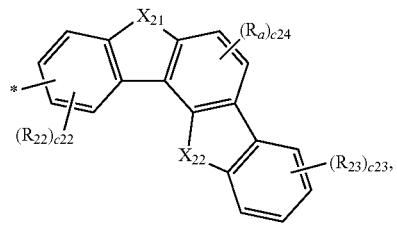

2B-6 wherein, in Formulae 2A and 2B-1 to 2B-6, c24 may be 1 or 2, and $X_{21}$, $X_{22}$, $R_a$, $R_{22}$, $R_{23}$, c22, and c23 are the same as described in the present specification.

In one embodiment, the second compound and the fourth compound may each independently be selected from compounds represented by Formulae 1-1 to 1-3.

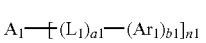

Formula 1-1

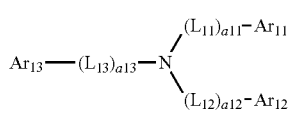

Formula 1-2

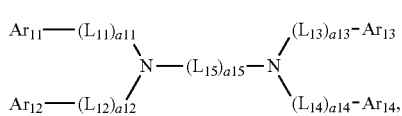

Formula 1-3 wherein, in Formulae 1-1 to 1-3, $A_1$, $L_1$, $L_{11}$ to $L_{15}$, a1, a11 to a15, $Ar_1$, $Ar_{11}$ to $Ar_{14}$, b1, and n1 are the same as described in the present specification.

In one embodiment, the fifth compound may be a compound represented by Formula 5.

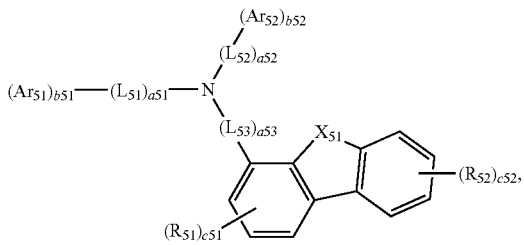

Formula 5 wherein, in Formula 5, $X_{51}$ may be O or S, $L_{51}$ to $L_{53}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a51 to a53 may each independently be an integer from 0 to 3, $Ar_{51}$ and $Ar_{52}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heterocyclic group, and —Si($Q_1$)($Q_2$)($Q_3$), b51 and b52 may each independently be an integer from 1 to 5, $R_{51}$ and $R_{52}$ may each independently be selected from hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), c51 may be an integer from 1 to 3, and c52 may be an integer from 1 to 4.

In one embodiment, the first compound and the third compound may each independently be selected from Compounds C101, C201 to C204, C301 to C333, and C401 to C428:

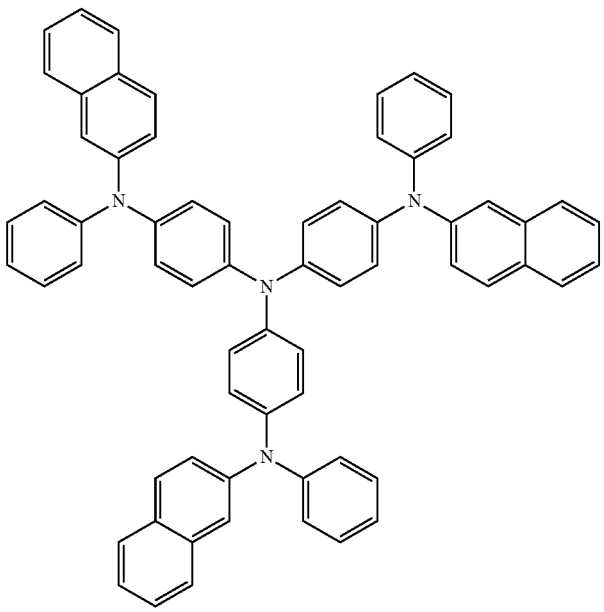

C101

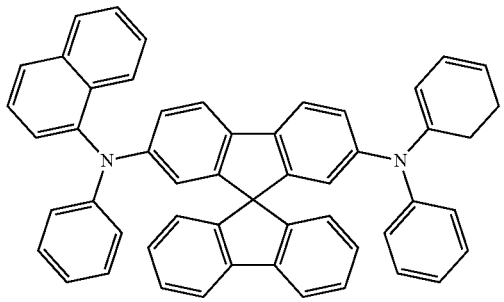

C201

-continued
C202
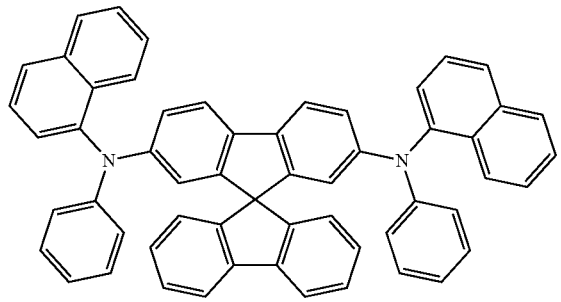
C203
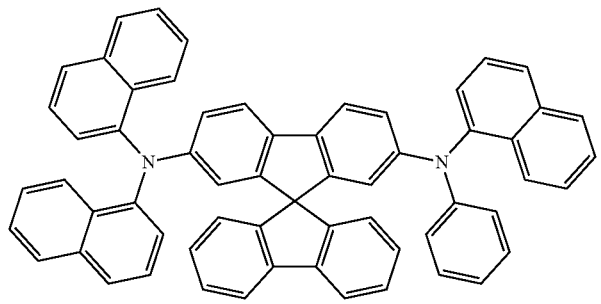
C204
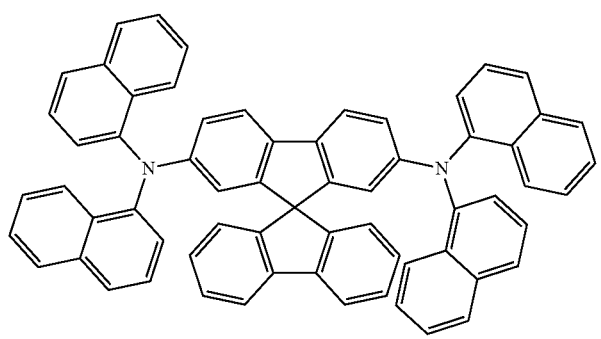
C301
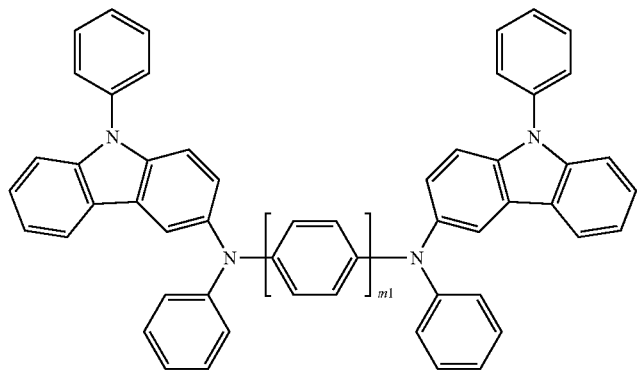

-continued
C302
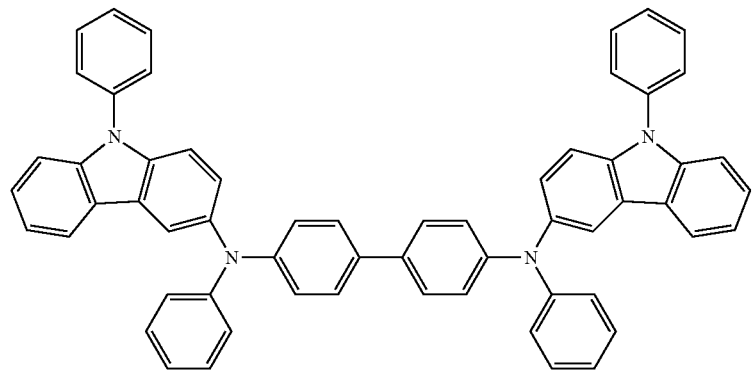
C303
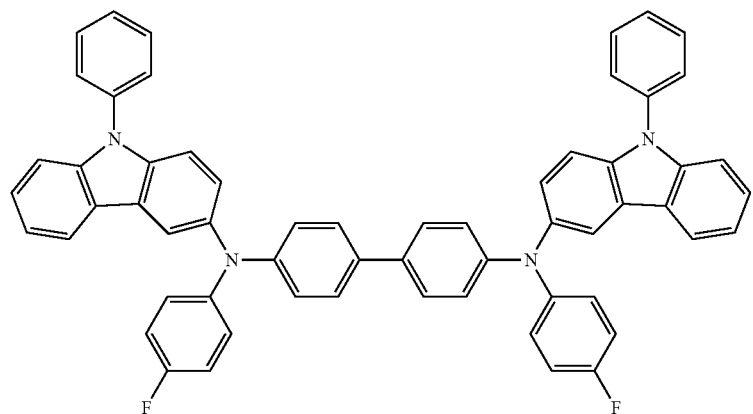
C304
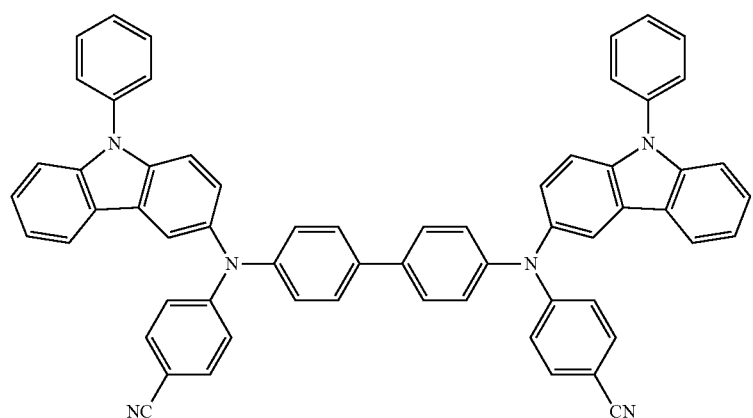
C305
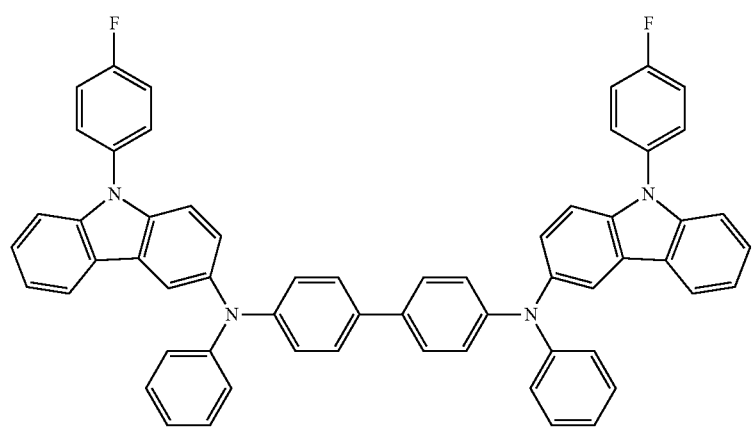

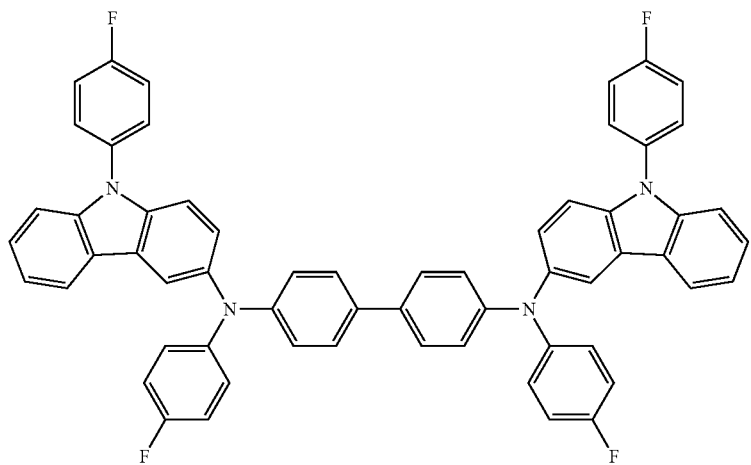
C306
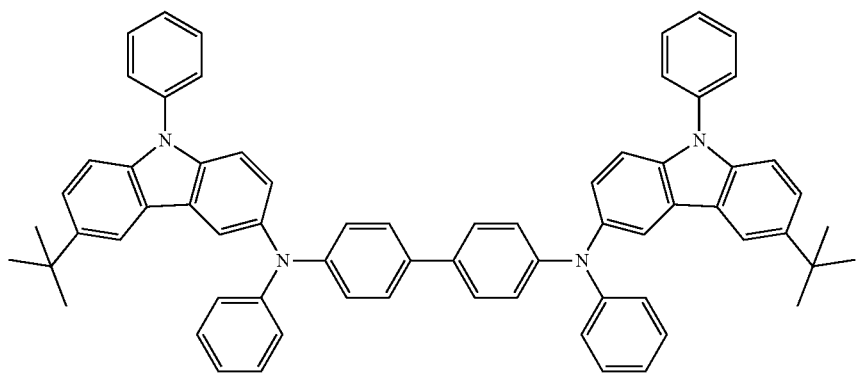
C307
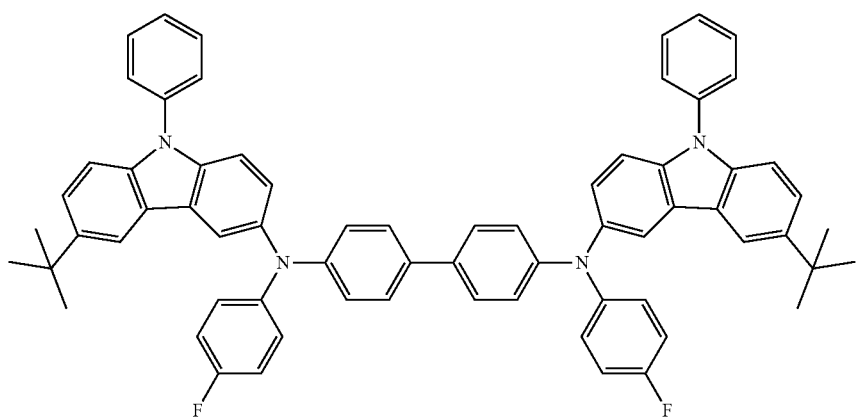
C308

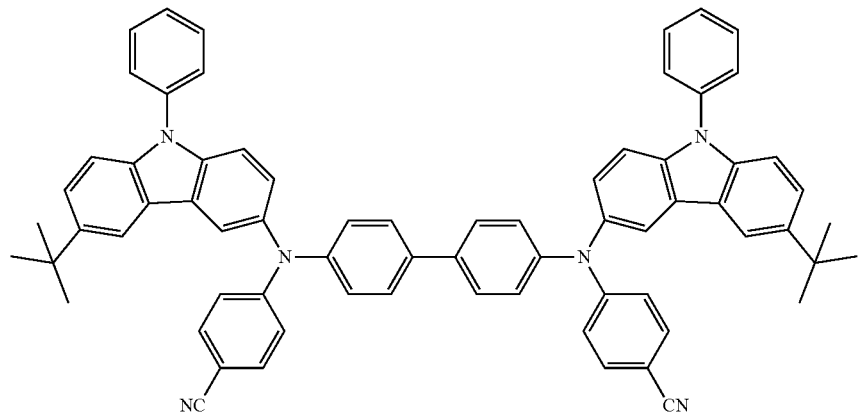
C309
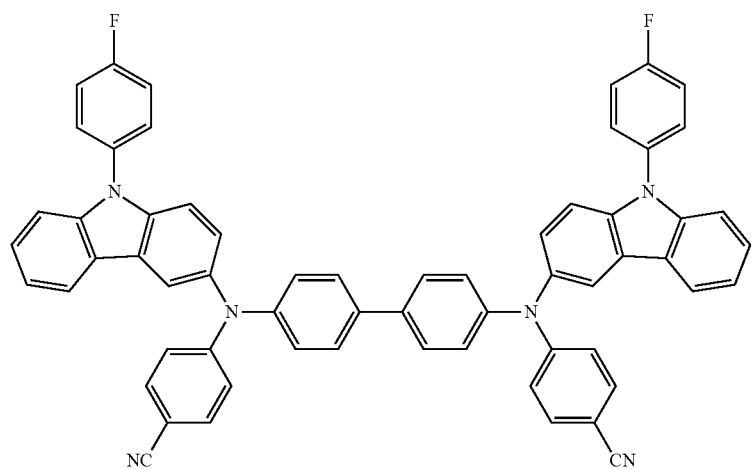
C310
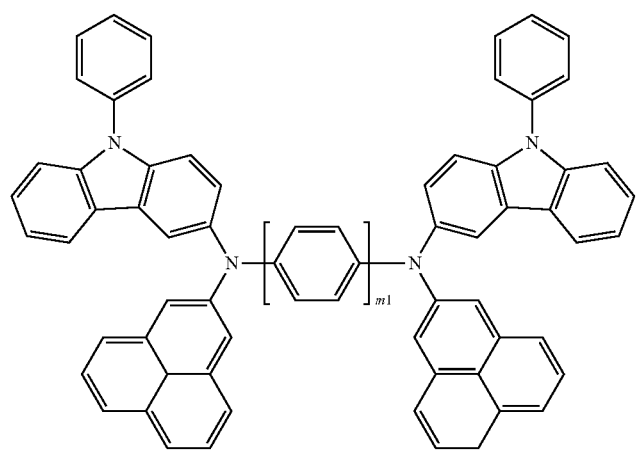
C311

-continued
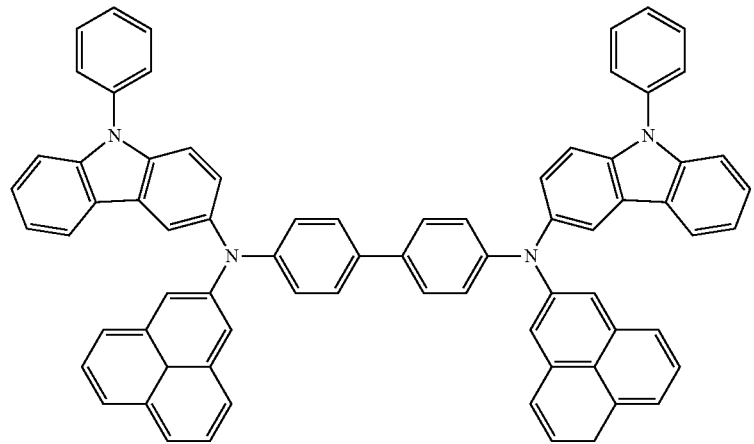
C312
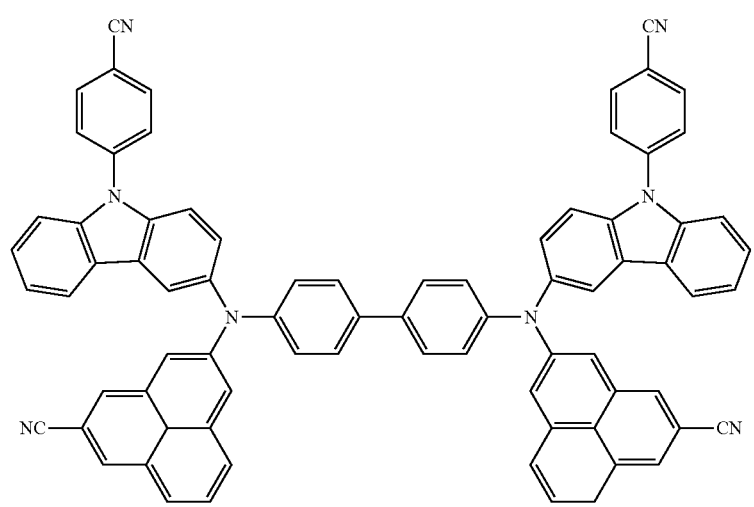
C313
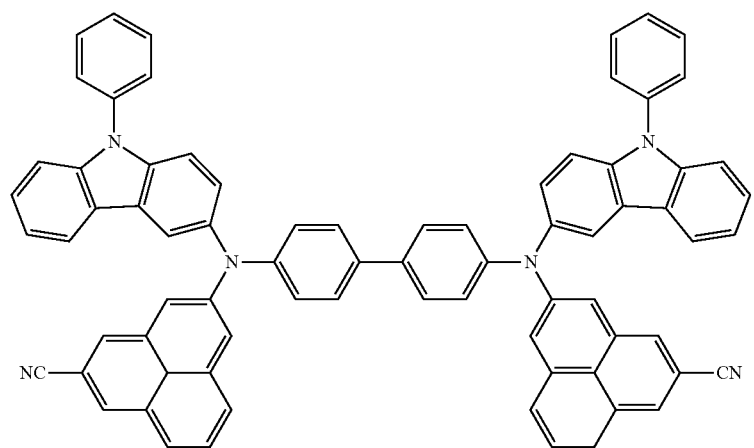
C314

-continued
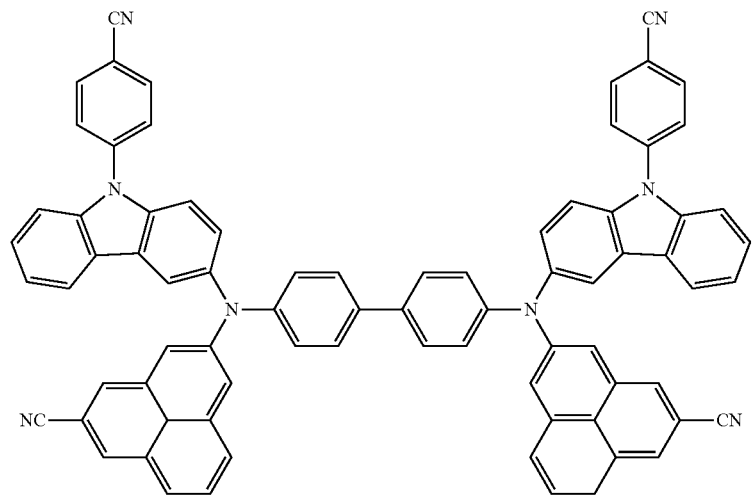
C315
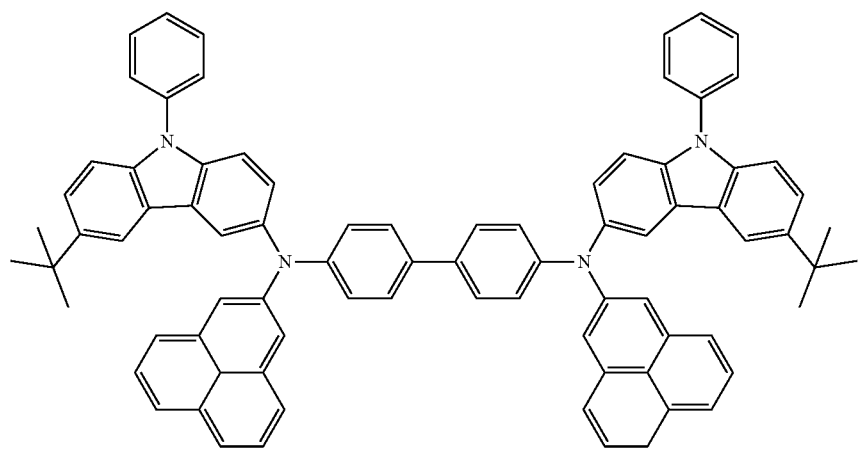
C316
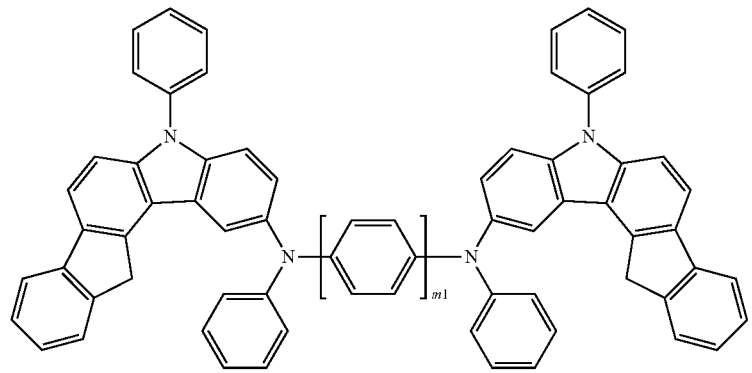
C317

-continued
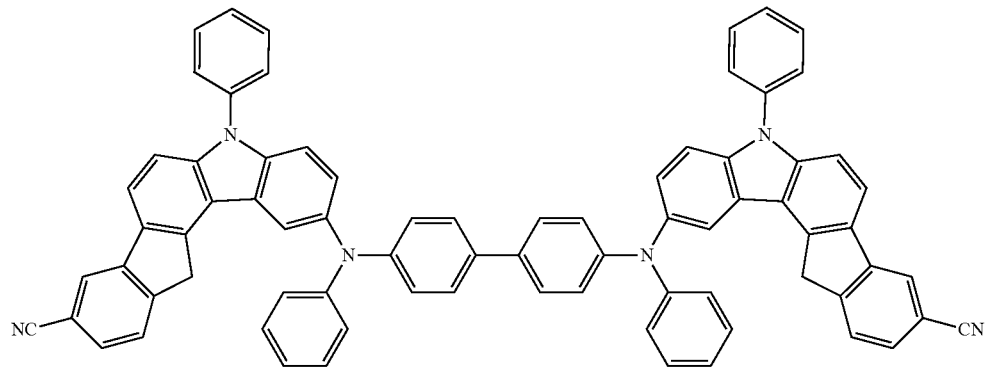
C318
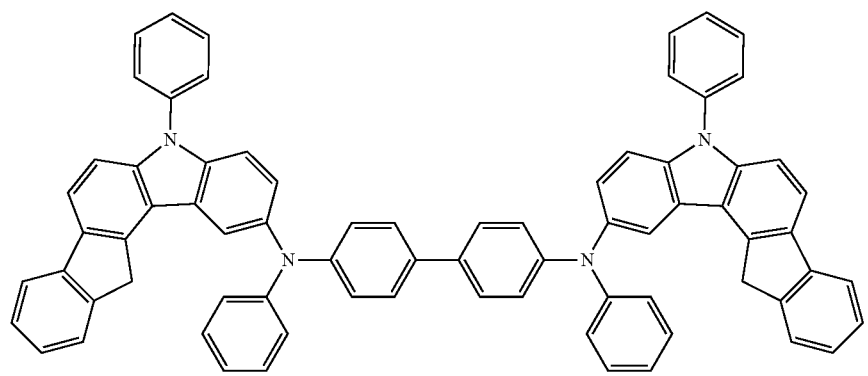
C319
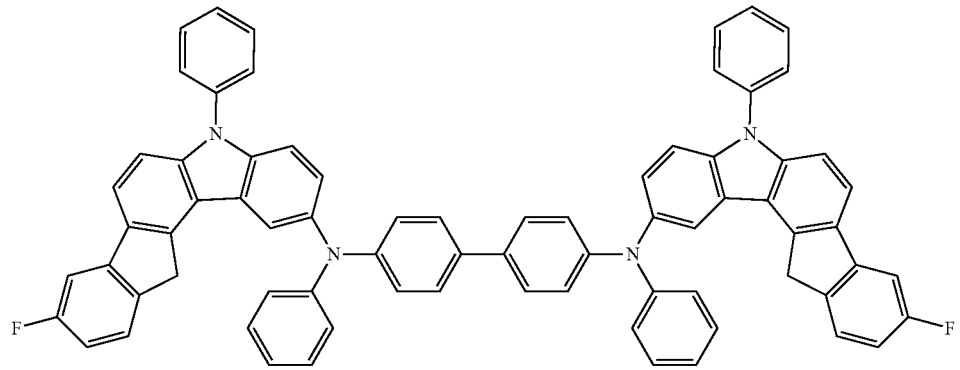
C320
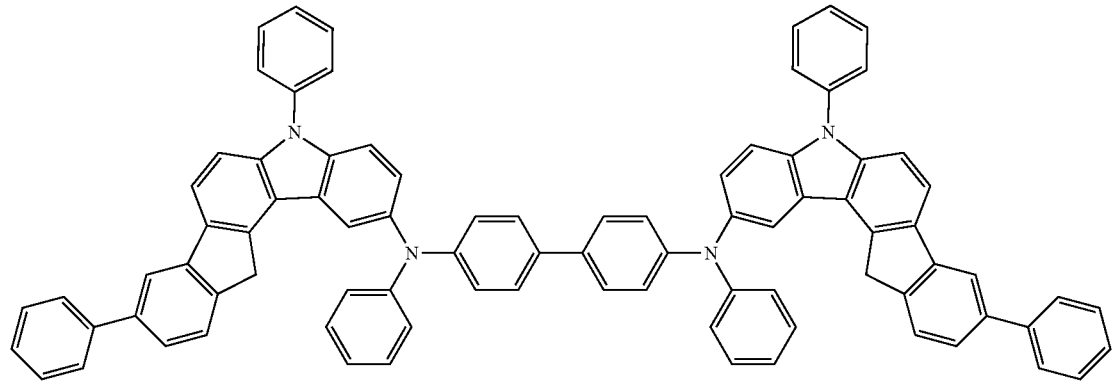
C321

-continued
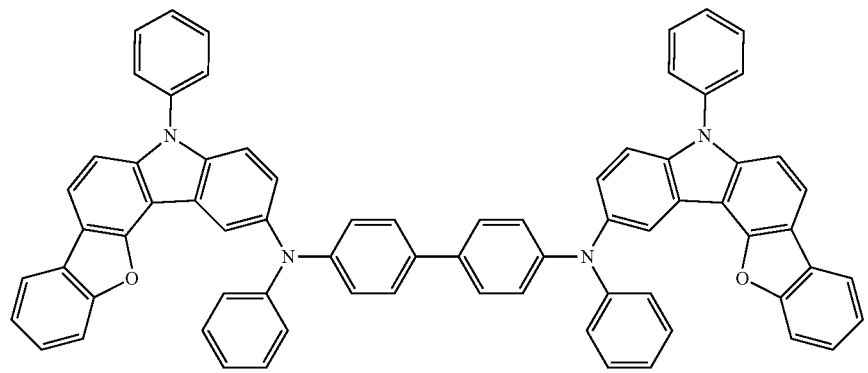
C322
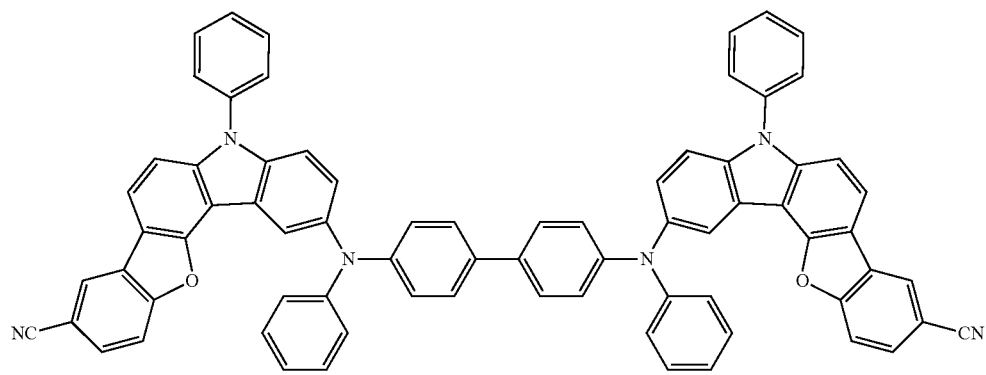
C323
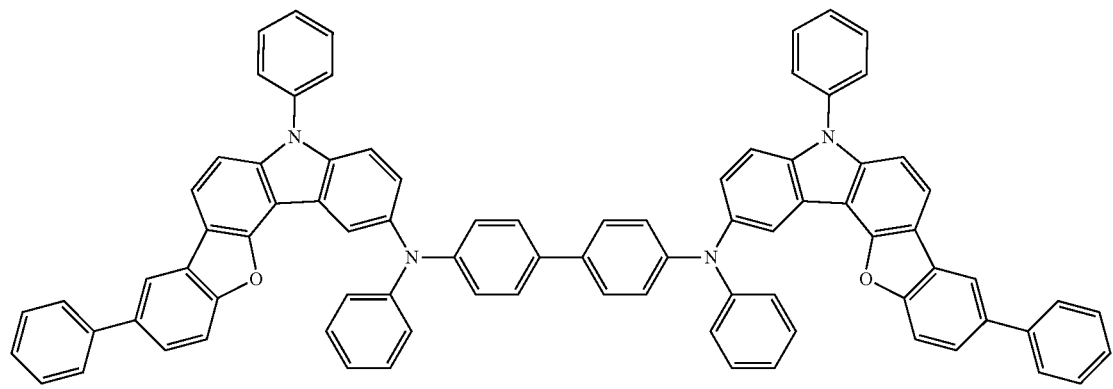
C324
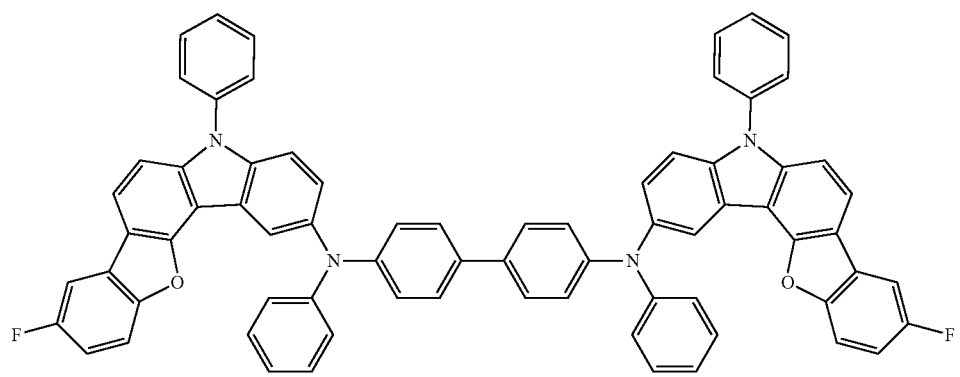
C325

-continued
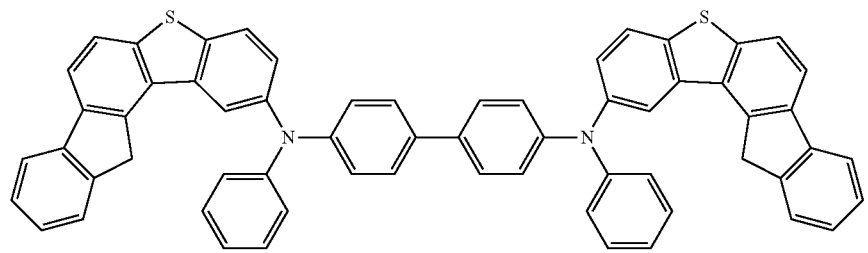
C326
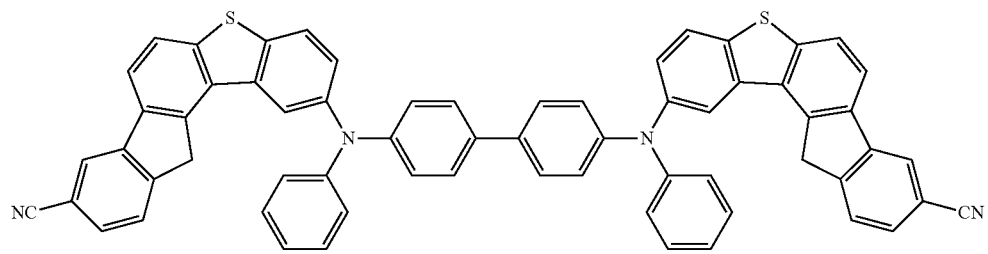
C327
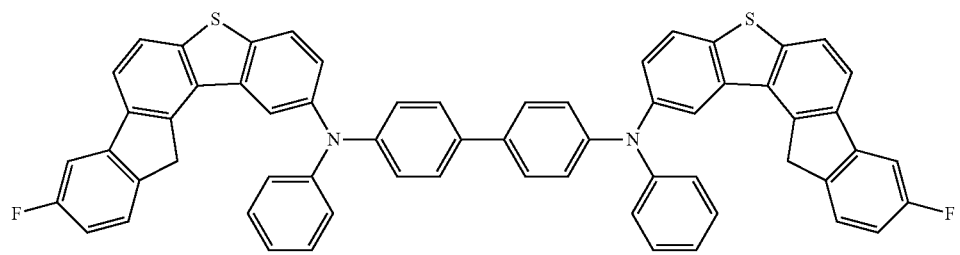
C328
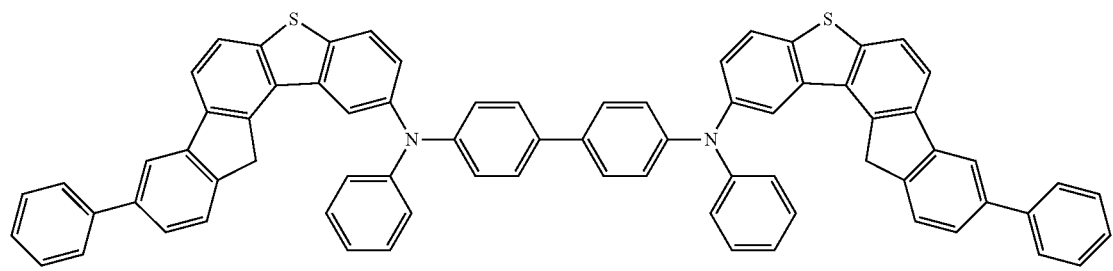
C329
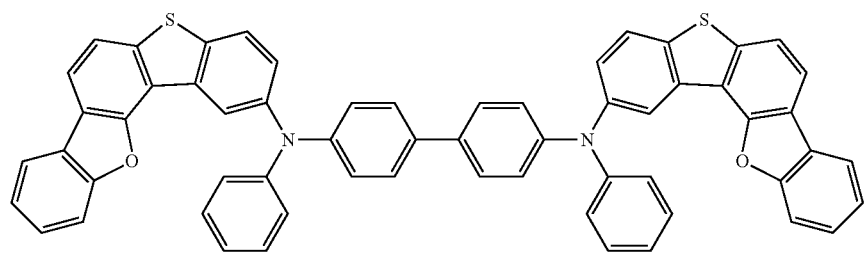
C330
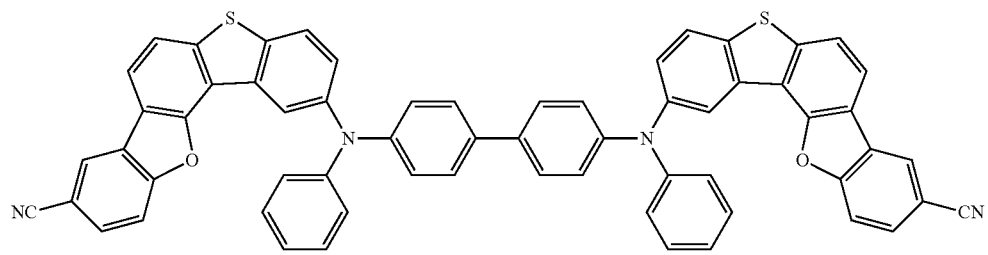
C331

-continued
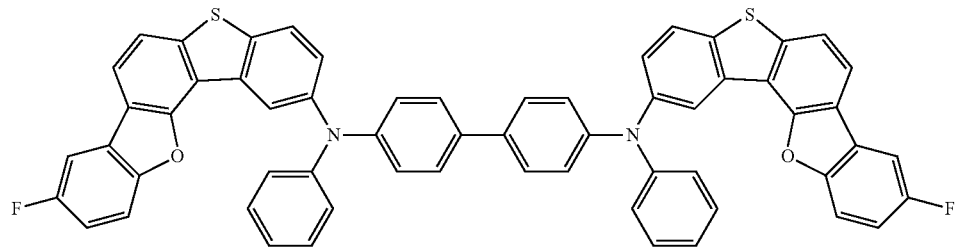
C332
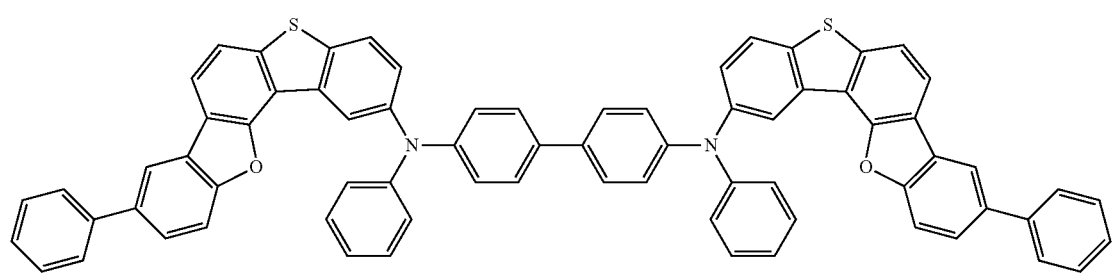
C333
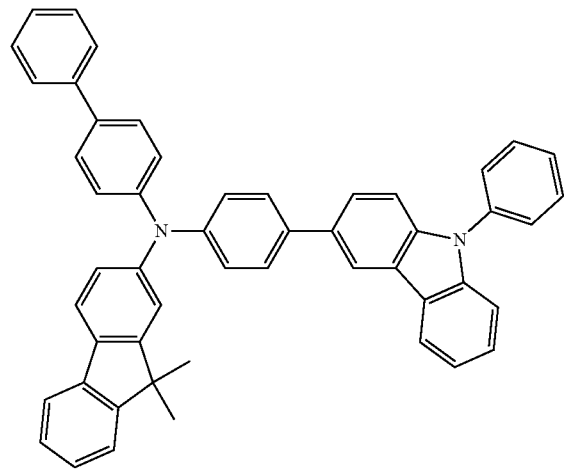
C401
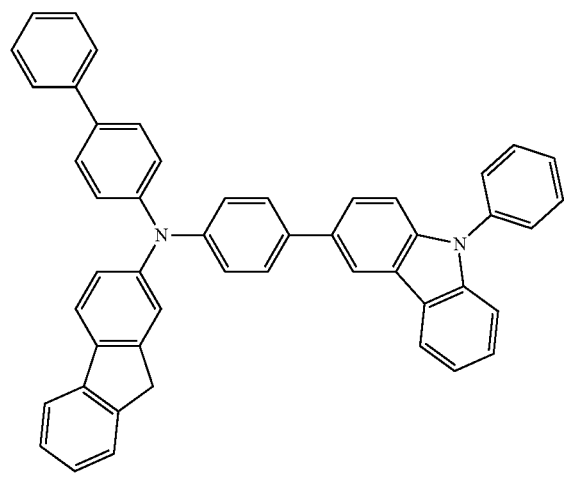
C402

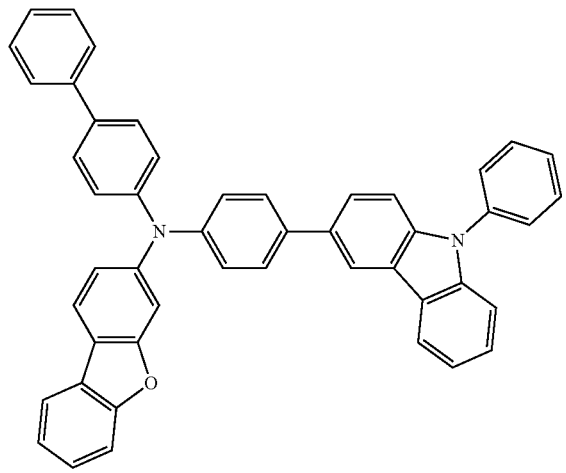
C403
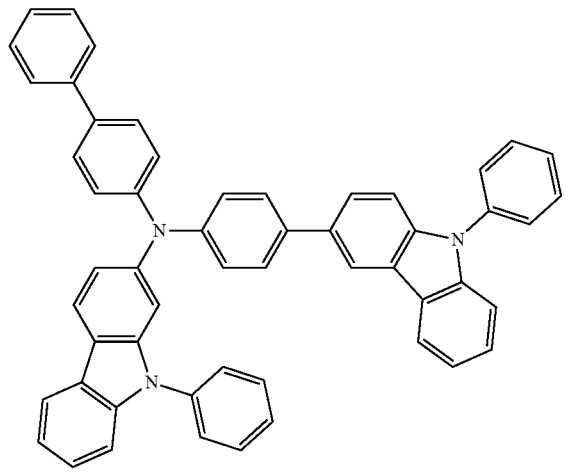
C404
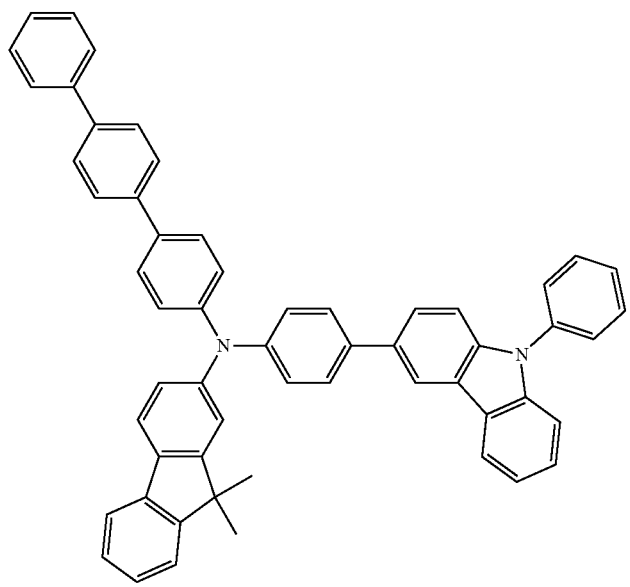
C405

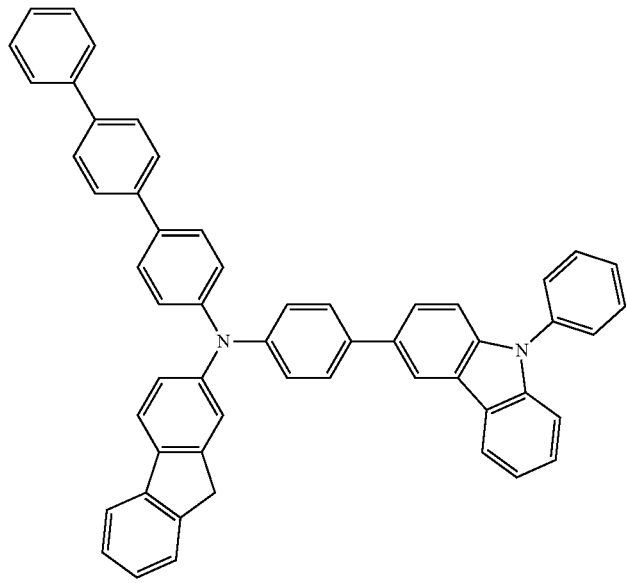
C406
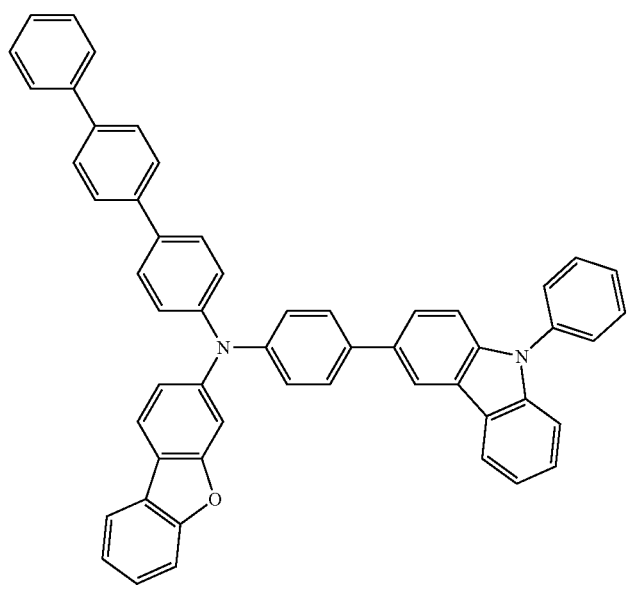
C407

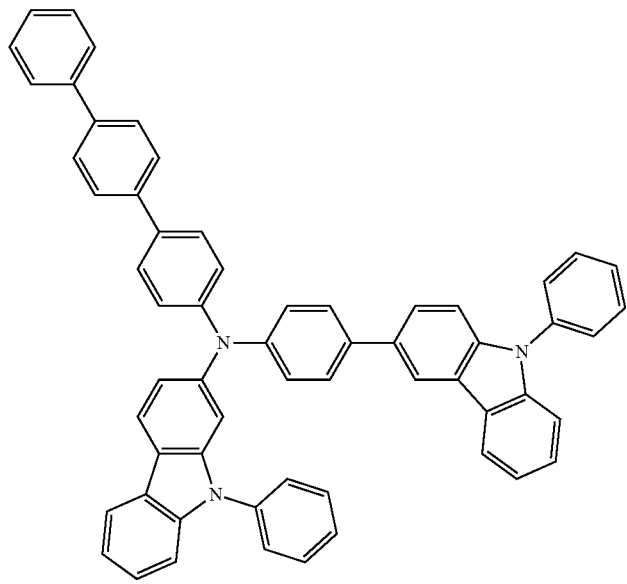
C408
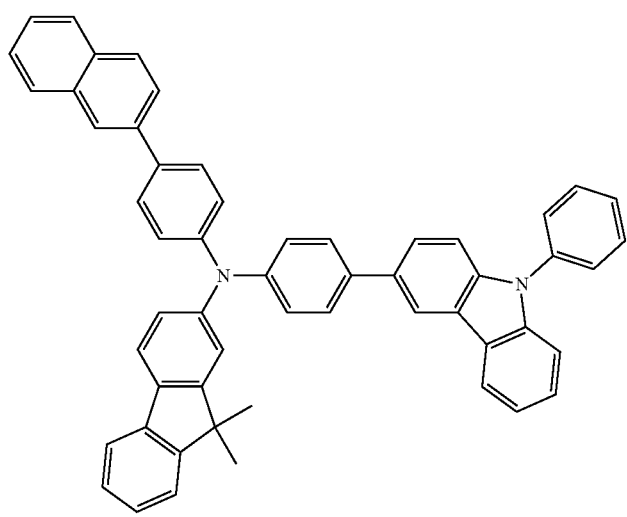
C409
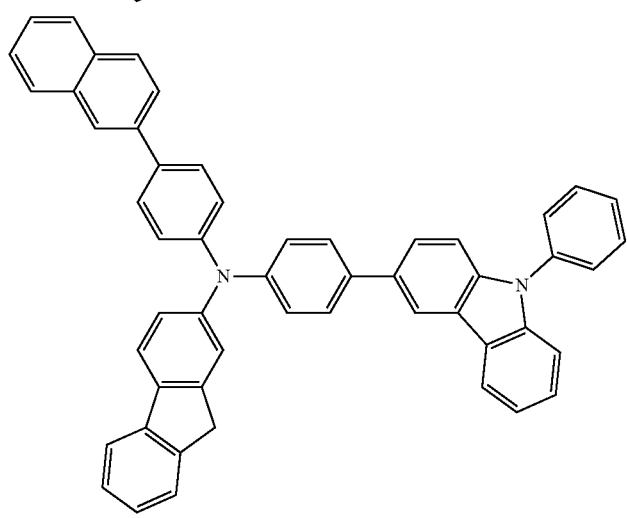
C410

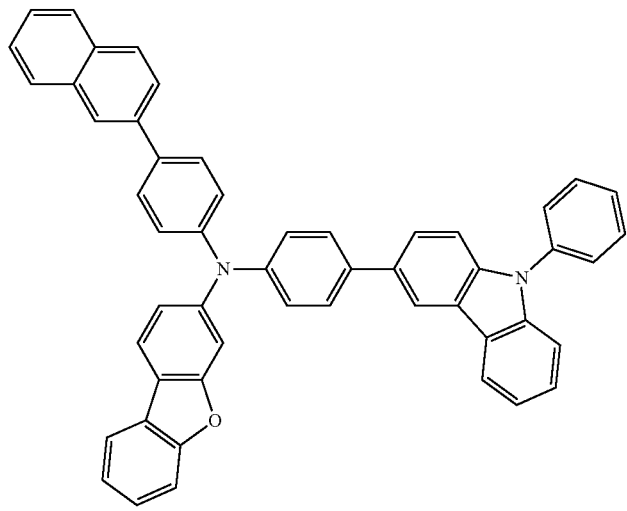
C411
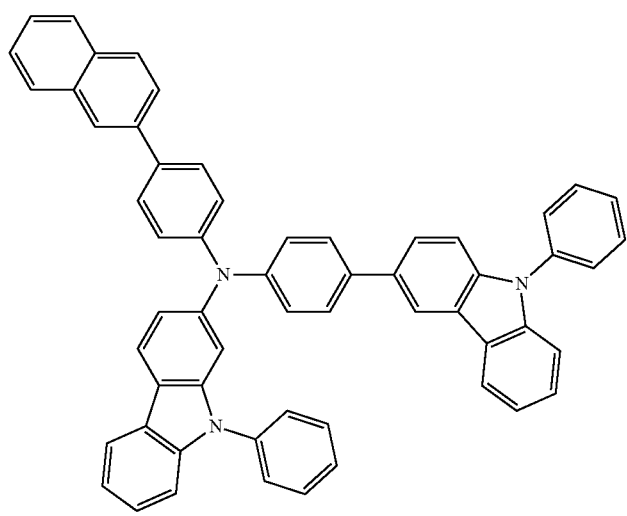
C412
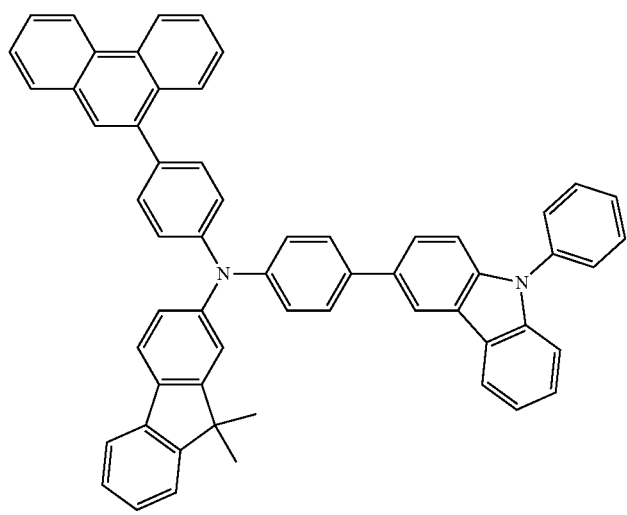
C413

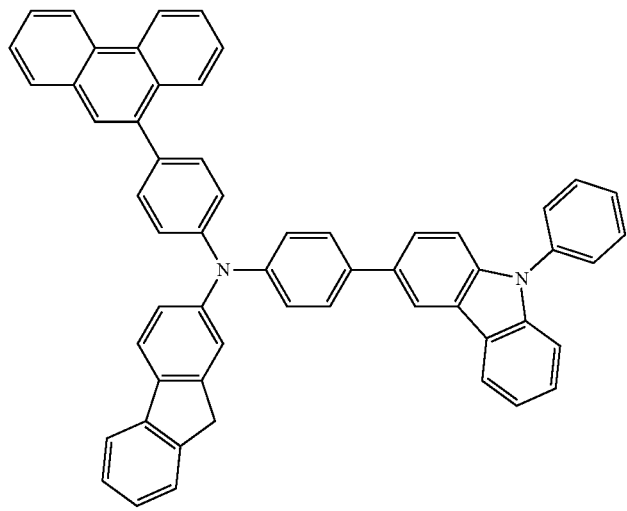
C414
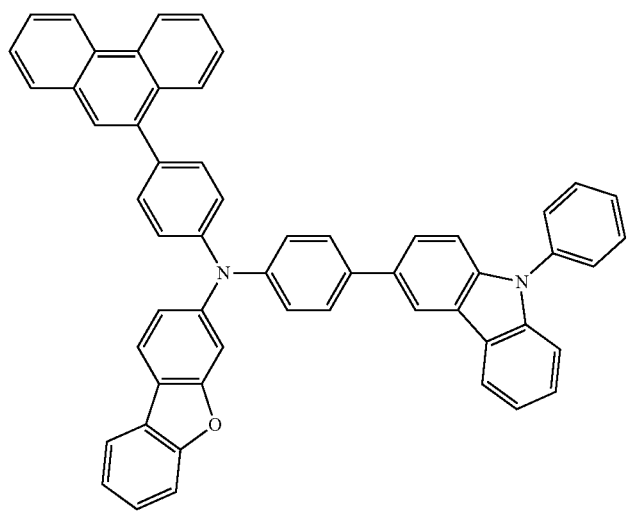
C415
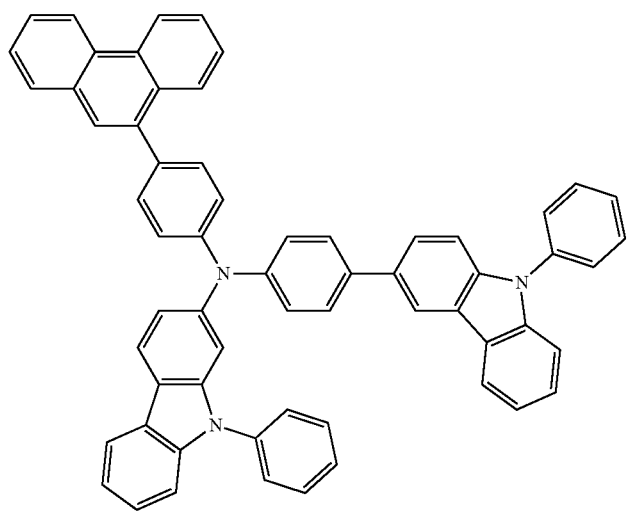
C416

-continued
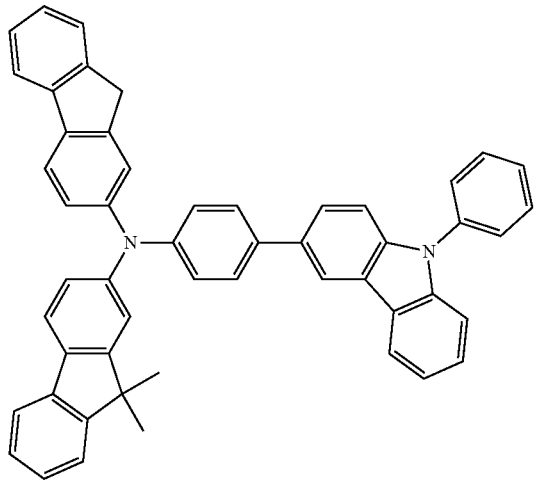
C417
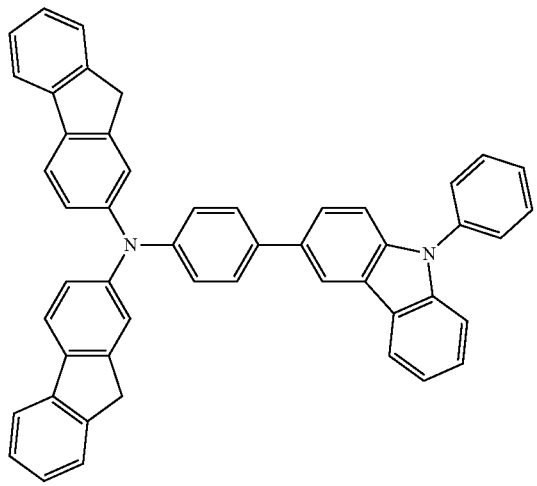
C418
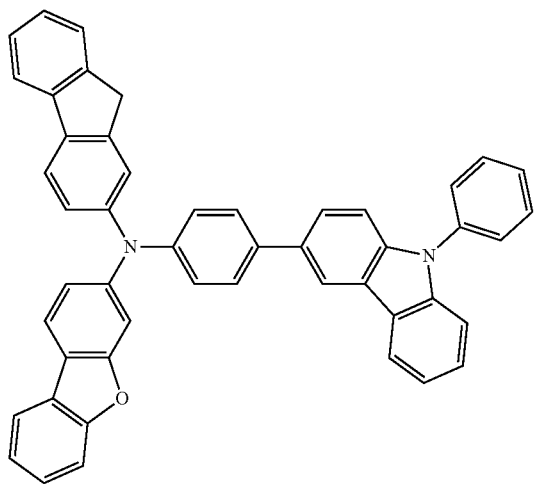
C419

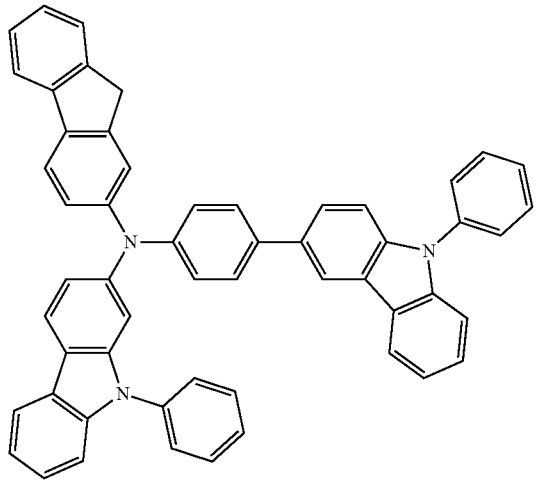
C420
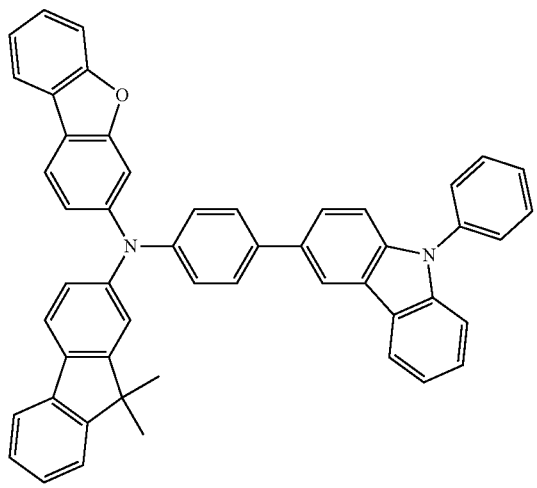
C421
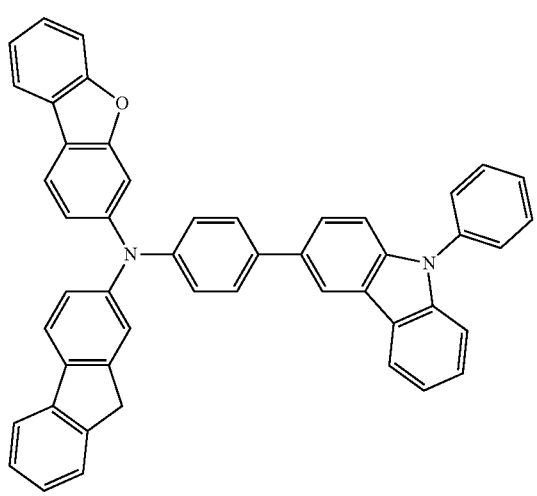
C422

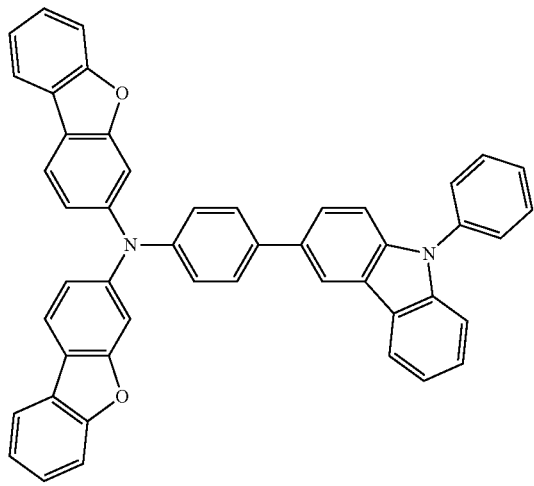
C423
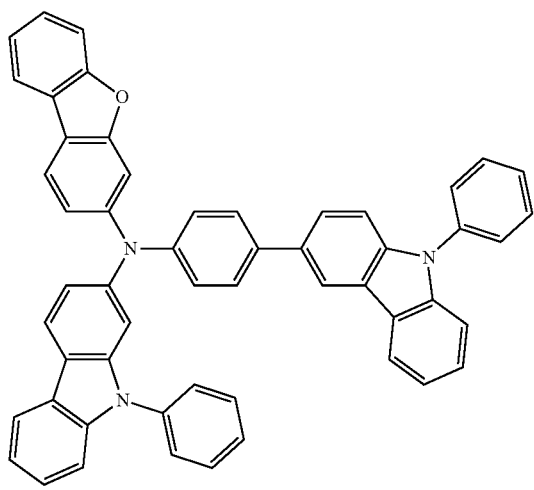
C424
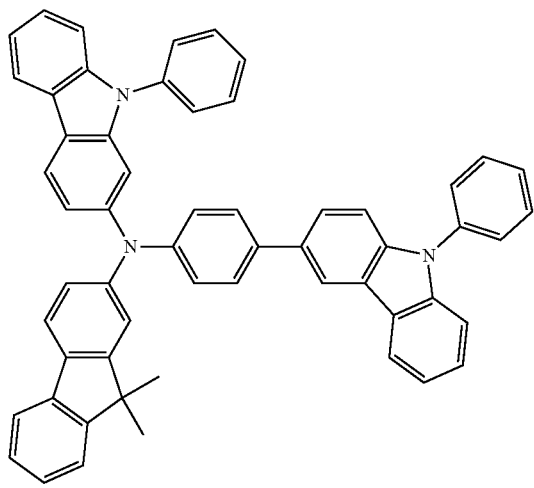
C425

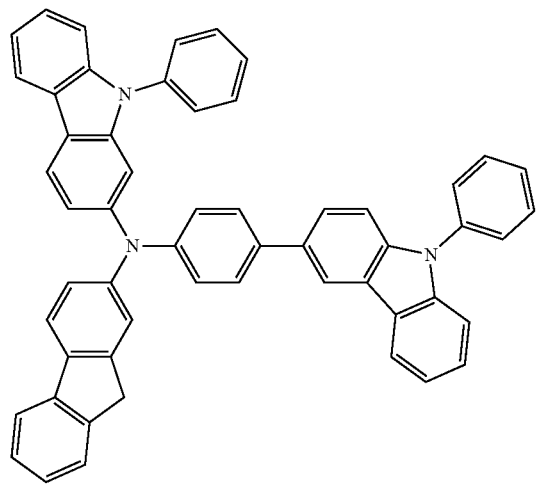
C426
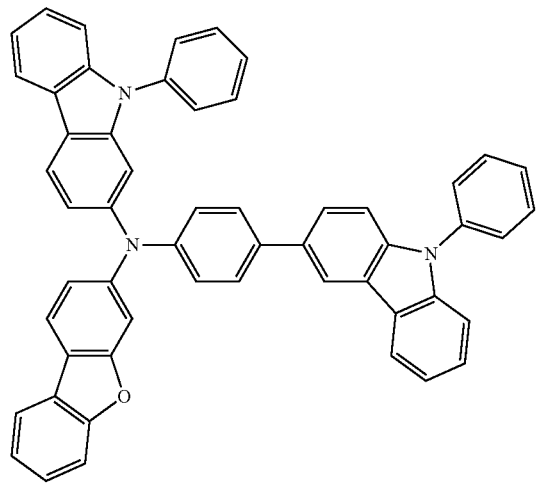
C427
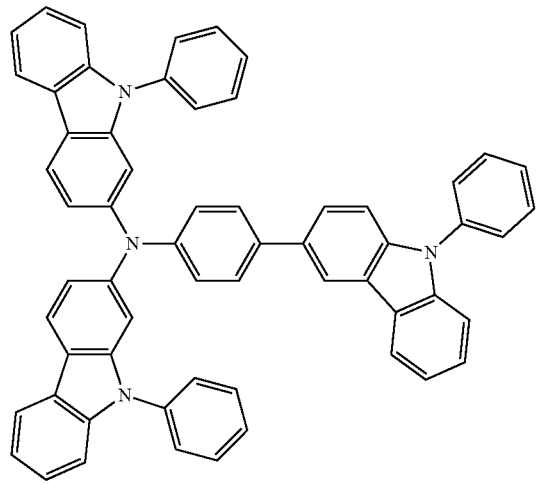
C428

For example, the first compound may be selected from Compounds C101 and C201 to C204. In one or more embodiments, the third compound may be Compounds C301 to C333 and C401 to C428.
In one embodiment, the second compound and the fourth compound may each independently be selected from Compounds C201 to C204 and C401 to C428:
C201
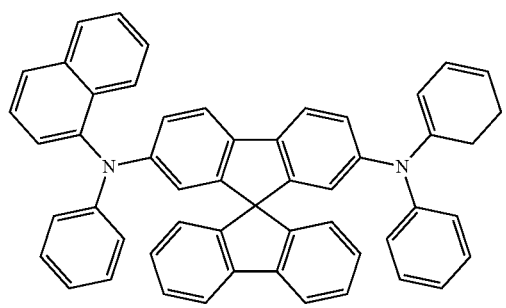
C202
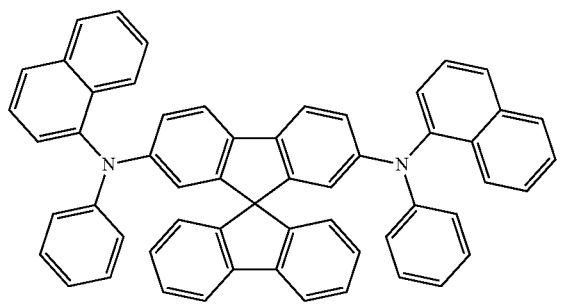
C203
C204
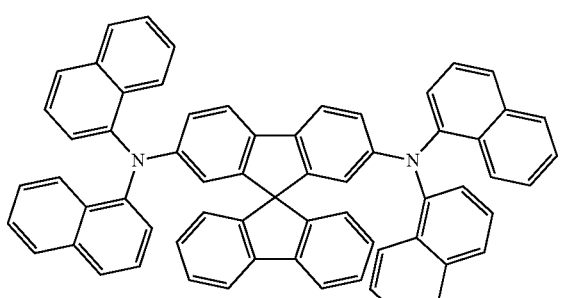
-continued
C401
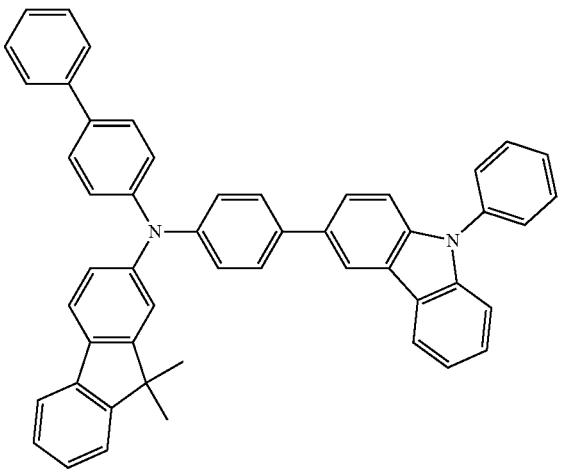
C402
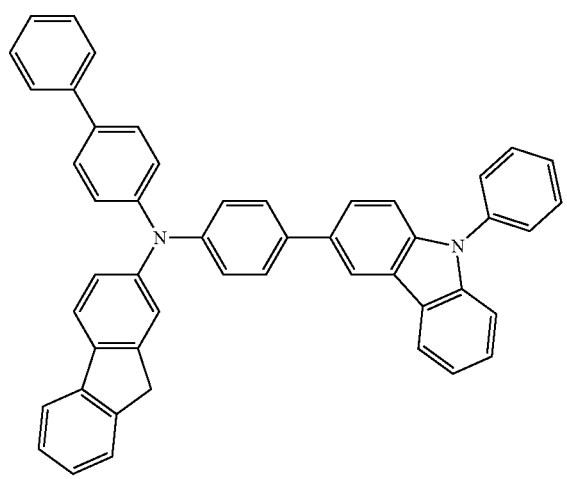
C403
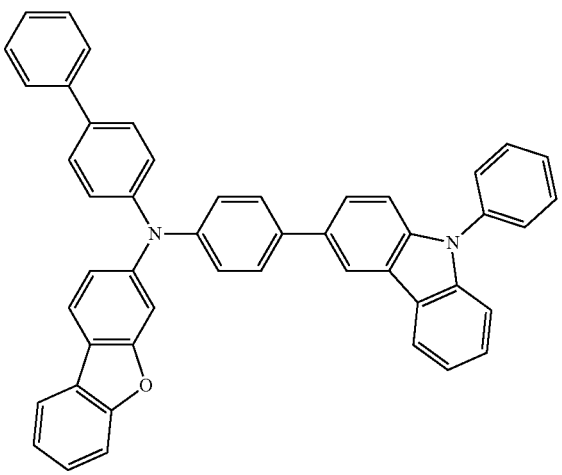

C404
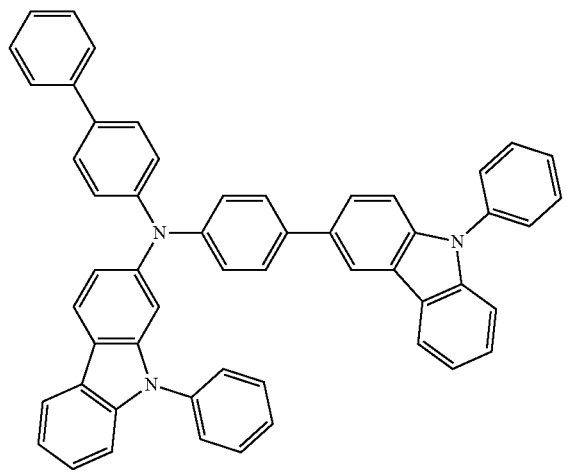
C405
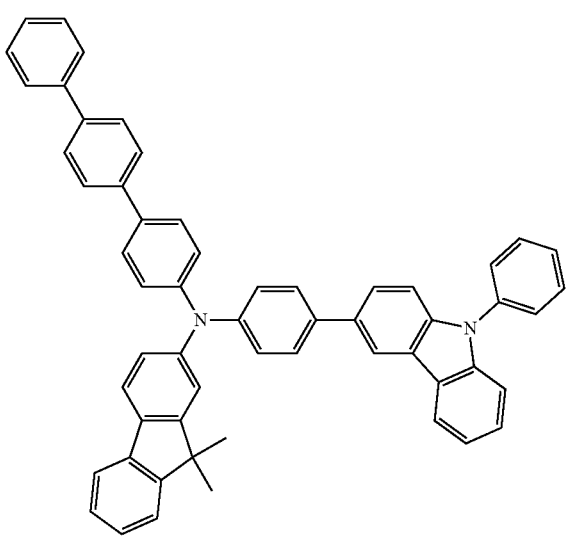
C406
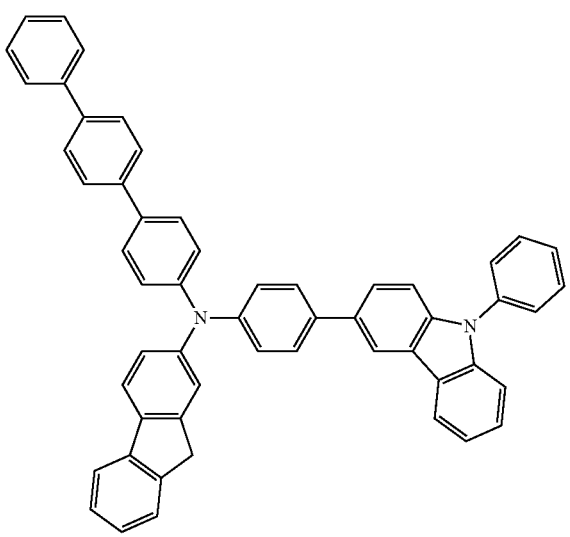
C407
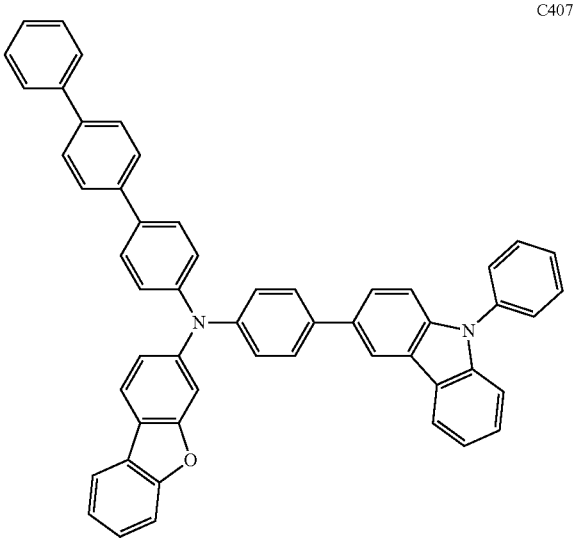
C408
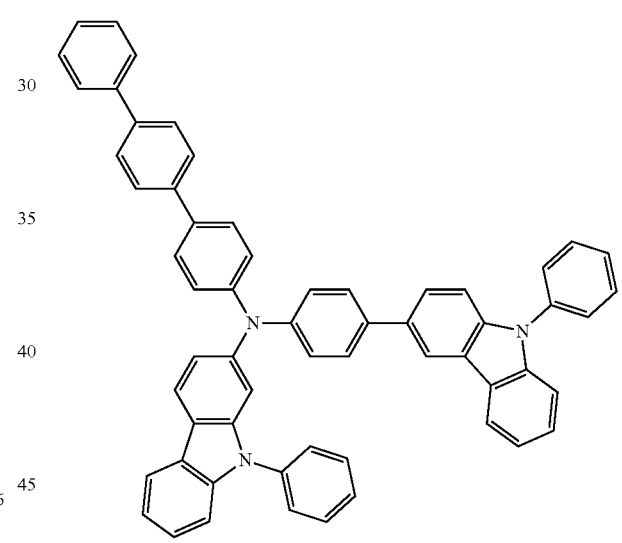
C409
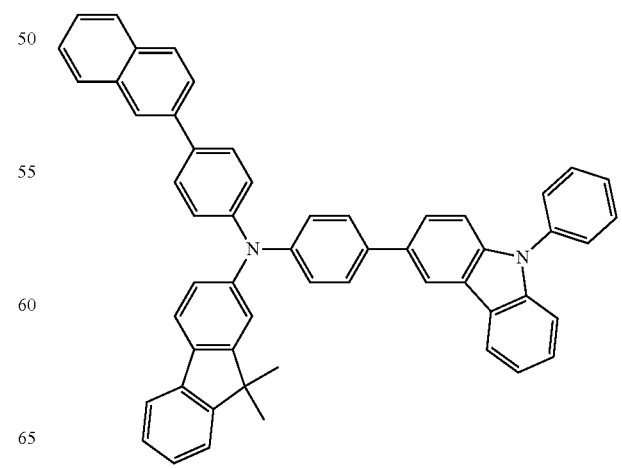

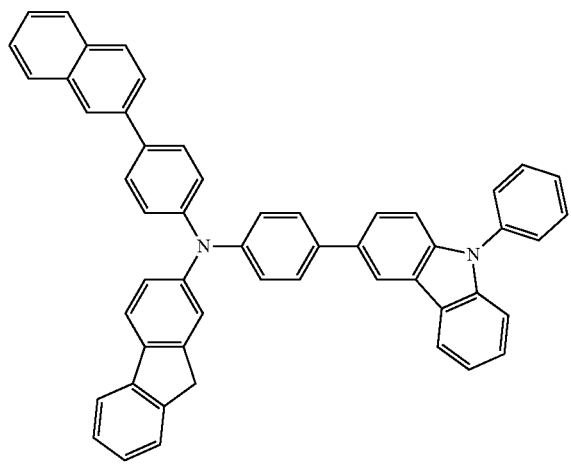 C410
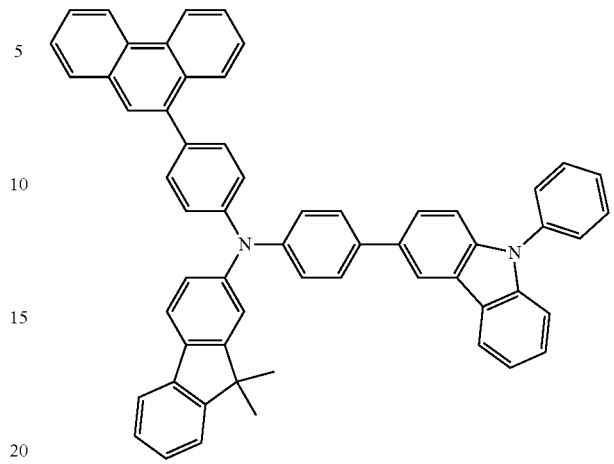 C413
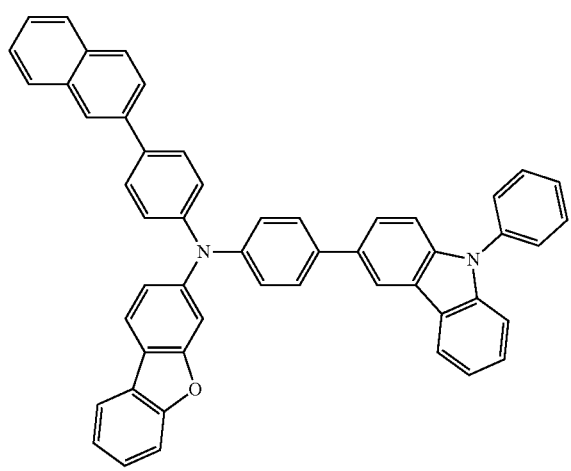 C411
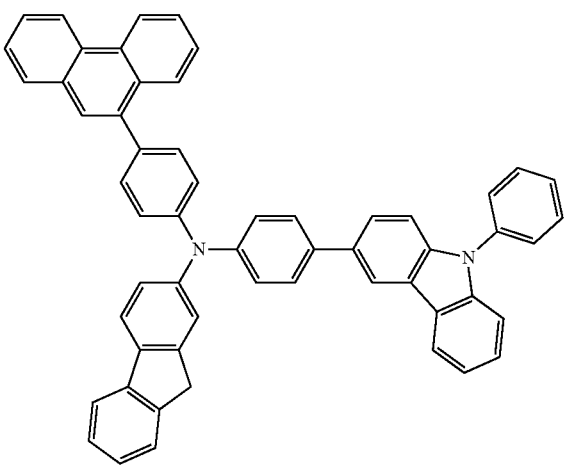 C414
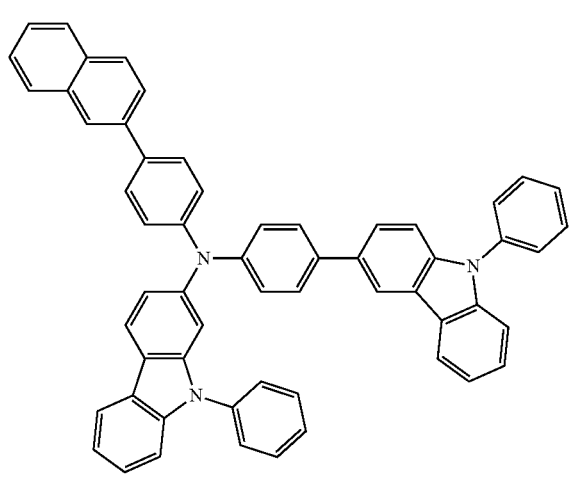 C412
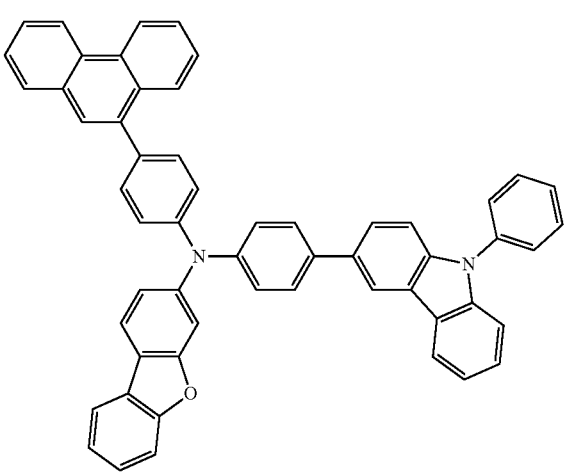 C415

C416
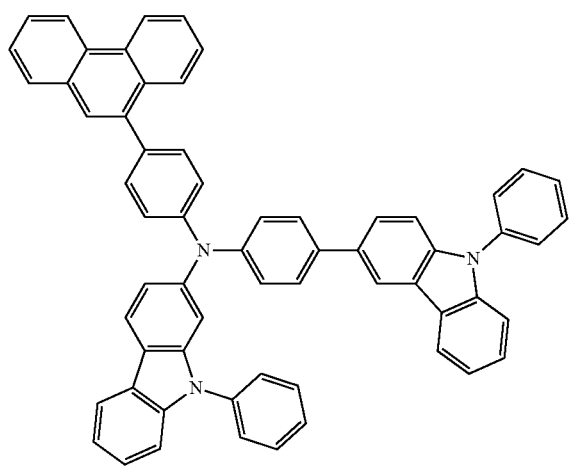
C419
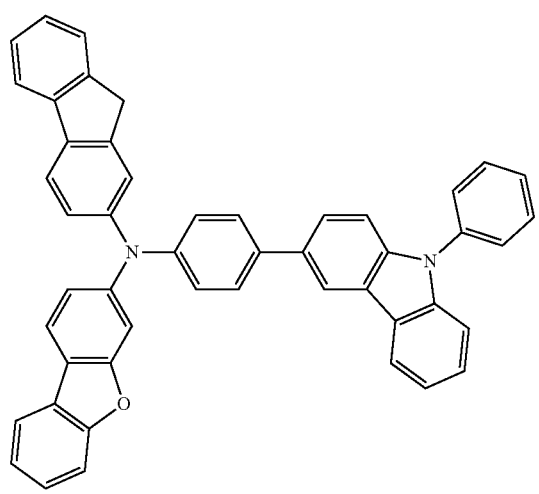
C417
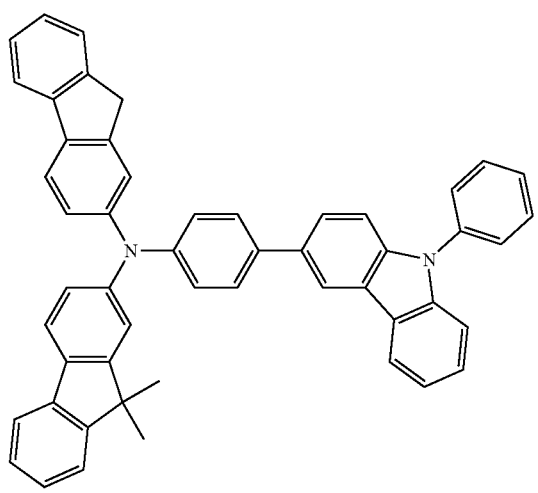
C420
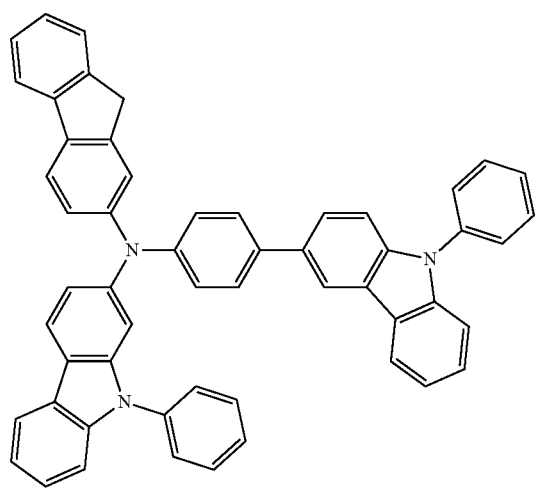
C418
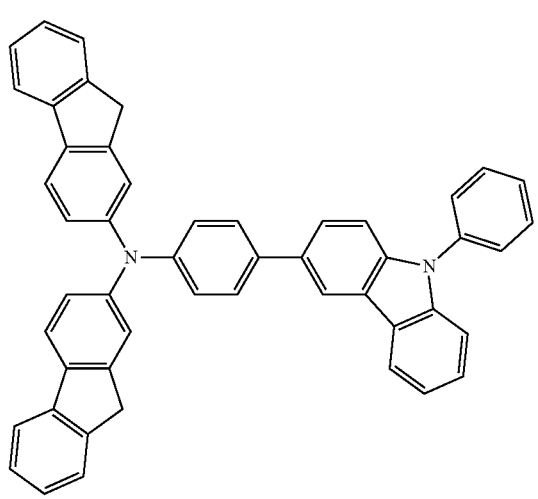
C421
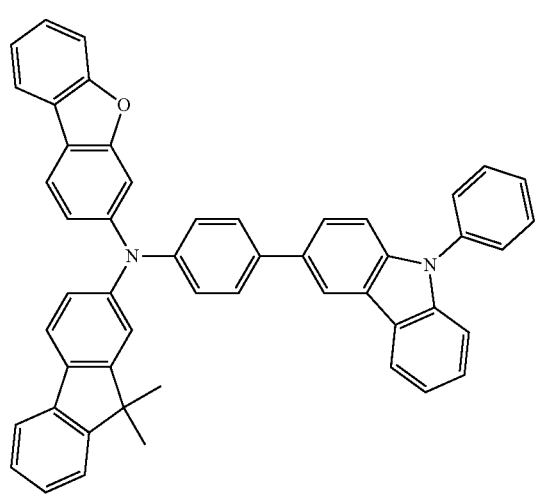

C422
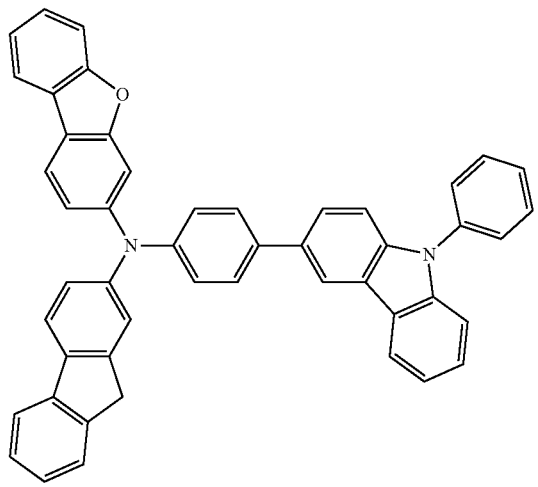
C425
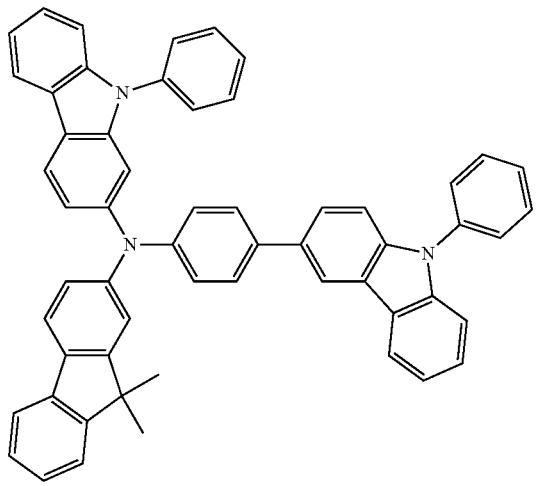
C423
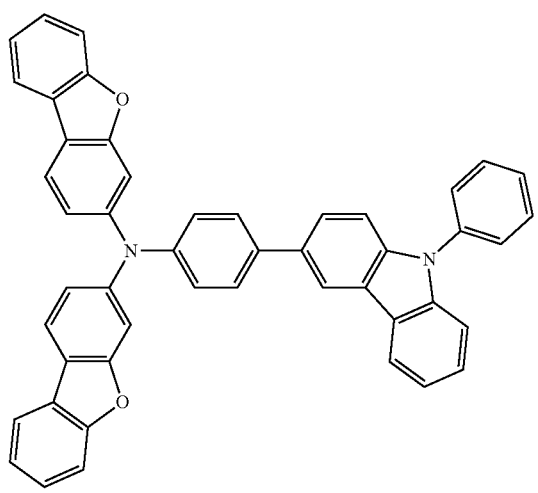
C426
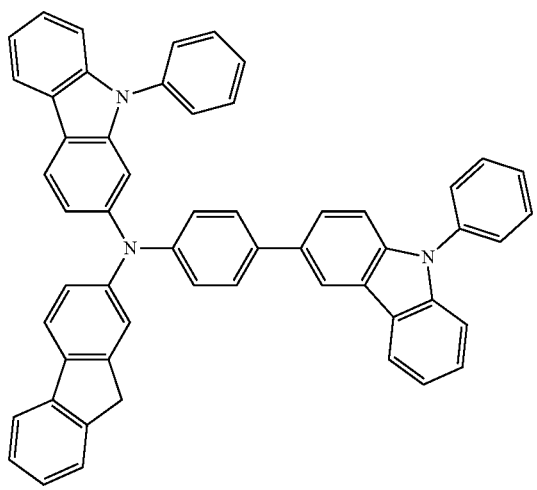
C424
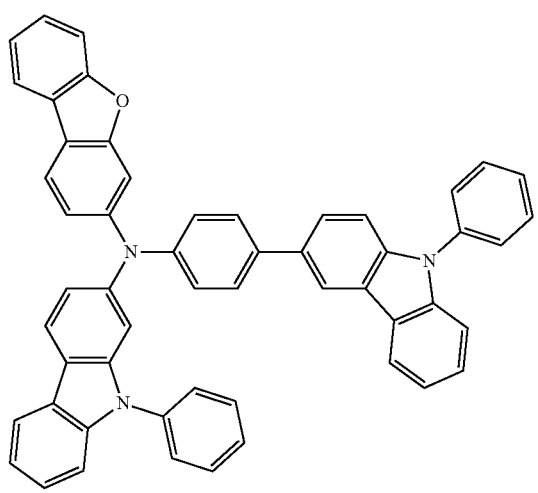
C427
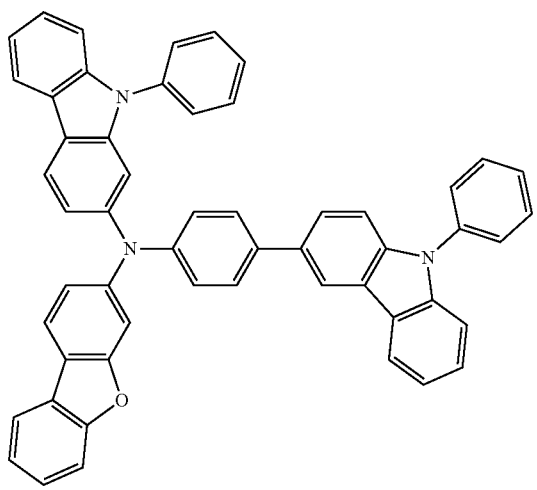

C428
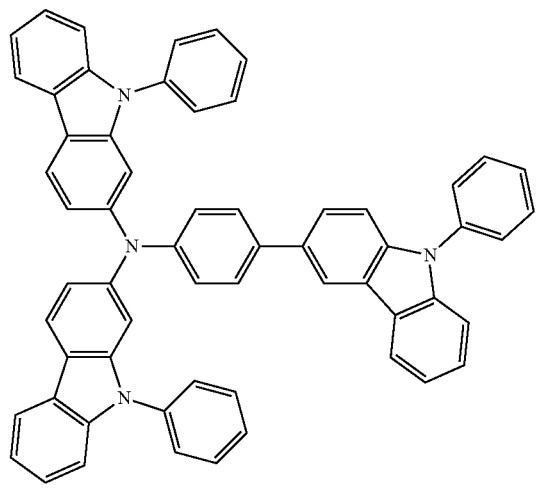
For example, the second compound may be selected from Compounds C201 to C204, and the fourth compound may be selected from Compounds C401 to C428.
In one embodiment, the fifth compound may be selected from Compounds C501 to C560:
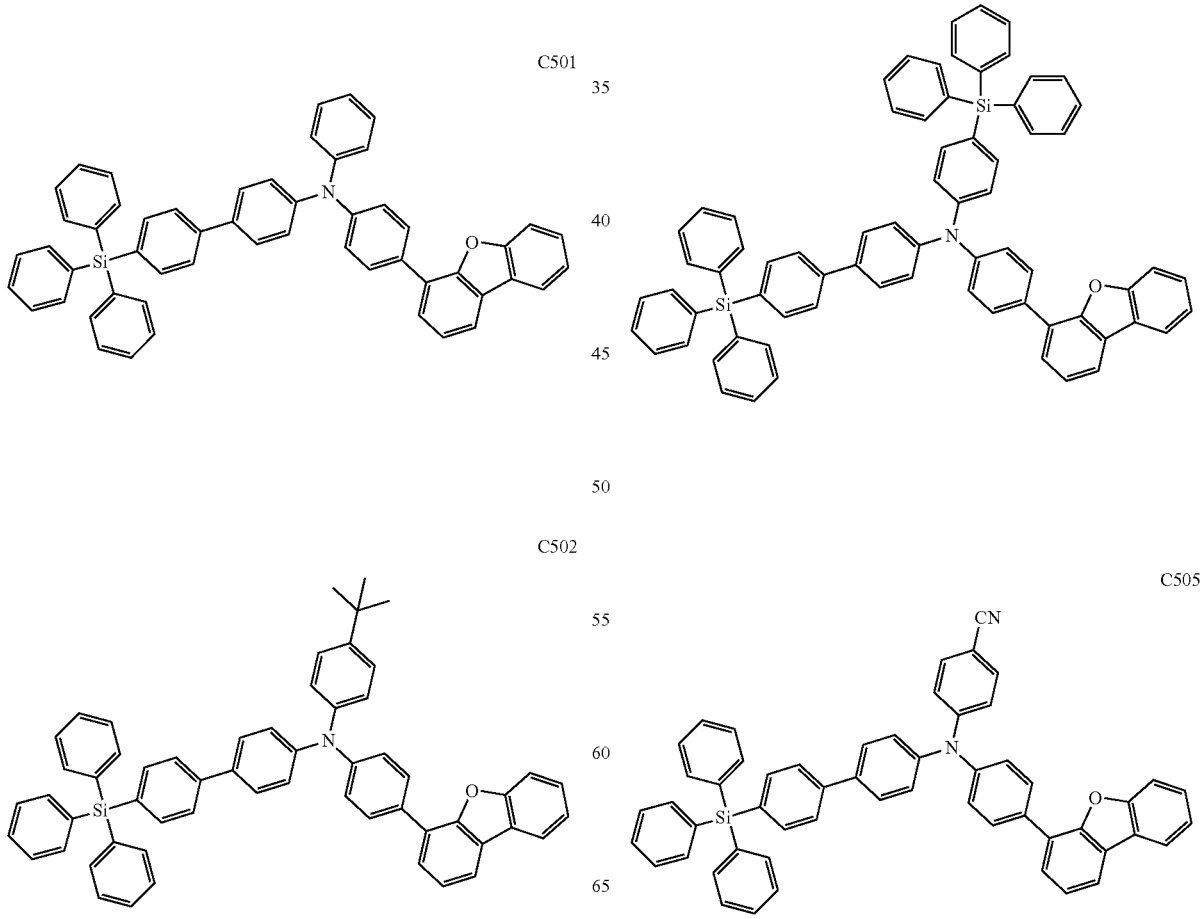

-continued
C506
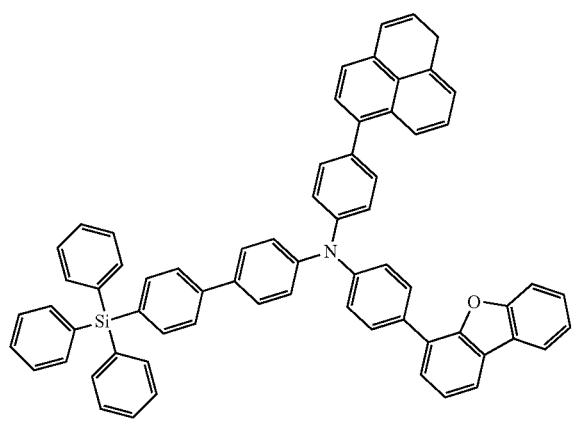
C507
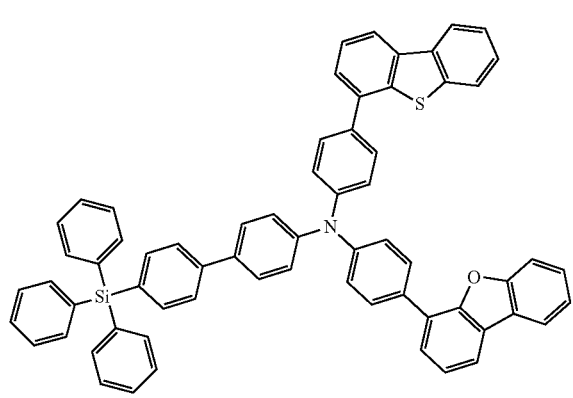
C508
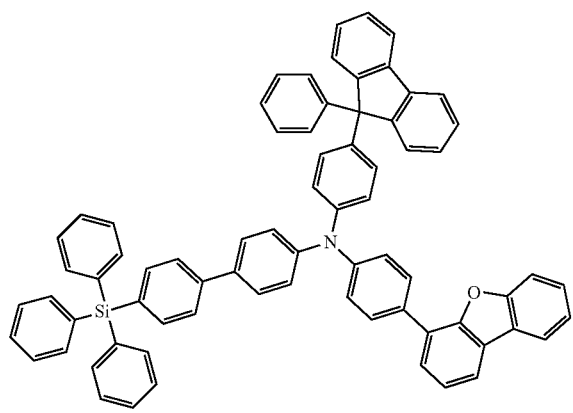
C509
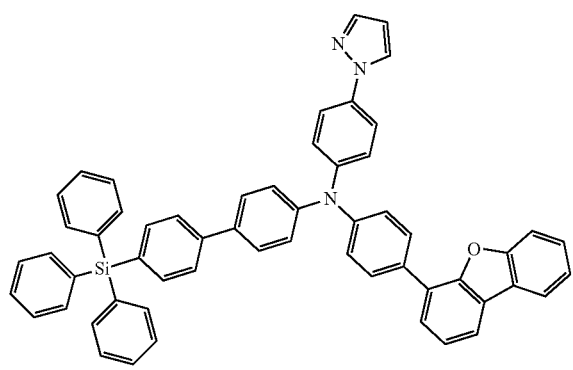
-continued
C510
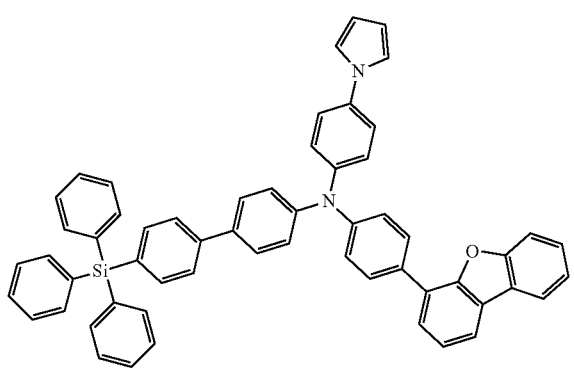
C511
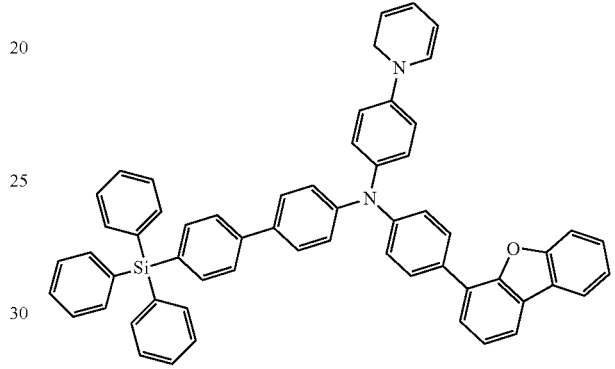
C512
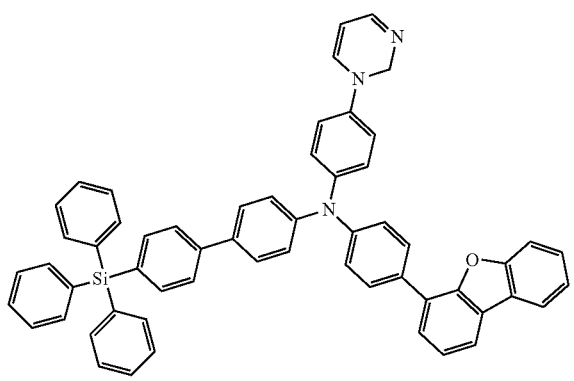
C513
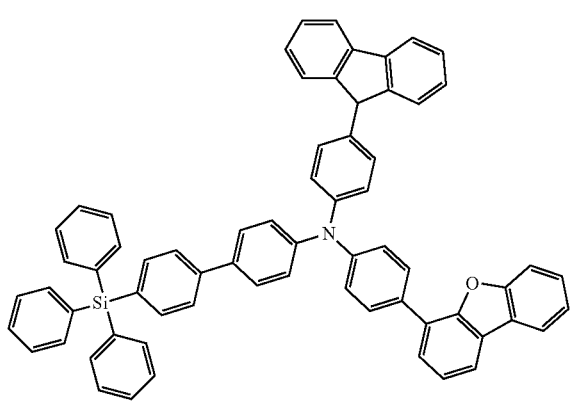

C514
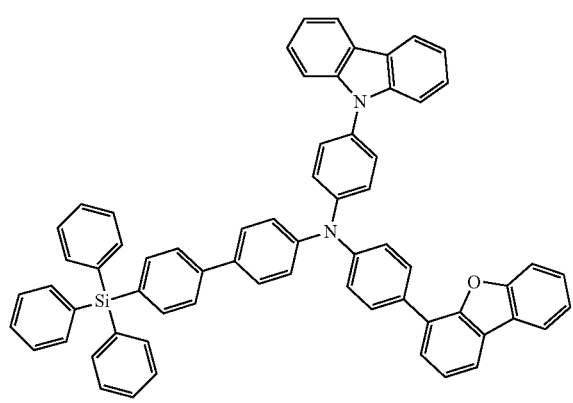
C515
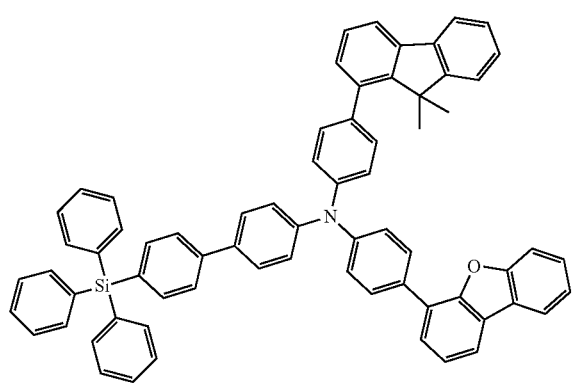
C516
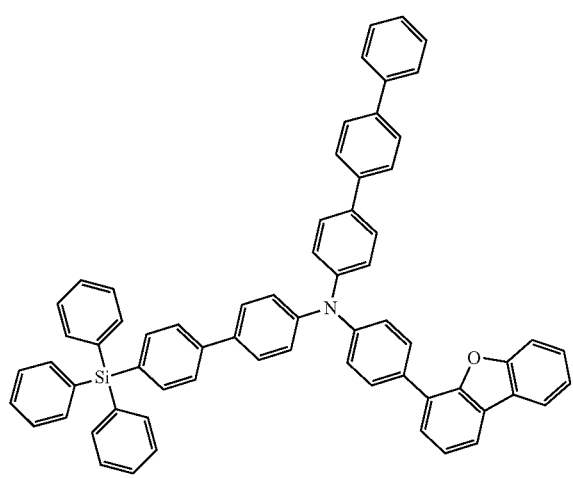
C517
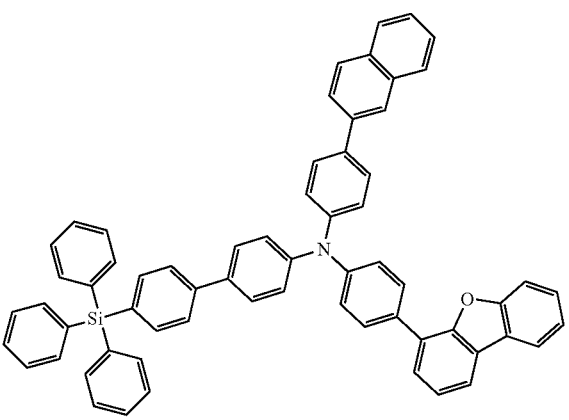
C518
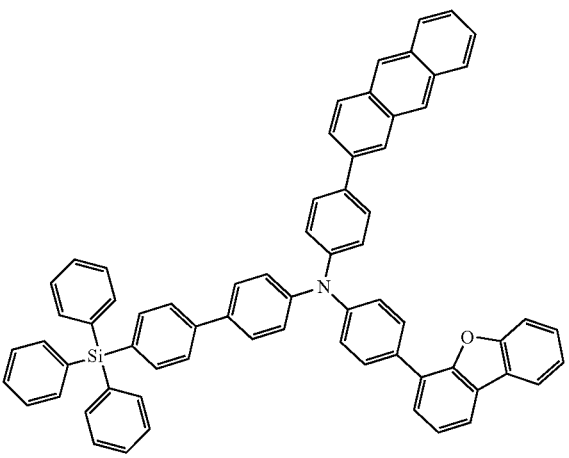
C519
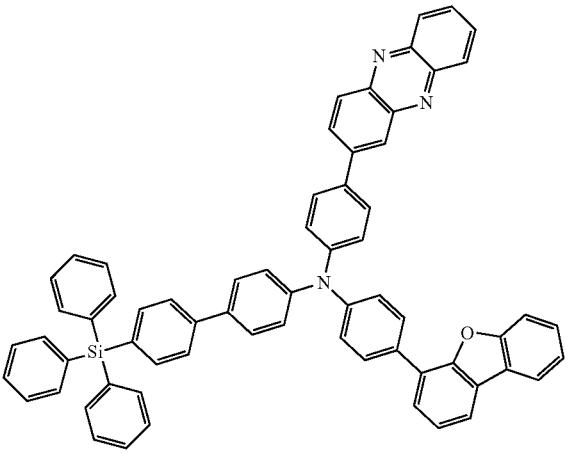

C520
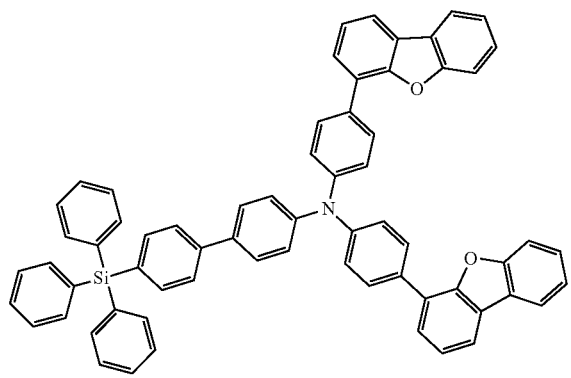
C521
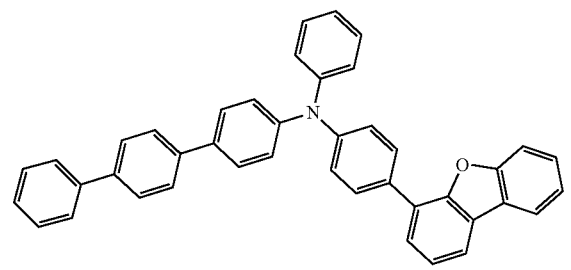
C522
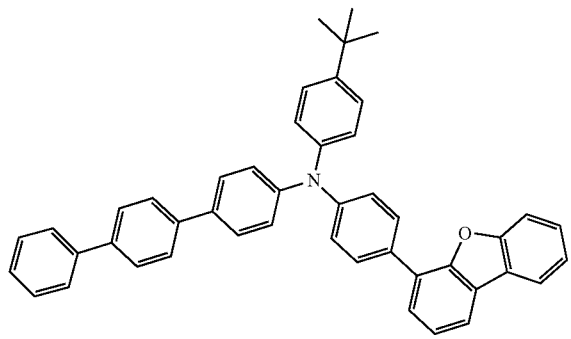
C523
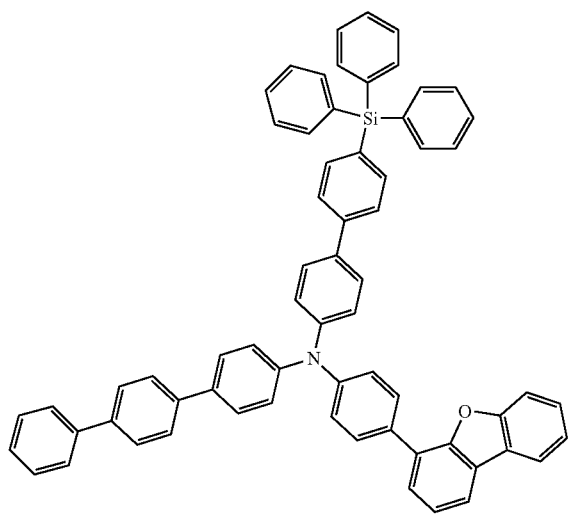
C524
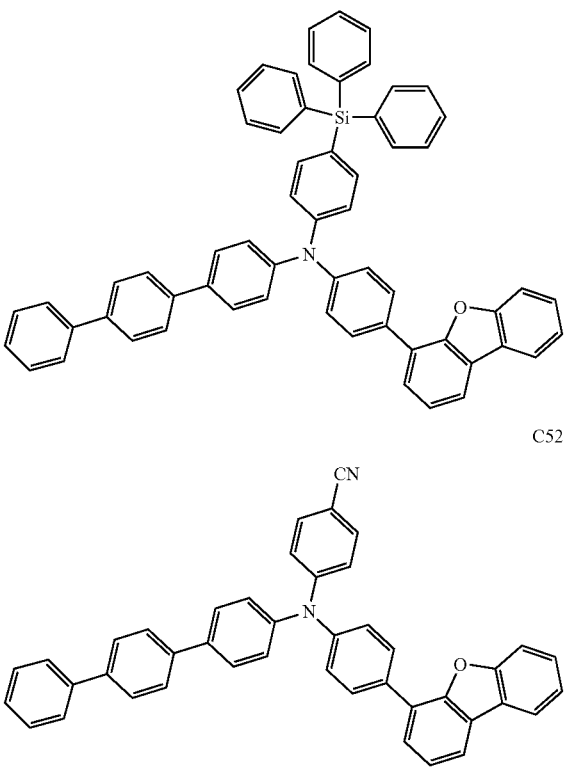
C525
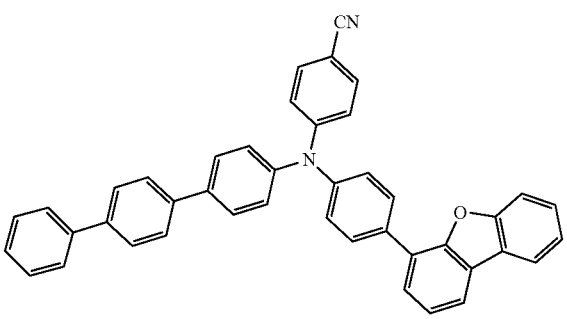
C526
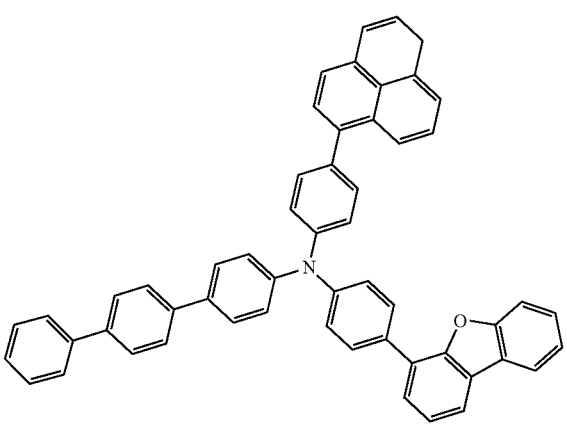
C527
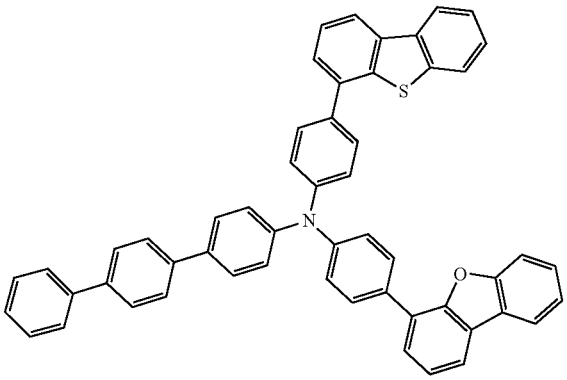

C528
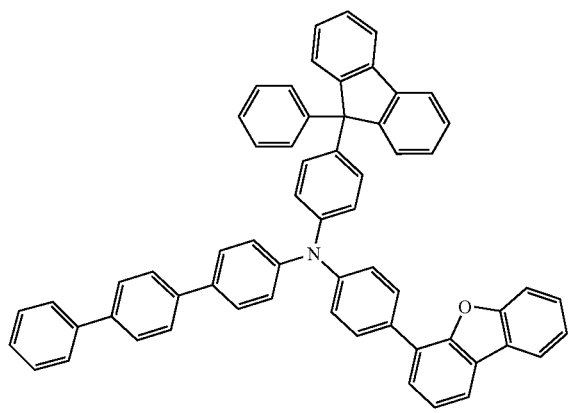
C529
C532
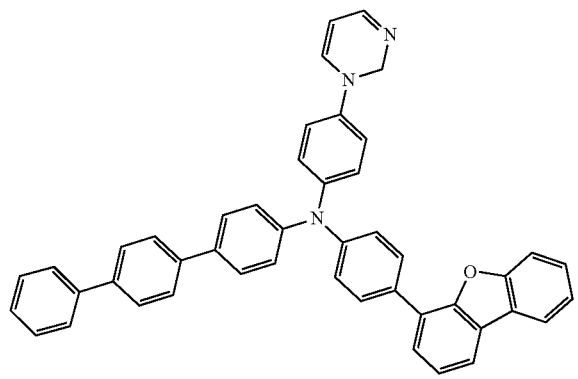
C533
C530
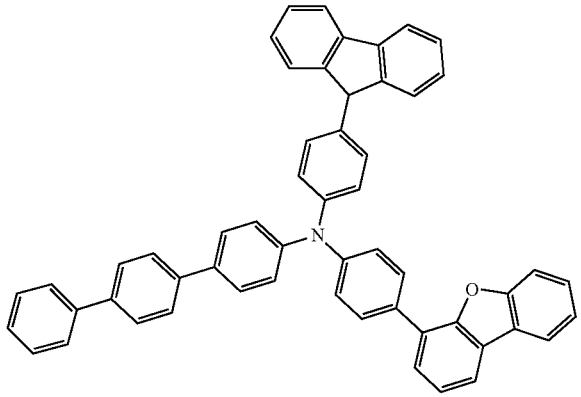
C534
C531
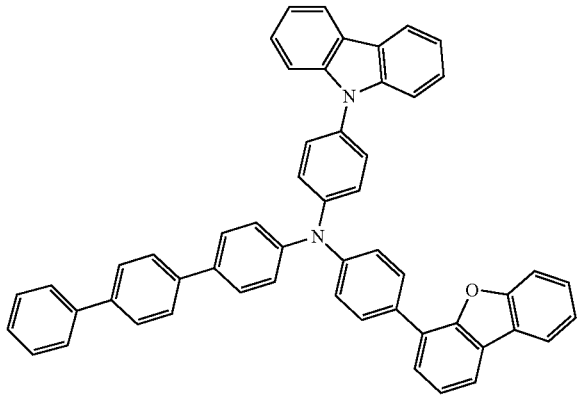
C535
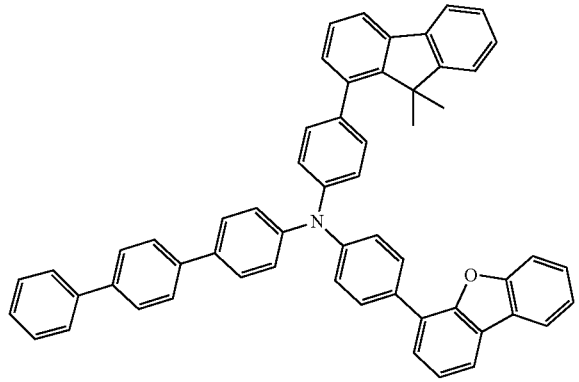

C536
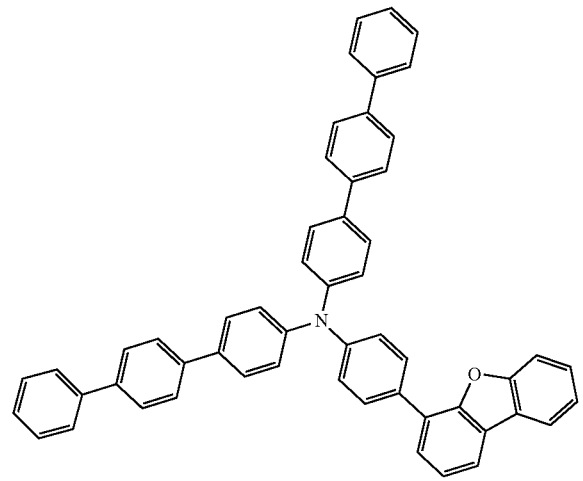
C539
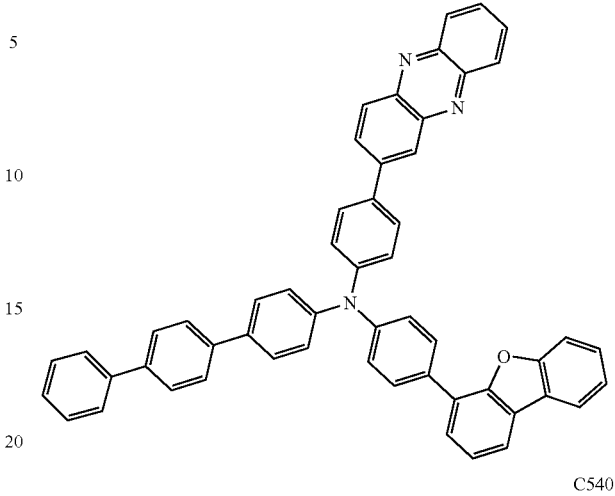
C537
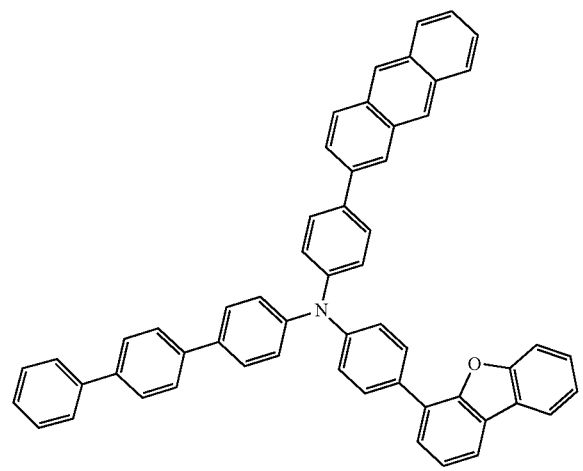
C540
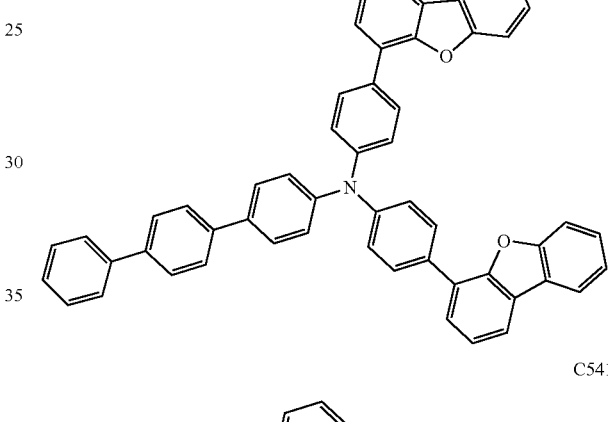
C541
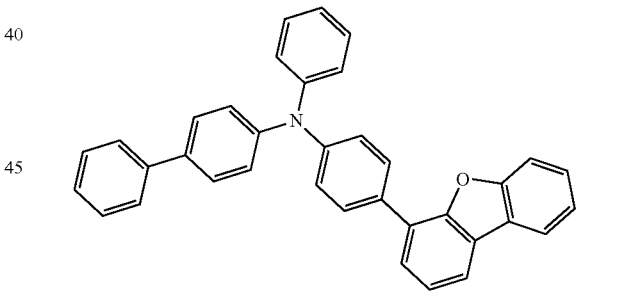
C538
C542
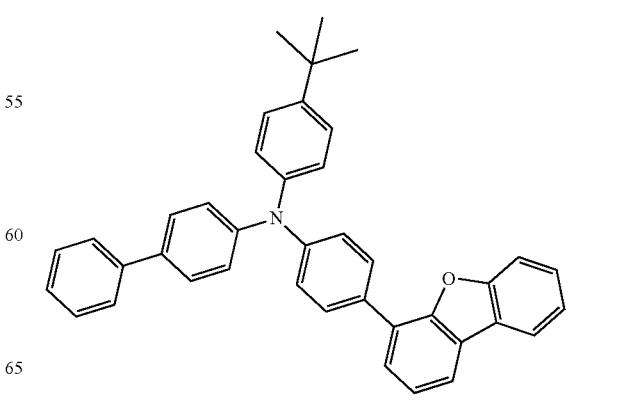

C543
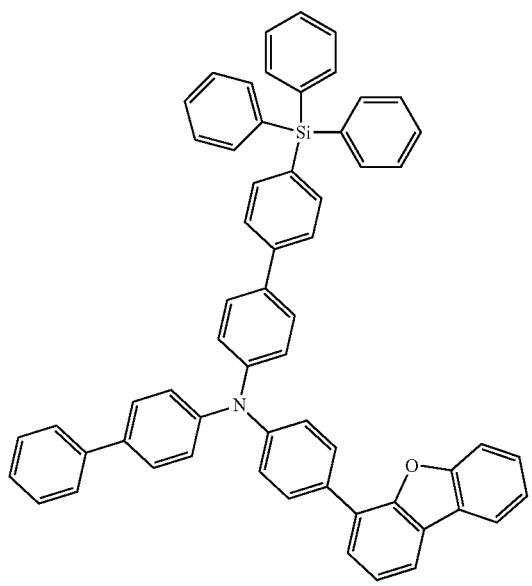
C544
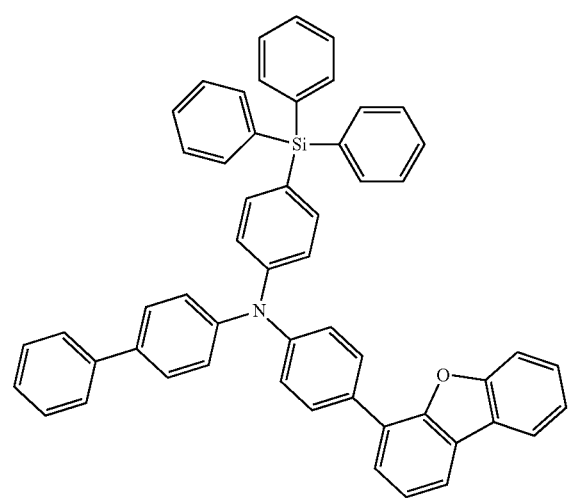
C545
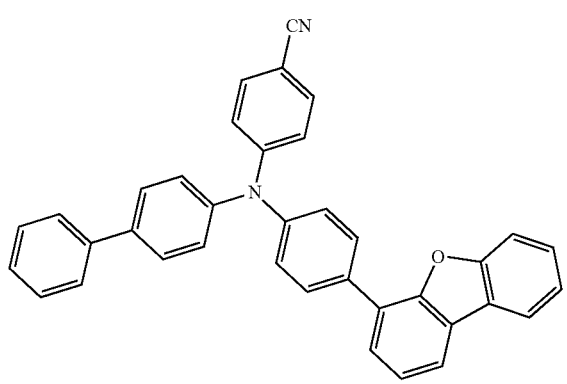
C546
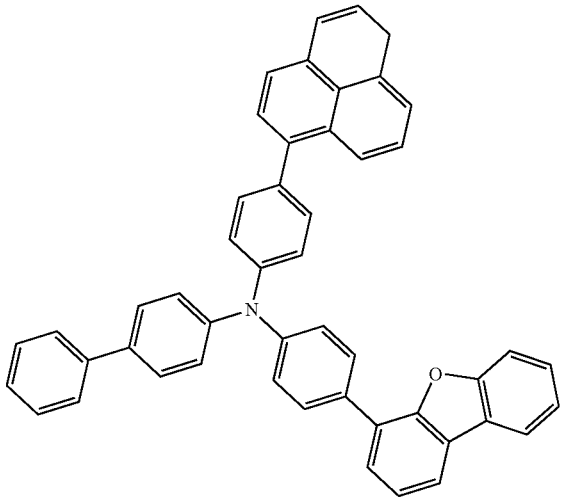
C547
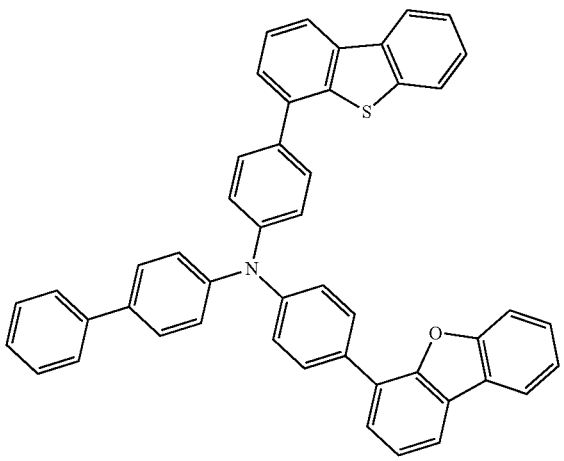
C548
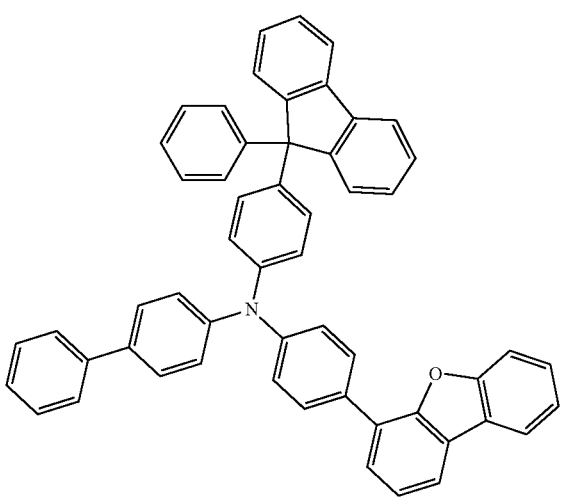

C549
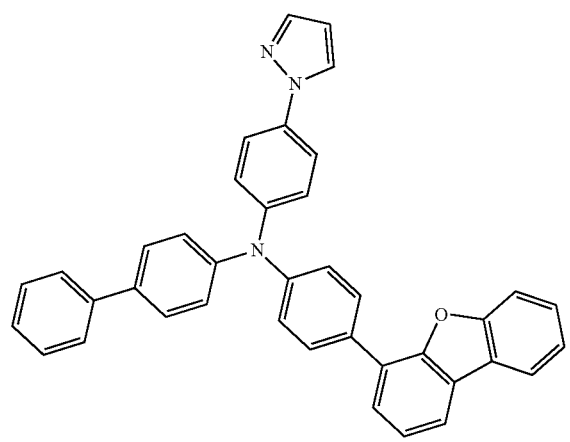
C550
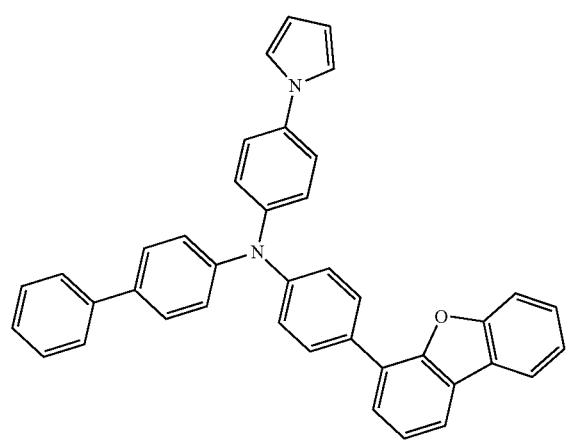
C551
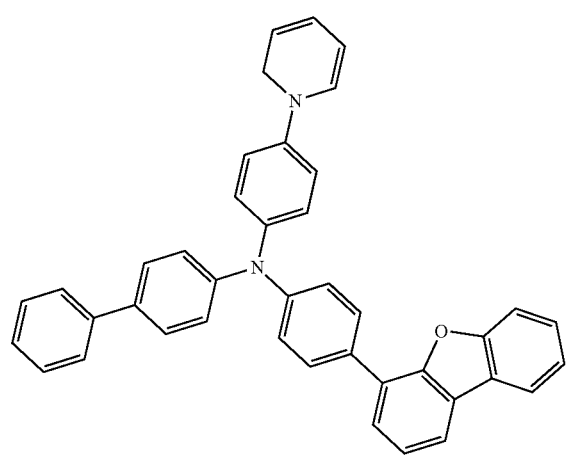
C552
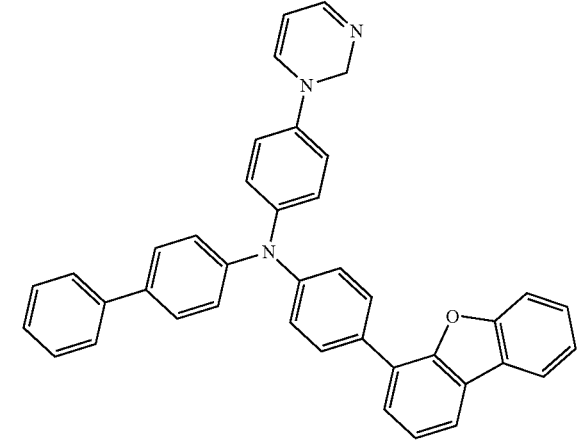
C553
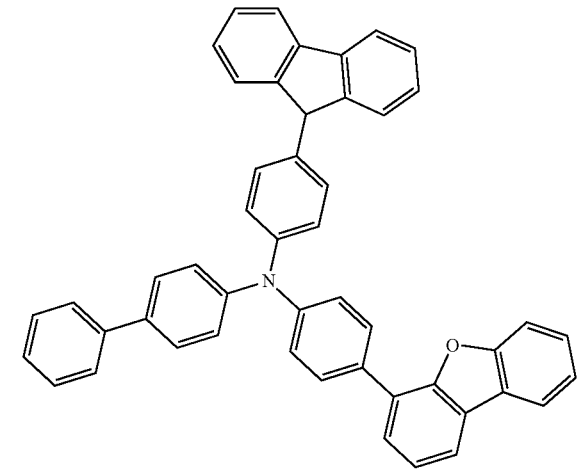
C554
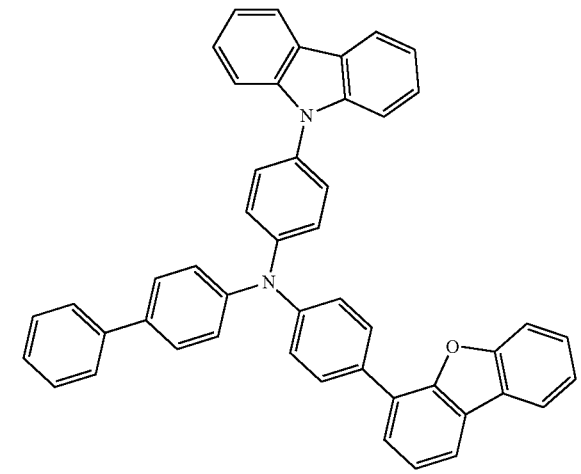

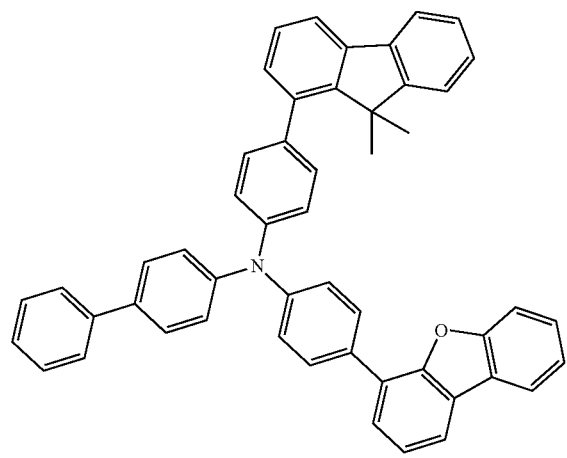
C555
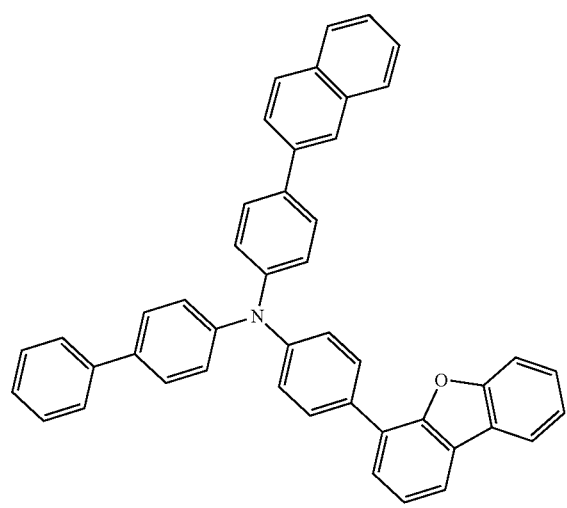
C556
C557
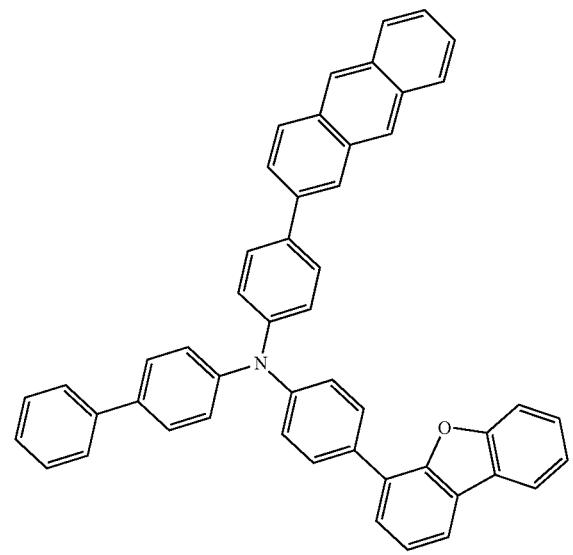
C558
C559
C560

Hereinafter, each component of the organic light-emitting device 10 according to one embodiment of present disclosure will be described as follows.

First Electrode 110

In the drawing, a substrate may be additionally positioned under the first electrode 110 or above the second electrode 190. The substrate may be a glass substrate or a plastic substrate, each having excellent mechanical strength, thermal stability, transparency, surface smoothness, ease of handling, and/or water resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure or a multi-layered structure including two or more layers. For example, the first electrode 110 may have a three-layered structure of ITO/Ag/ITO, but the structure of the first electrode 110 is not limited thereto.

Organic Layer

An organic layer may be located on the first electrode 110. The organic layer may include the emission layer 150 and a hole transport region located between the first electrode 110 and the emission layer 150.

The organic layer may further include an electron transport region between the emission layer 150 and the second electrode 190.

Hole Transport Region in Organic Layer

The hole transport region may include the first hole transport stack 120, the second hole transport stack 130, and the electron blocking layer 140. The hole transport region may further include an emission auxiliary layer.

For example, the hole transport region may have the multi-layered structure of the first hole injection layer 121/first hole transport layer 122/second hole injection layer 131/second hole transport layer 132/electron blocking layer 140, which are sequentially stacked from the first electrode 110, but embodiments of the present disclosure are not limited thereto.

The hole transport region may include at least one selected from m-MTDATA, TDATA, 2-TNATA, NPB (NPD), β-NPB, TPD, spiro-TPD, spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), compounds represented by Formulae 1-1 to 1-4, 2 and 5, a compound represented by Formula 201, and a compound represented by Formula 202:

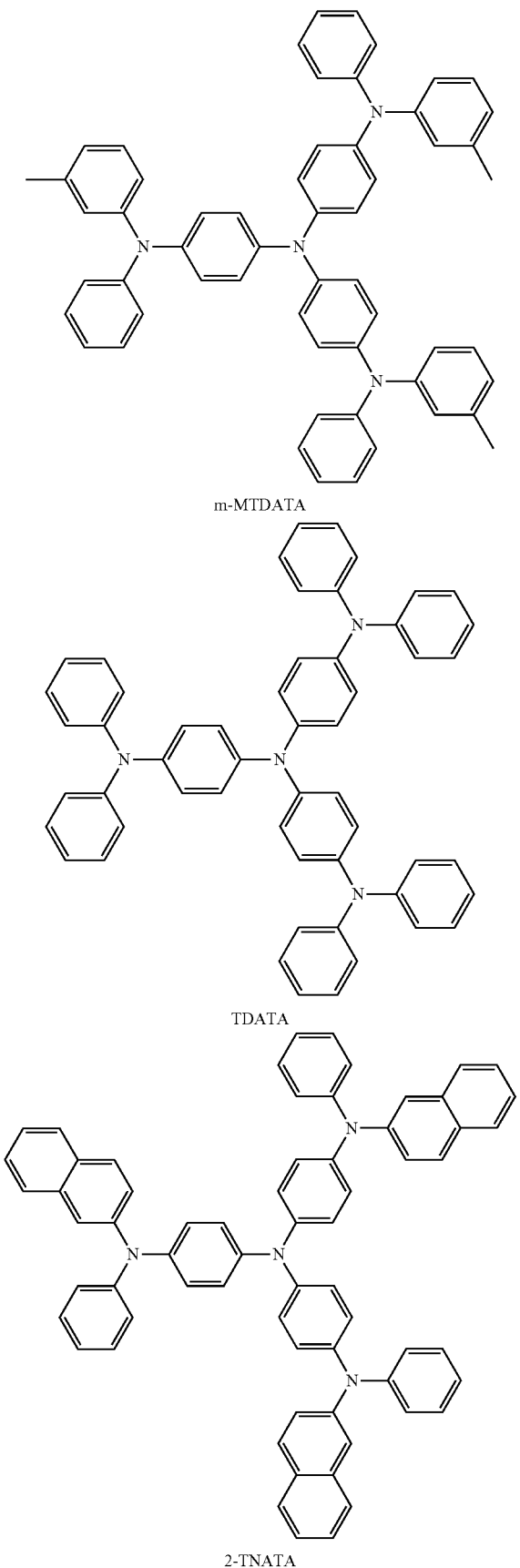

-continued

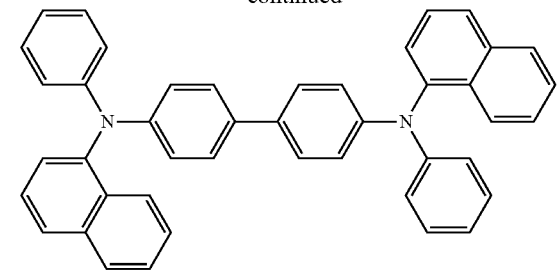

NPB

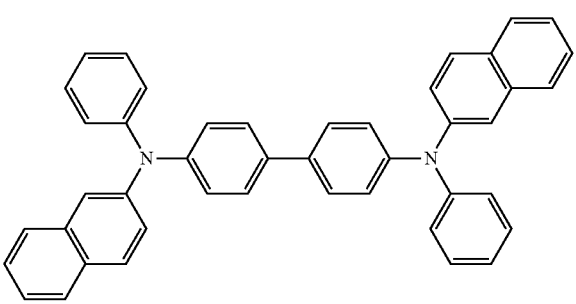

β-NPB

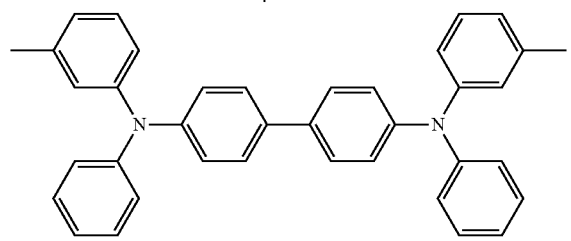

TPD

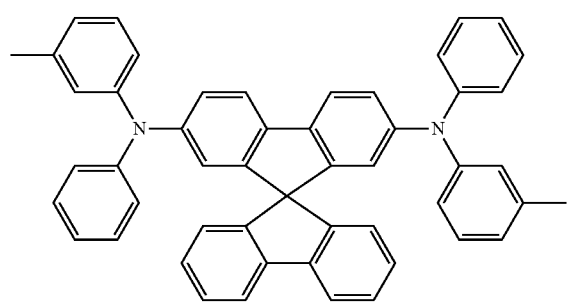

Spiro-TPD

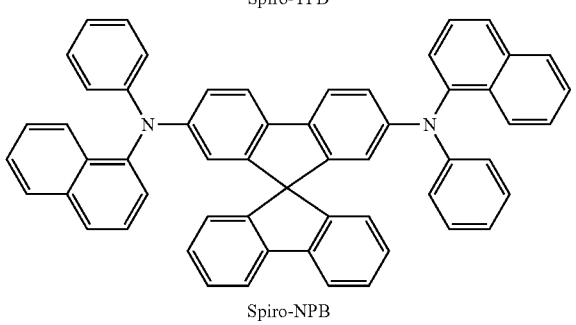

Spiro-NPB

-continued

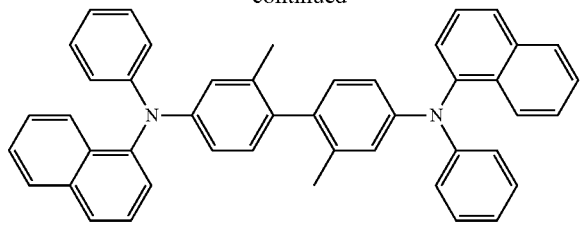

methylated NPB

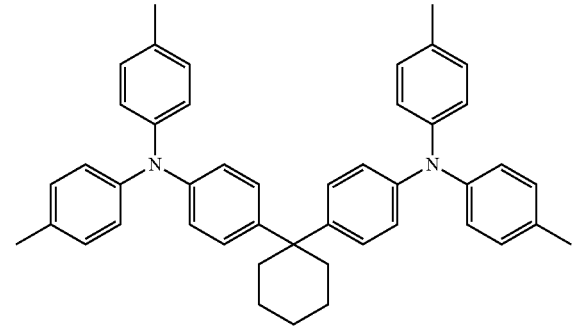

Spiro-TPD

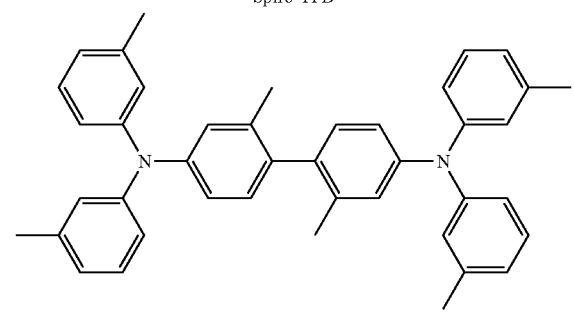

HMTPD

Formula 201

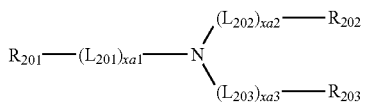

Formula 202

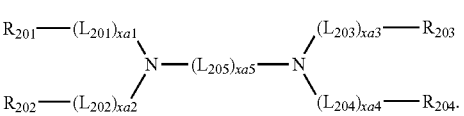

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked to each other via a single bond, a dimethyl-methylene group, or a diphenyl-methylene group, and $R_{203}$ and $R_{204}$ may optionally be linked to each other via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$) and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from: a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$) and —N($Q_{31}$)($Q_{32}$), wherein $Q_{31}$ to $Q_{33}$ are the same as described above.

In one or more embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked to each other via a single bond, and/or ii) $R_{203}$ and $R_{204}$ may be linked to each other via a single bond.

In one or more embodiments, $R_{201}$ to $R_{204}$ in Formula 202 may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201-1 below:

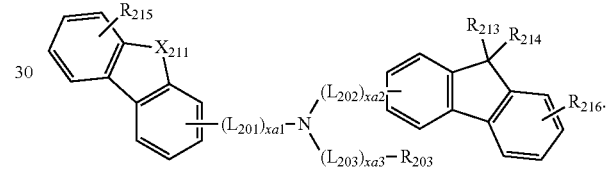

Formula 201-1

In one embodiment, the compound represented by Formula 201 may be represented by Formula 201-2 below, but embodiments of the present disclosure are not limited thereto:

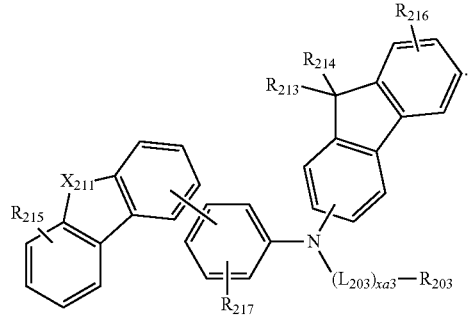

Formula 201-2

In one or more embodiments, the compound represented by Formula 201 may be represented by Formula 201-2(1) below, but embodiments of the present disclosure are not limited thereto:

Formula 201-2(1)

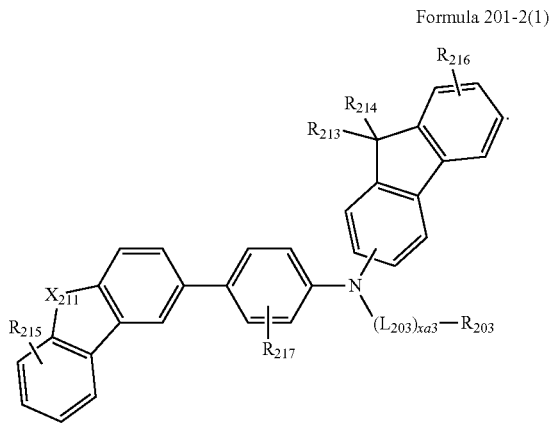

In one or more embodiments, the compound represented by Formula 201 may be represented by Formula 201A below:

Formula 201A

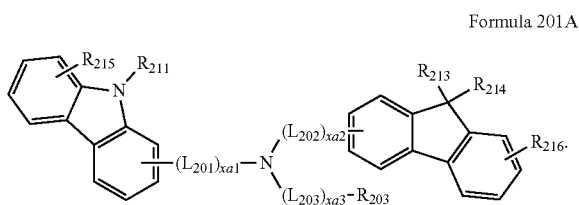

In one or more embodiments, the compound represented by Formula 201 may be represented by Formula 201A(1) below, but embodiments of the present disclosure are not limited thereto:

Formula 201A(1)

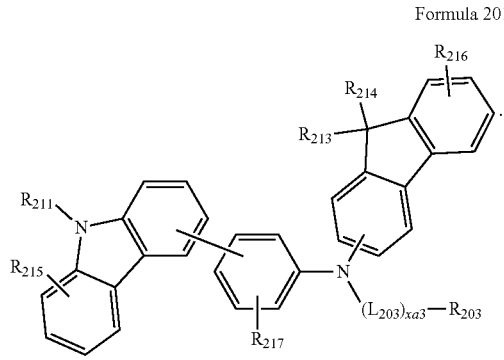

In one or more embodiments, the compound represented by Formula 201 may be represented by Formula 201A-1 below, but embodiments of the present disclosure are not limited thereto:

Formula 201A-1

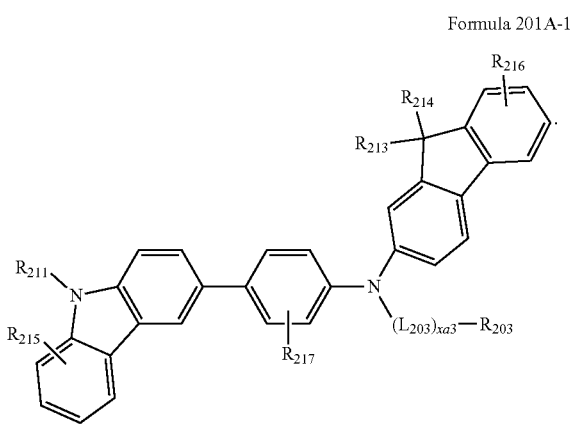

In one or more embodiments, the compound represented by Formula 202 may be represented by Formula 202-1 below:

Formula 202-1

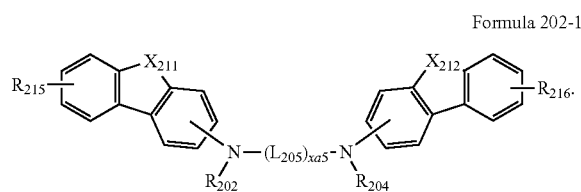

In one or more embodiments, the compound represented by Formula 202 may be represented by Formula 202-1(1) below:

Formula 202-1(1)

In one embodiment, the compound represented by Formula 202 may be represented by Formula 202A below:

Formula 202A

In one or more embodiments, the compound represented by Formula 202 may be represented by Formula 202A-1 below:

Formula 202A-1

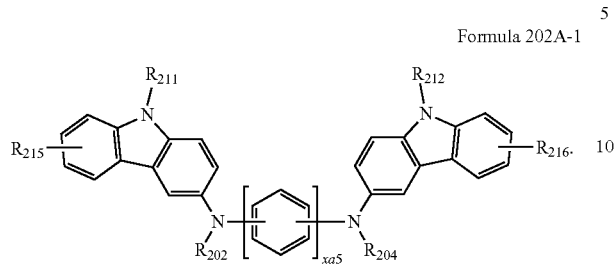

In Formulae 201-1, 201-2, 201-2(1), 201A, 201A(1), 201A-1, 202-1, 202-1(1), 202A, and 202A-1, $L_{201}$ to $L_{203}$, xa1 to xa3, xa5, and $R_{202}$ to $R_{204}$ are the same as described above, $L_{205}$ may be selected from a phenylene group, and a fluorenylene group, $X_{211}$ may be selected from O, S, and $N(R_{211})$, $X_{212}$ may be selected from O, S, and $N(R_{212})$, $R_{211}$ and $R_{212}$ are the same as described in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT48, but embodiments of the present disclosure are not limited thereto:

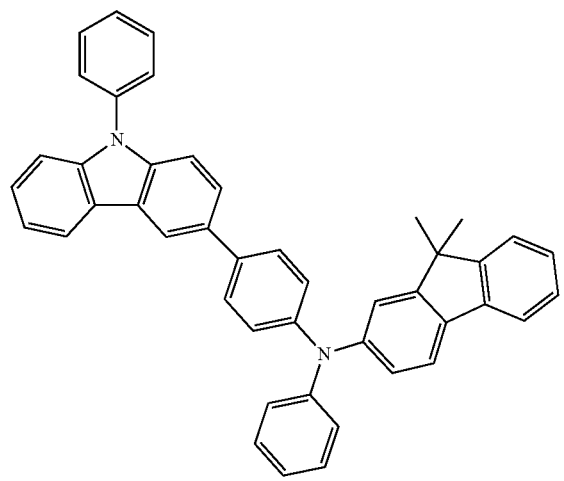

HT1

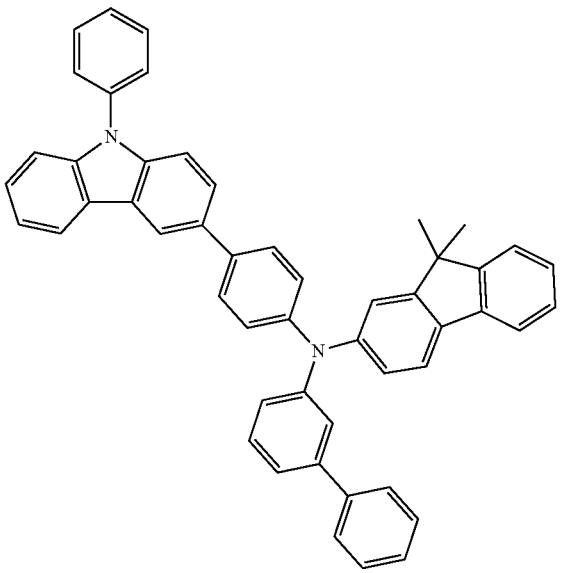

HT2

-continued
HT3
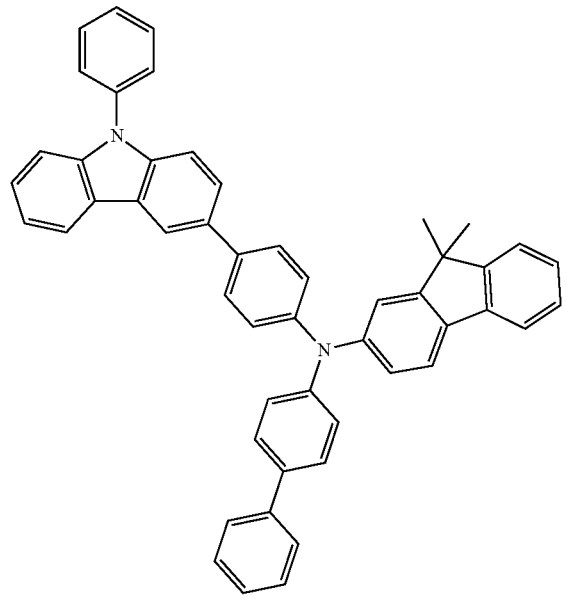
HT4
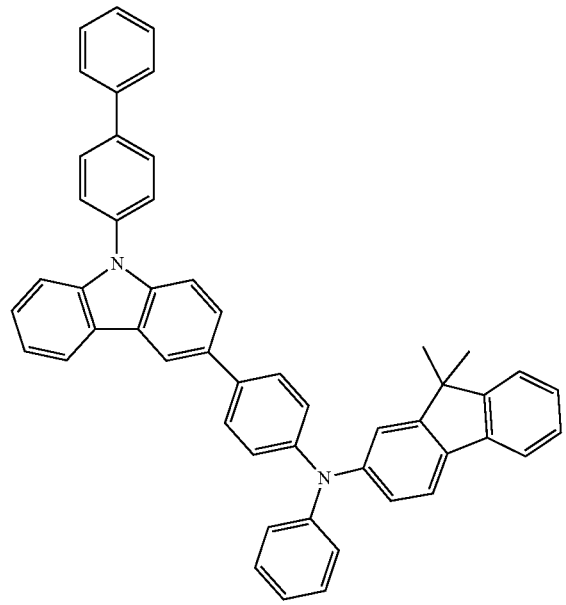
HT5
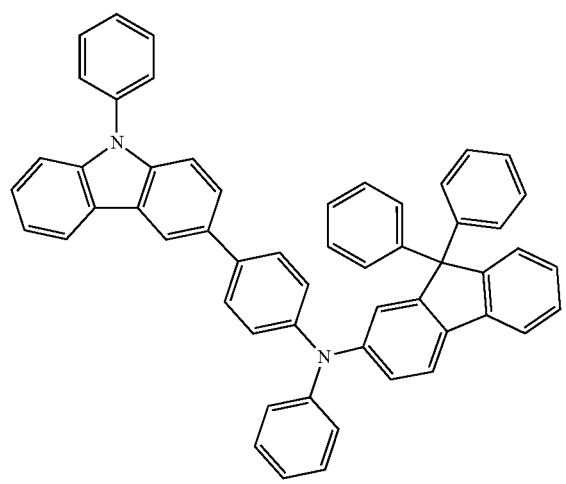
HT6
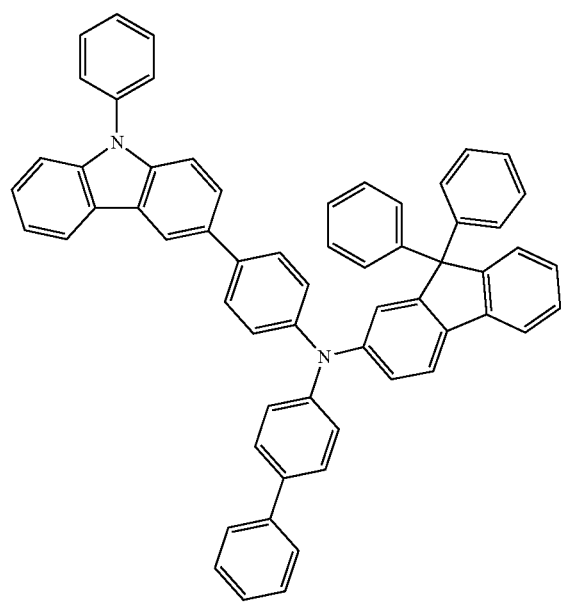

-continued
HT7
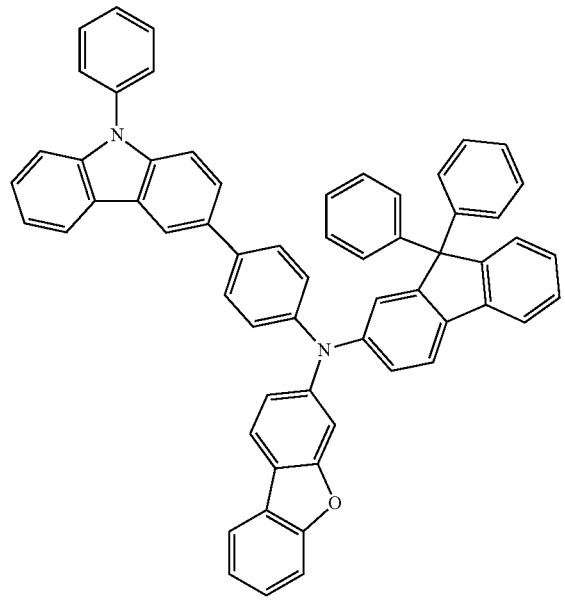
HT8
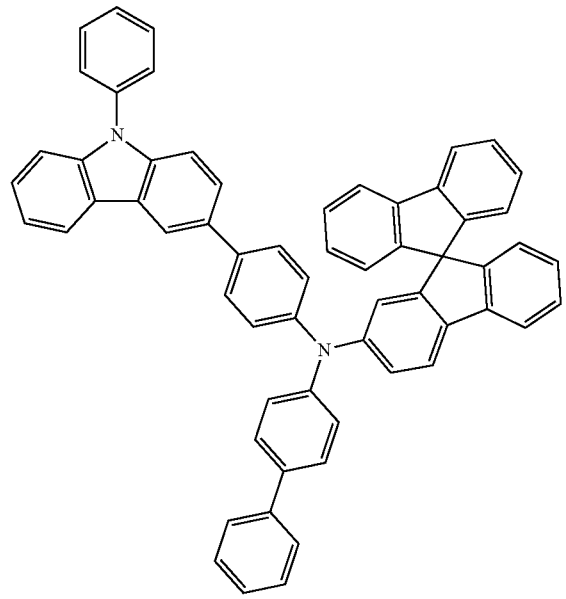
HT9
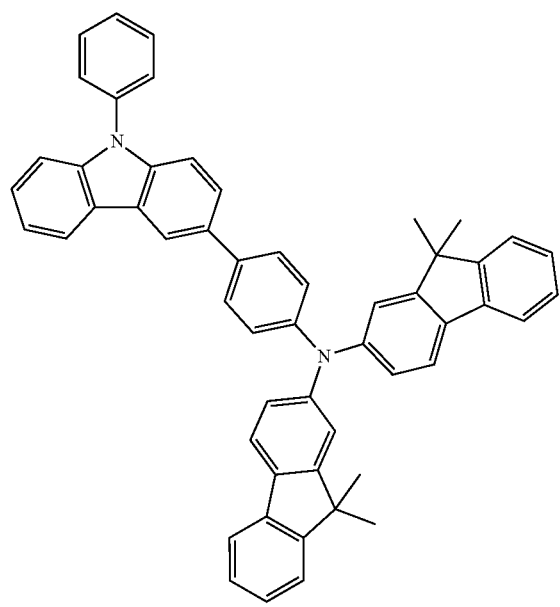
HT10
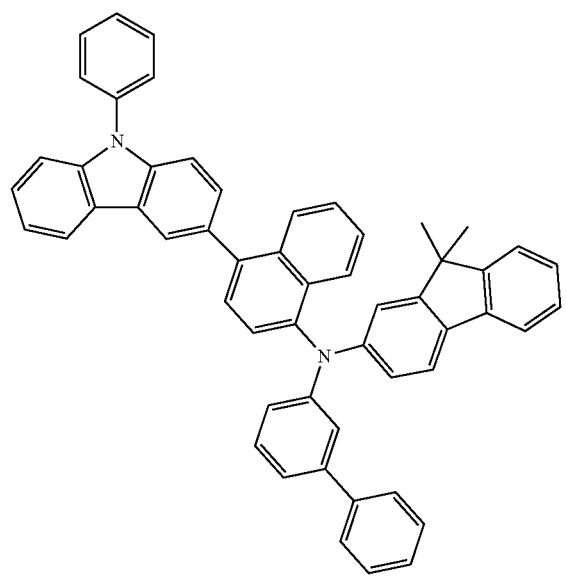

-continued
HT11
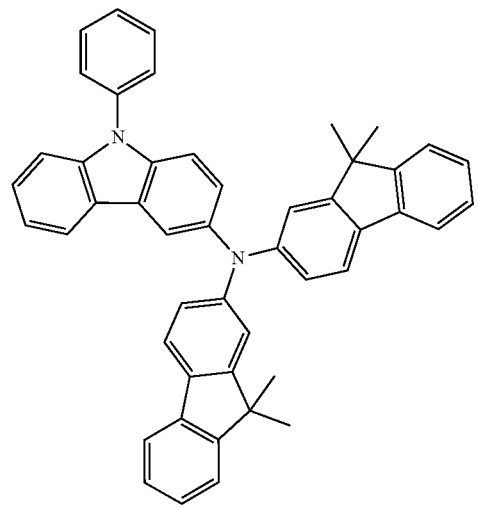
HT12
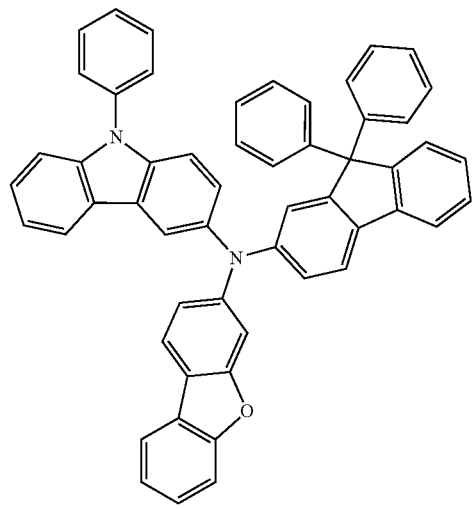
HT13
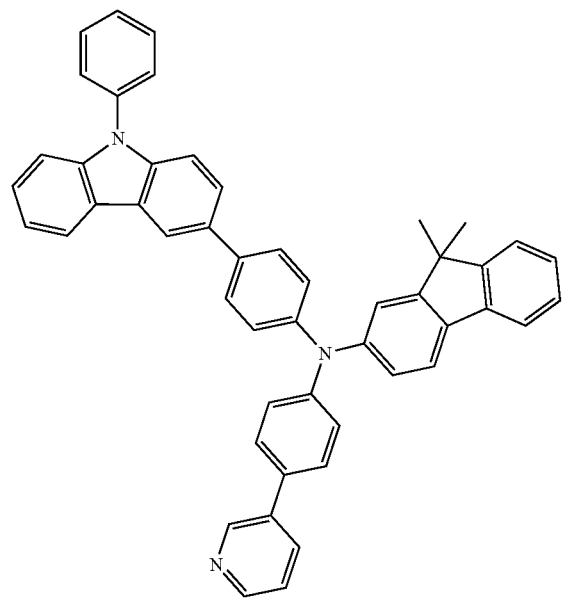
HT14
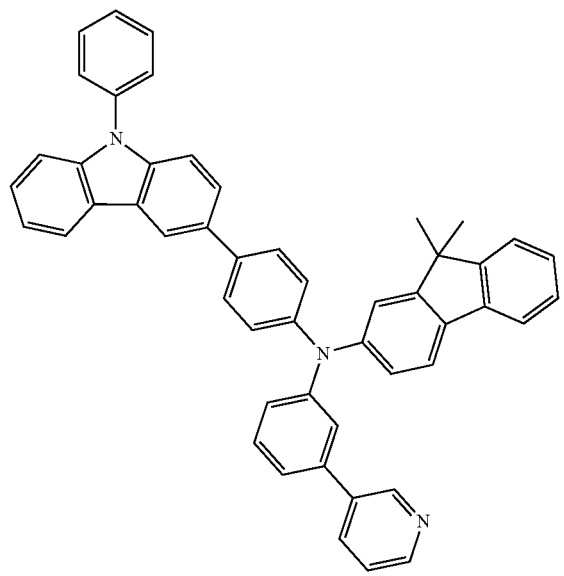
HT15
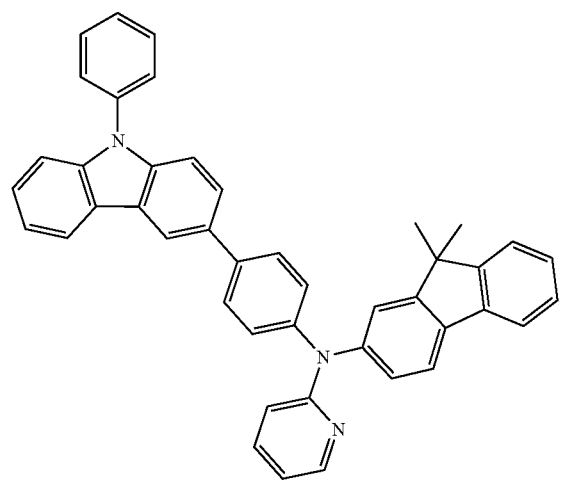
HT16
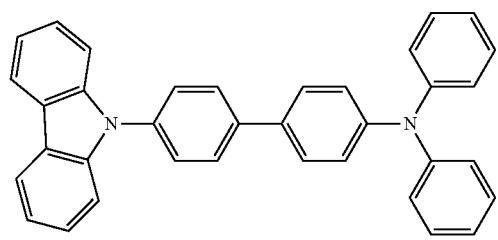

HT17
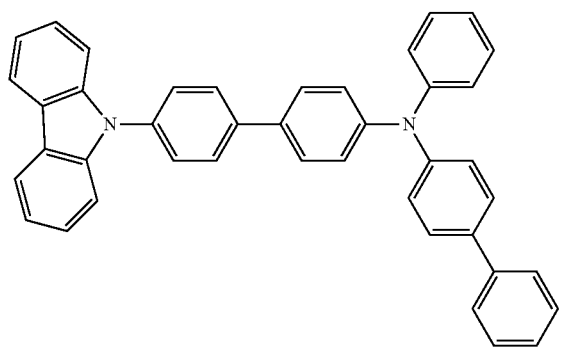
HT18
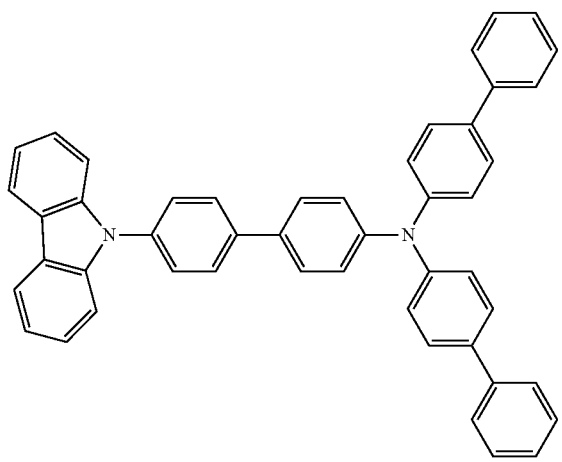
HT19
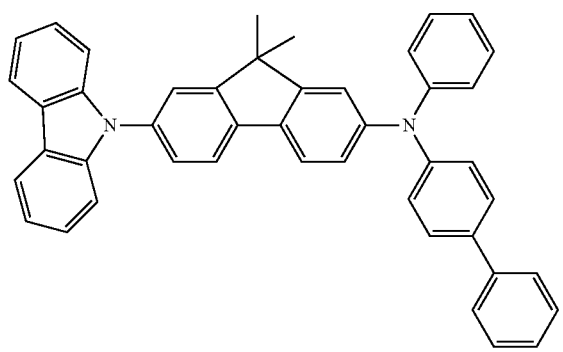
HT20
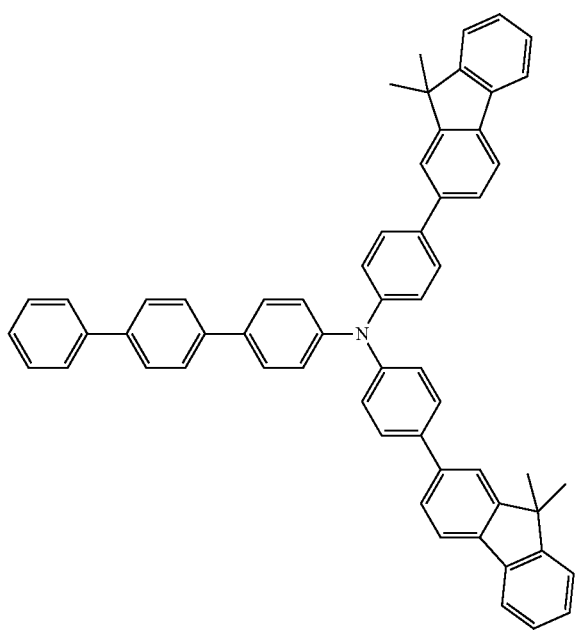

HT21
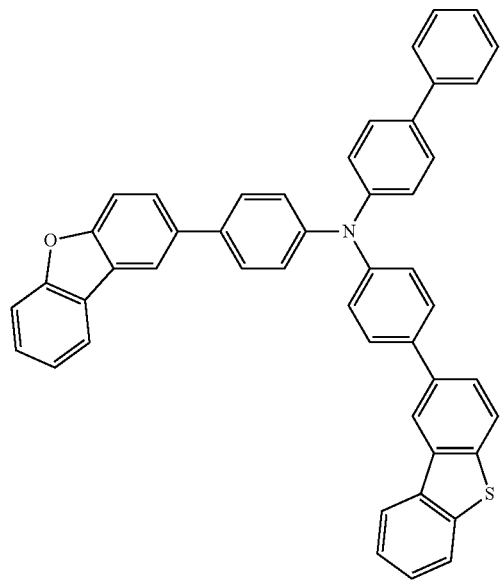
HT22
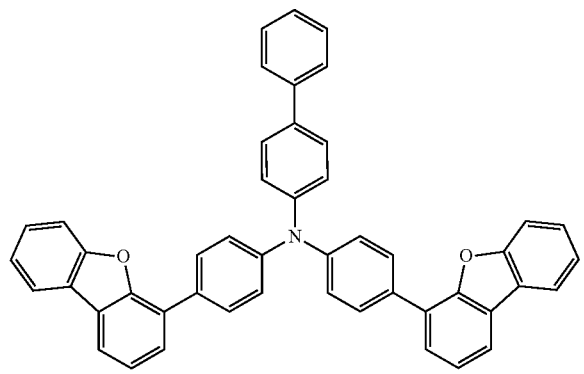
HT23
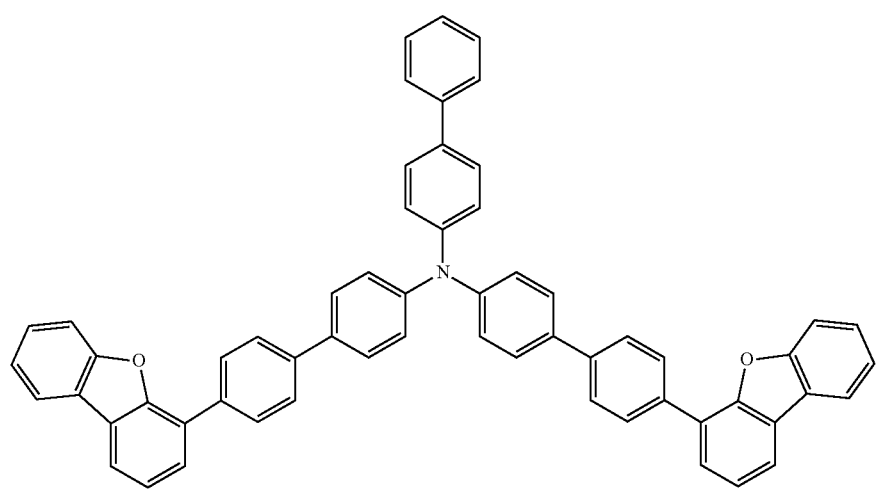

HT24
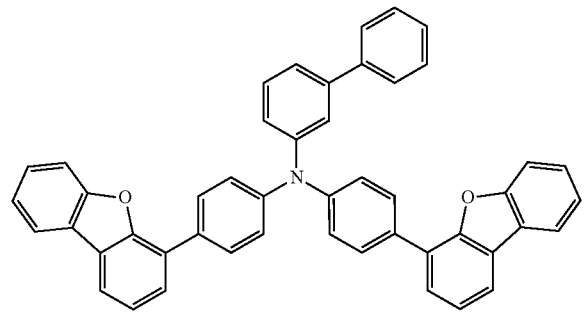
HT25
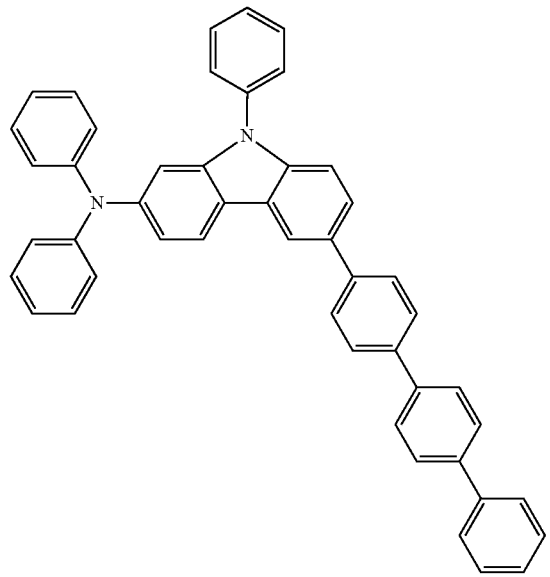
HT26
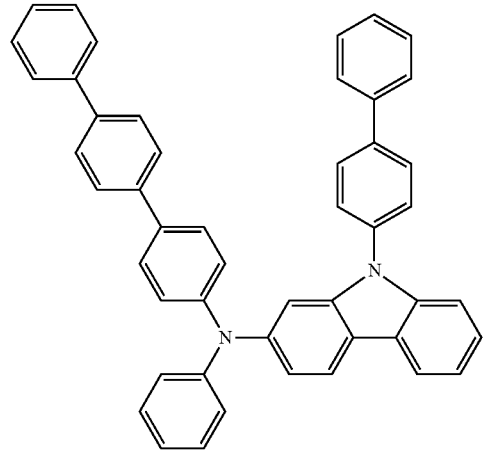
HT27
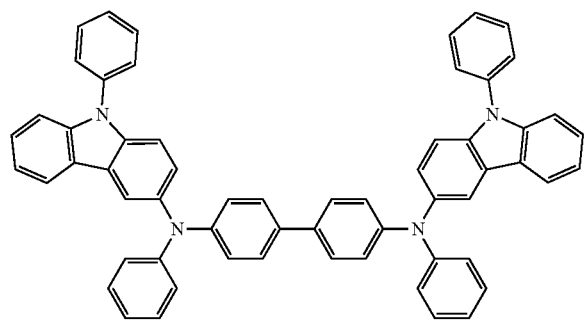
HT28
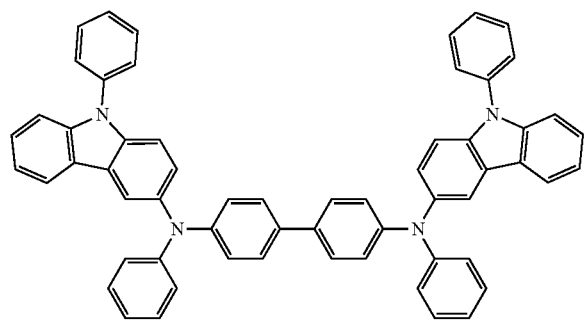
HT29
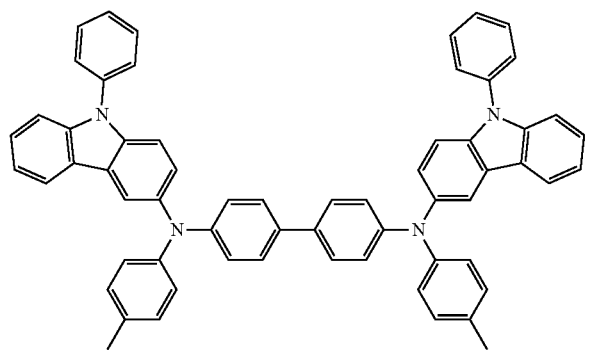

-continued
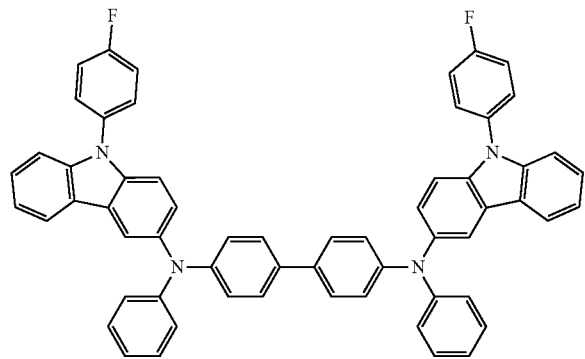
HT30
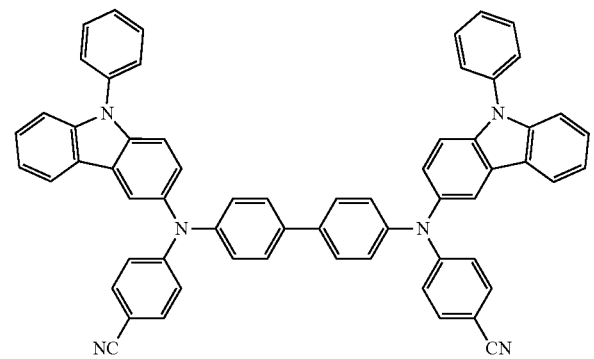
HT31
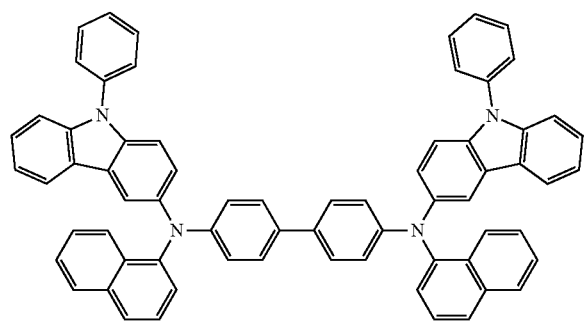
HT32
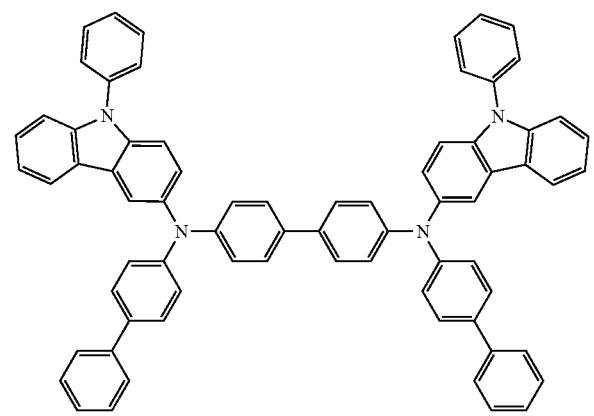
HT33
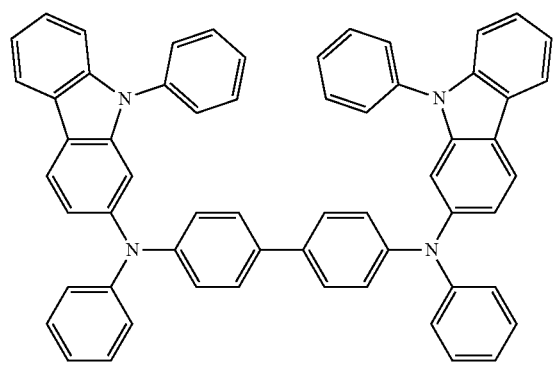
HT34
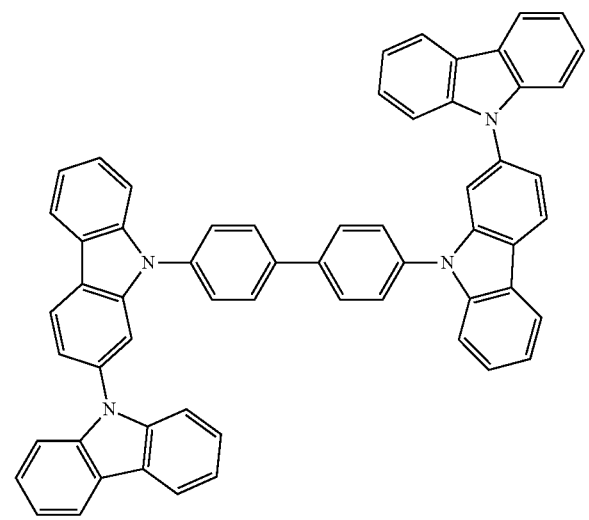
HT35

-continued
HT36
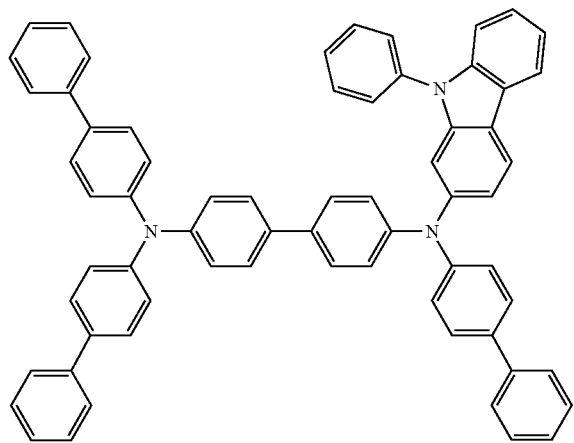
HT37
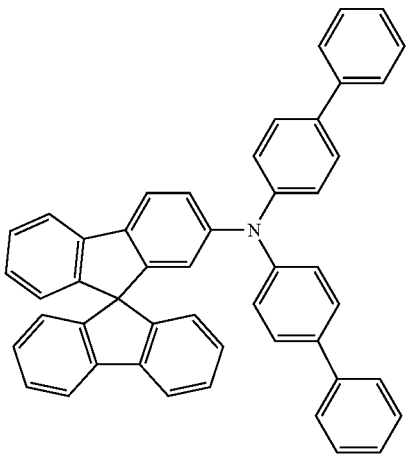
HT38
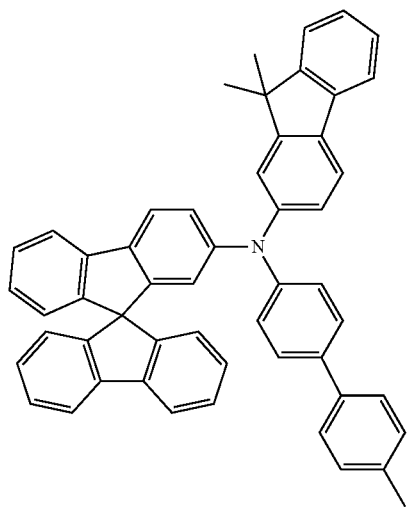
HT39
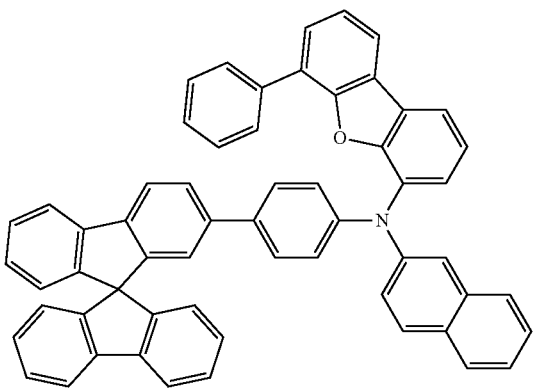
HT40
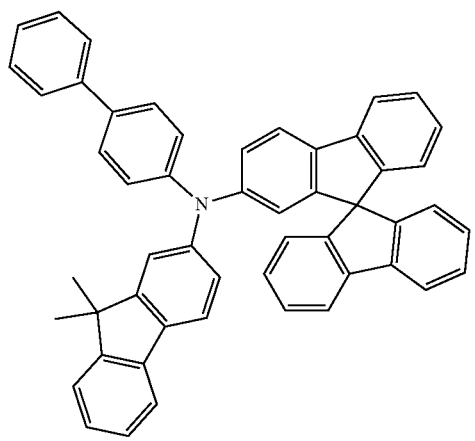
HT41
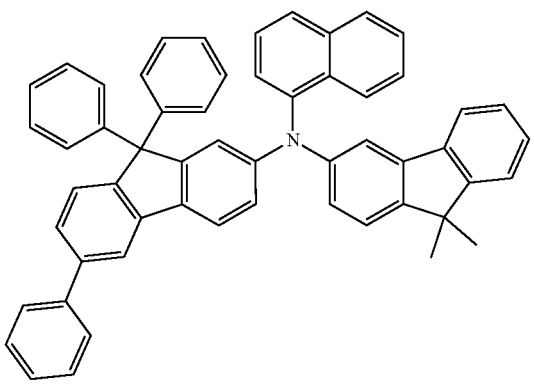

HT42
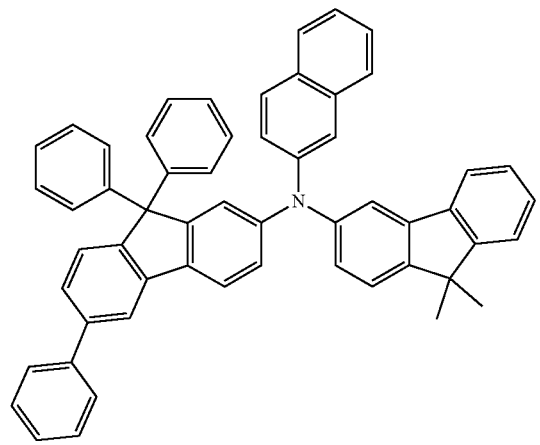
HT43
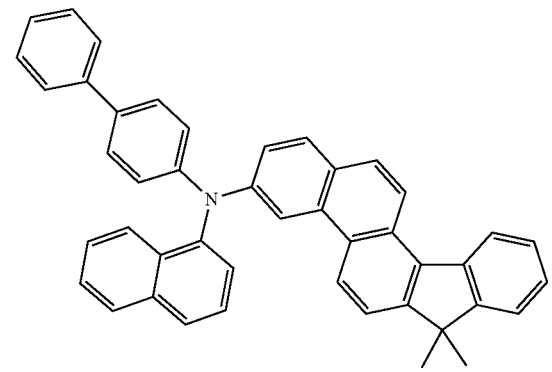
HT44
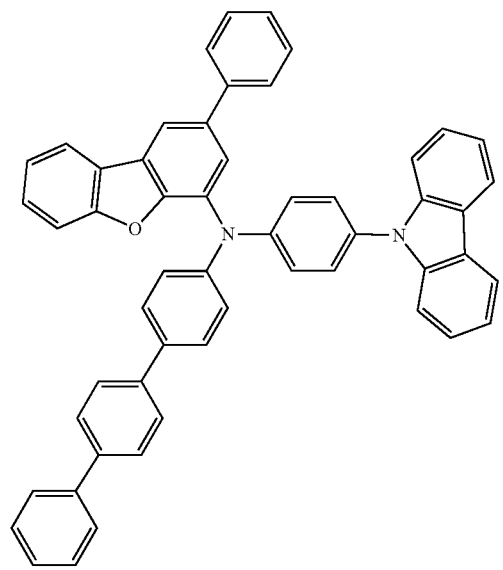
HT45
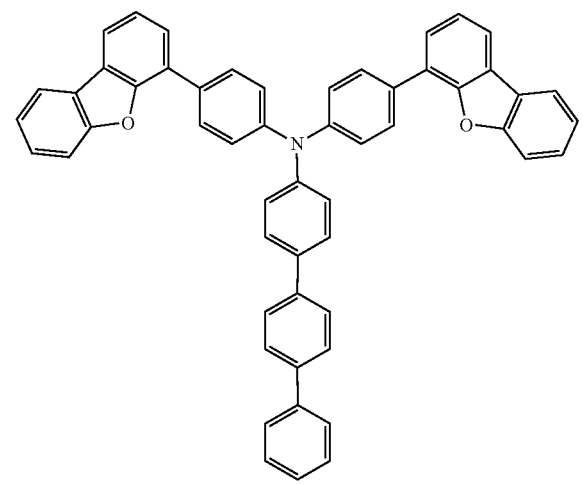
HT46
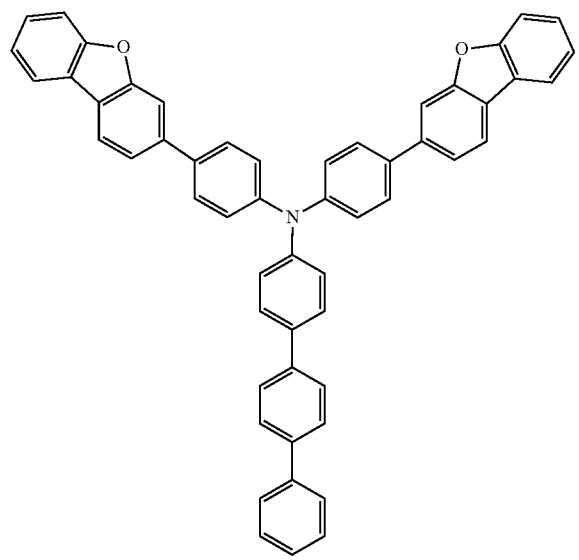
HT47
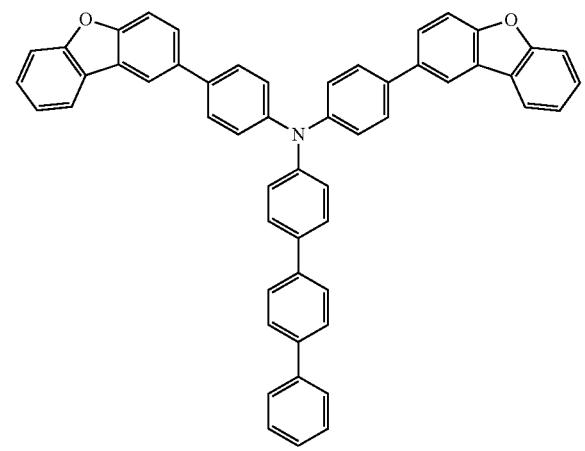

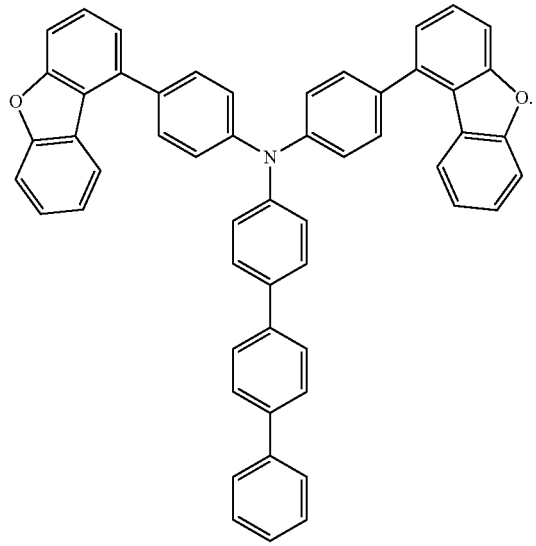
HT48

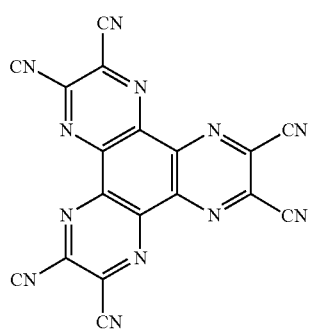
HAT-CN

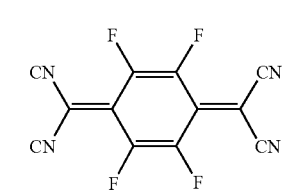
F4-TCNQ

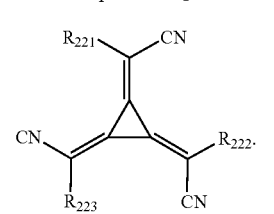
Formula 221

A thickness of the hole transport region may be in a range of about 100 Å to about 10,000 Å, for example, about 100 Å to about 1,000 Å. When the thickness of the hole transport region is within the range described above, satisfactory (or improved) hole transportation characteristics may be obtained without a substantial increase in driving voltage.

The emission auxiliary layer may increase light-emission efficiency by compensating for an optical resonance distance according to the wavelength of light emitted by an emission layer, and the electron blocking layer 140 may block or reduce the flow of electrons from an electron transport region. The emission auxiliary layer and the electron blocking layer 140 may each independently include any of the materials as described above.

P-Dopant

The hole transport region may further include, in addition to the materials described above, a charge-generation material for improvement of conductive properties. The charge-generation material may be homogeneously or non-homogeneously dispersed in the hole transport region.

The charge-generation material may be, for example, a p-dopant.

In one embodiment, a lowest unoccupied molecular orbital (LUMO) energy level of the p-dopant may be −3.5 eV or less.

The p-dopant may include at least one selected from a quinone derivative, a metal oxide, and a cyano group-containing compound, but embodiments of the present disclosure are not limited thereto.

In one embodiment, the p-dopant may include at least one selected from:
 a quinone derivative, such as tetracyanoquinodimethane (TCNQ) and/or 2,3,5,6-tetrafluoro-7,7,8,8-tetracyano-quinodimethane (F4-TCNQ);
 a metal oxide, such as tungsten oxide and/or molybdenum oxide;
 1,4,5,8,9,12-hexaazatriphenylene-hexacarbonitrile (HAT-CN); and
 a compound represented by Formula 221 below,
but embodiments of the present disclosure are not limited thereto:

In Formula 221,
$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer 150 in Organic Layer

When the organic light-emitting device 10 is a full-color organic light-emitting device, the emission layer 155 may be patterned into a red emission layer, a green emission layer, and a blue emission layer, according to a sub-pixel. In one or more embodiments, the emission layer 150 may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a luminescent material. The luminescent material may include at least one selected from a phosphorescent dopant, a fluorescent dopant, and a quantum dot.

The fluorescent dopant may include a delayed fluorescent dopant.

An amount of the dopant in the emission layer 150 may be in a range of about 0.01 parts by weight to about 15 parts by weight based on 100 parts by weight of the host, but embodiments of the present disclosure are not limited thereto.

A thickness of the emission layer 150 may be in a range of about 100 Å to about 1,000 Å, for example, about 200 Å to about 600 Å. When the thickness of the emission layer 150 is within any of these ranges, excellent (or improved) light-emission characteristics may be obtained without a substantial increase in driving voltage.

Host of Emission Layer 150

In one or more embodiments, the host may include a compound represented by Formula 301 below.

Formula 301

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

When xb11 in Formula 301 is two or more, two or more of $Ar_{301}$(s) may be linked via a single bond.

In one or more embodiments, the compound represented by Formula 301 may be represented by one of Formula 301-1 or Formula 301-2:

Formula 301-1

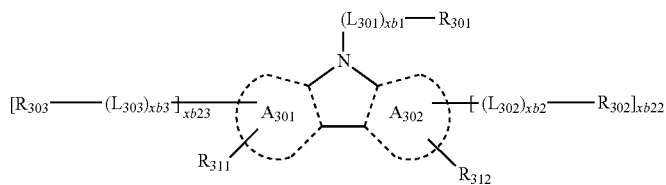

Formula 301-2

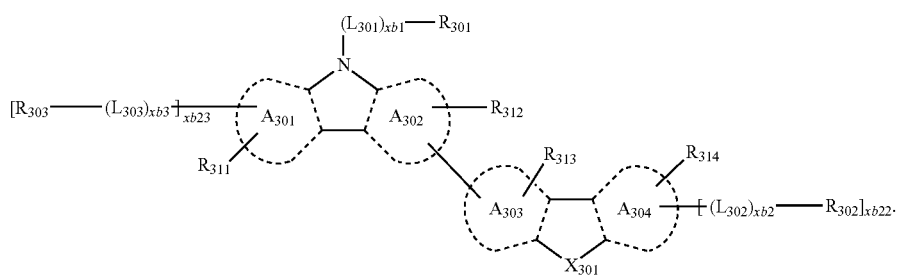

In Formulae 301-1 and 301-2

$A_{301}$ to $A_{304}$ may each independently be selected from a benzene ring, a naphthalene ring, a phenanthrene ring, a fluoranthene ring, a triphenylene ring, a pyrene ring, a chrysene ring, a pyridine ring, a pyrimidine ring, an indene ring, a fluorene ring, a spiro-bifluorene ring, a benzofluorene ring, a dibenzofluorene ring, an indole ring, a carbazole ring, a benzocarbazole ring, a dibenzocarbazole ring, a furan ring, a benzofuran ring, a dibenzofuran ring, a naphthofuran ring, a benzonaphthofuran ring, a dinaphthofuran ring, a thiophene ring, a benzothiophene ring, a dibenzothiophene ring, a naphthothiophene ring, a benzonaphthothiophene ring, and a dinaphthothiophene ring, $X_{301}$ may be O, S, or N-[$(L_{304})_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$ and $Q_{31}$ to $Q_{33}$ are the same as described above, $L_{302}$ to $L_{304}$ may each independently be the same as described in connection with $L_{301}$, xb2 to xb4 may each independently be the same as described in connection with xb1, and $R_{302}$ to $R_{304}$ may each independently be the same as described in connection with $R_{301}$.

For example, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and $Q_{31}$ to $Q_{33}$ are the same as described above.

In one embodiment, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ are the same as described above.

In one or more embodiments, the host may include an alkaline earth metal complex, a Zn complex, or a combination thereof. For example, the host may be selected from a Be complex (for example, Compound H55), an Mg complex, and a Zn complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

H1
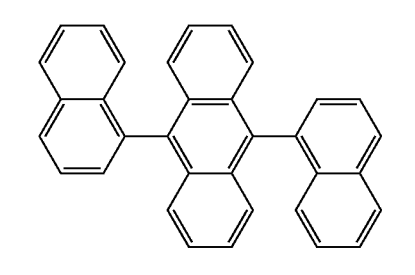

H2
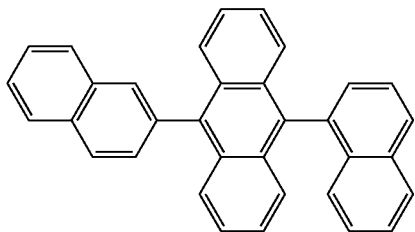

H3
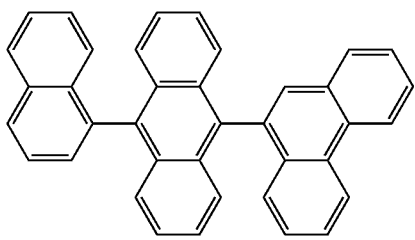

H4
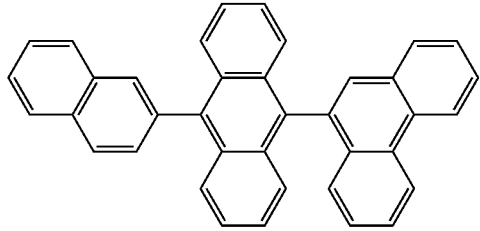

H5
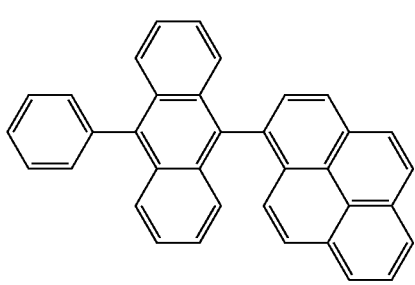

H6
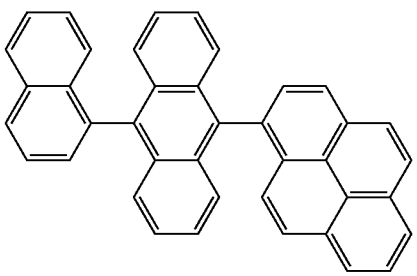

H7
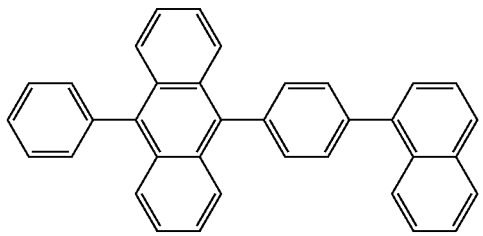

H8
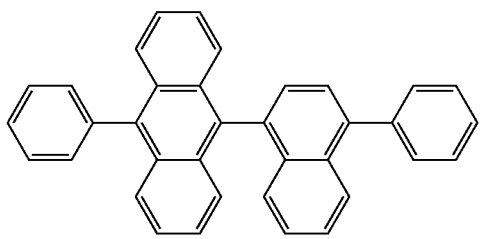

H9
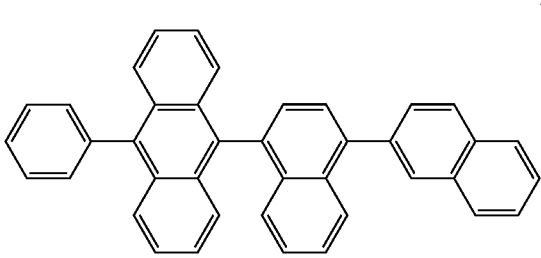

H10
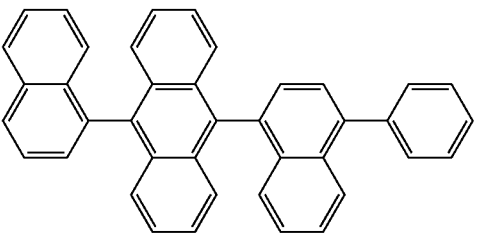

H11
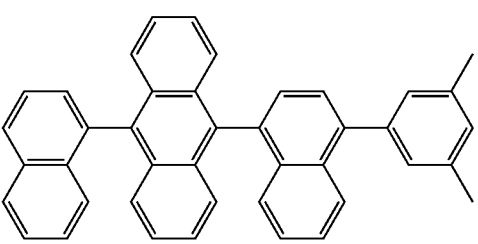

125
-continued
H12
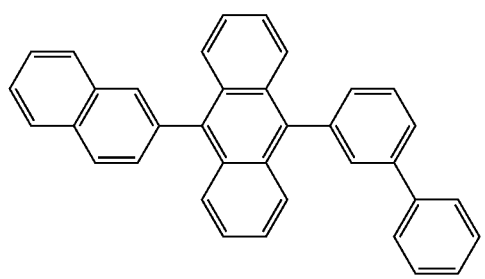
H13
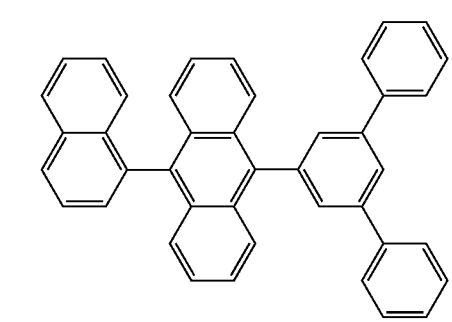
H14
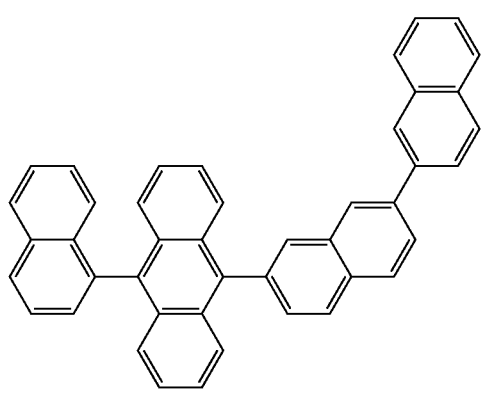
H15
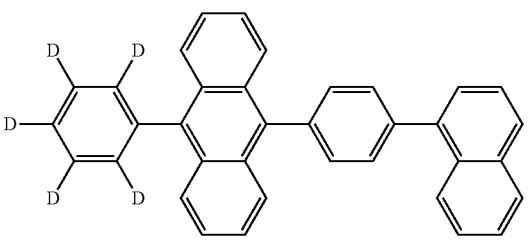
H16
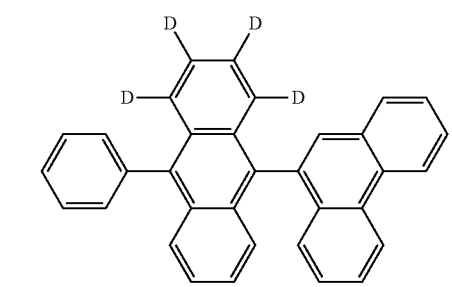
126
-continued
H17
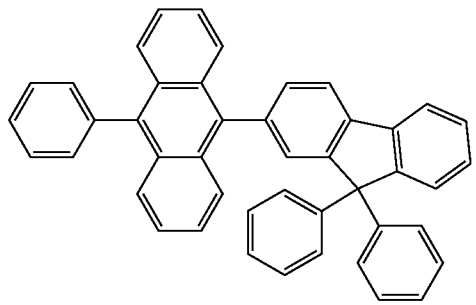
H18
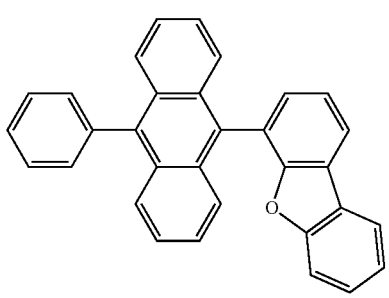
H19
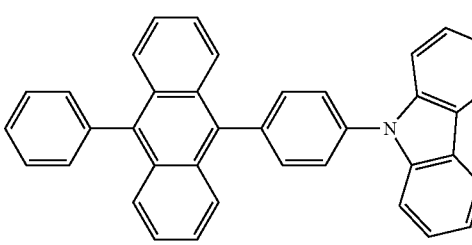
H20
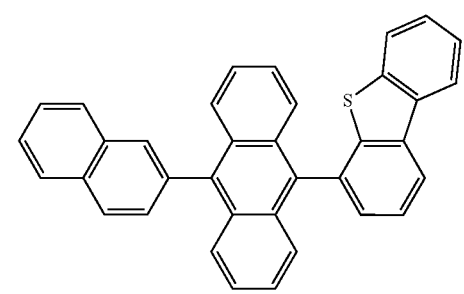
H21
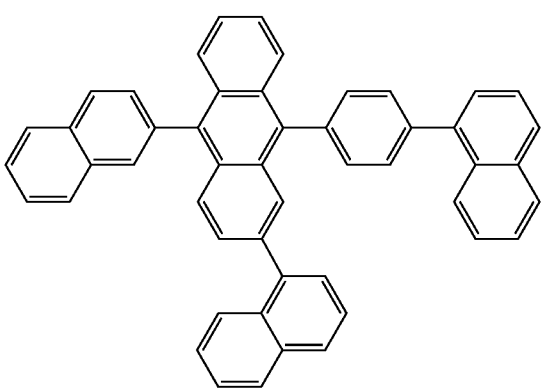

H22
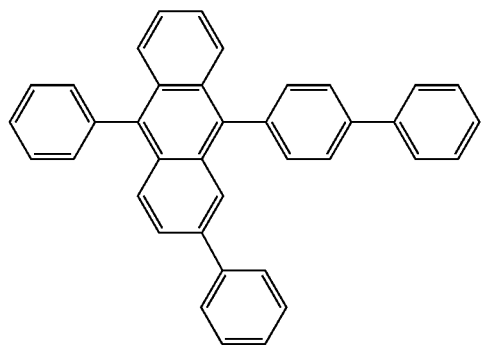
H23
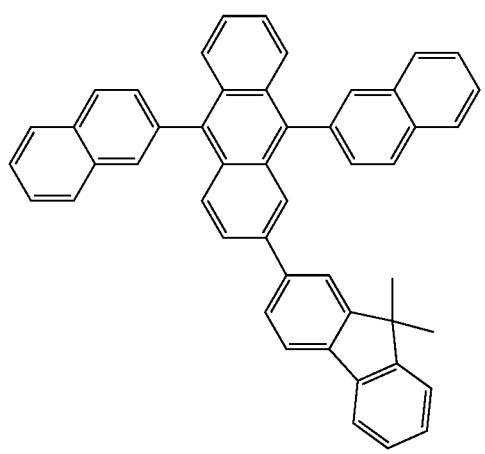
H24
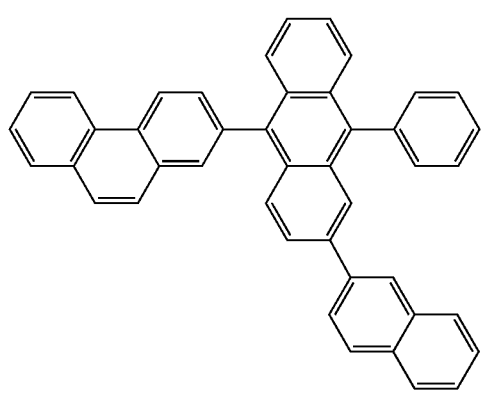
H25
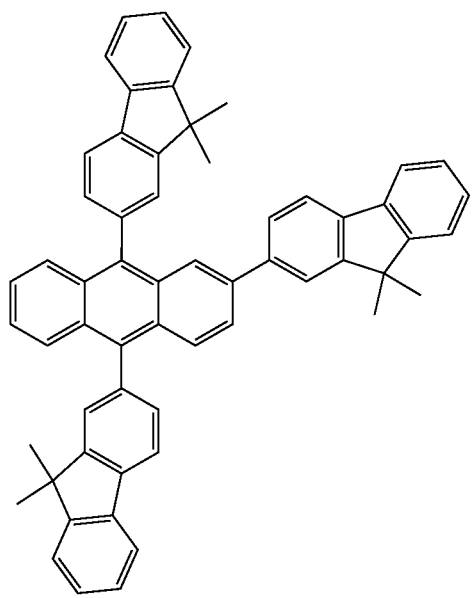
H26
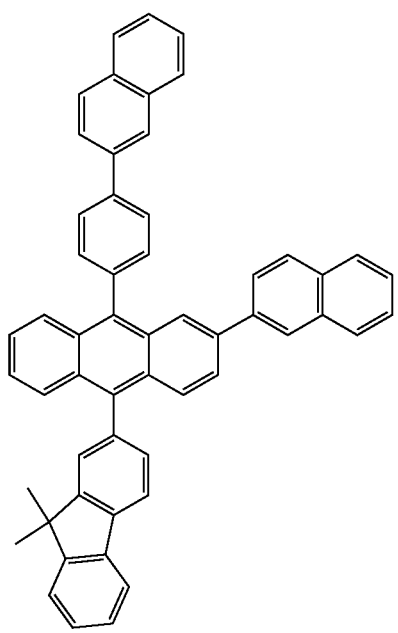

H27
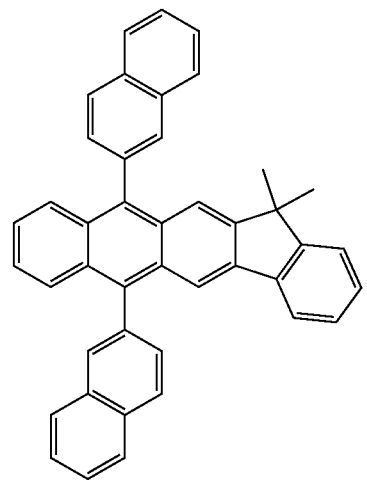
H28
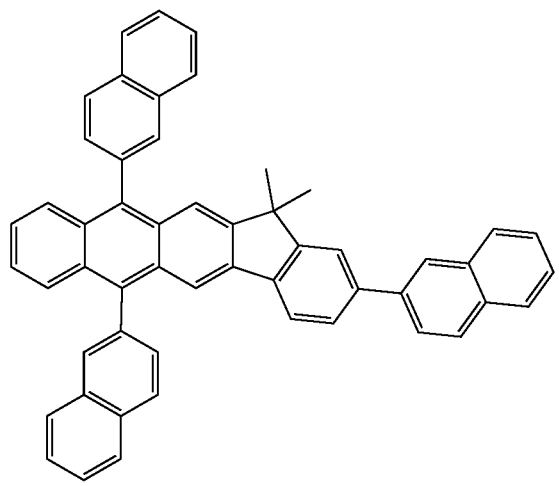
H29
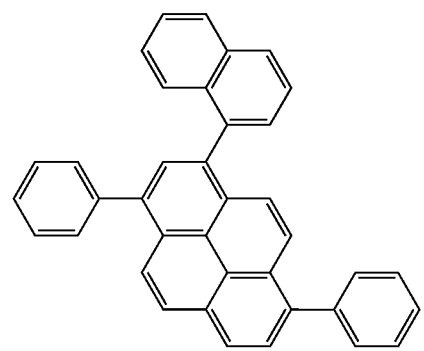
H30
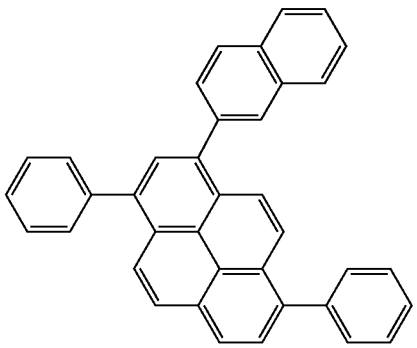
H31
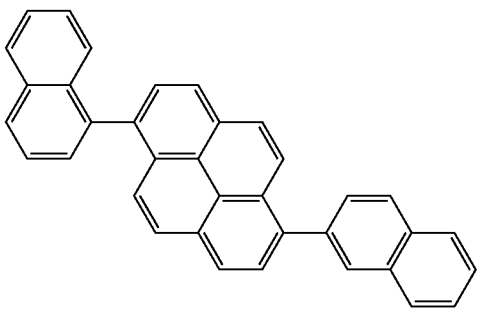
H32
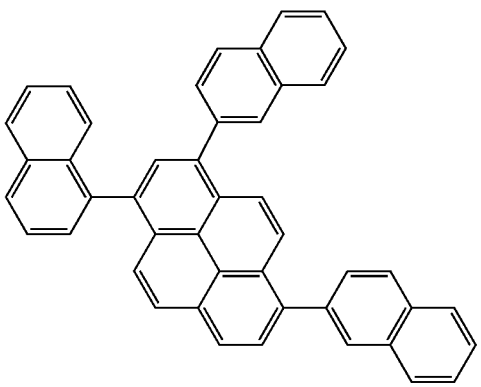
H33
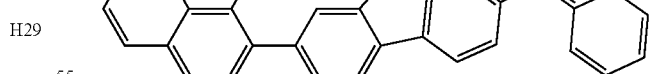
H34
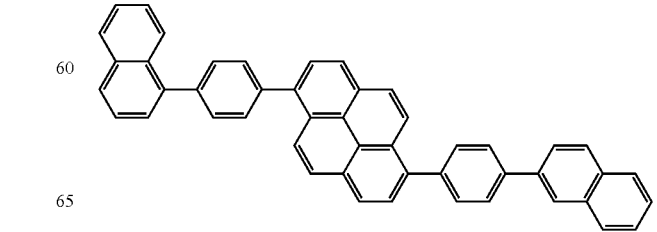

H35
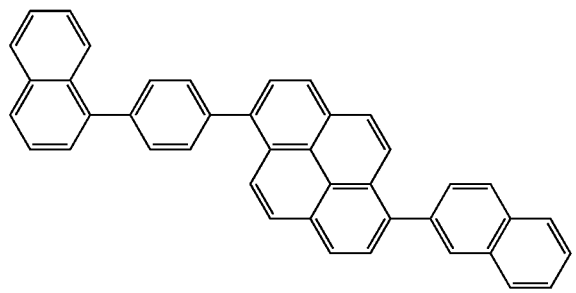
H36
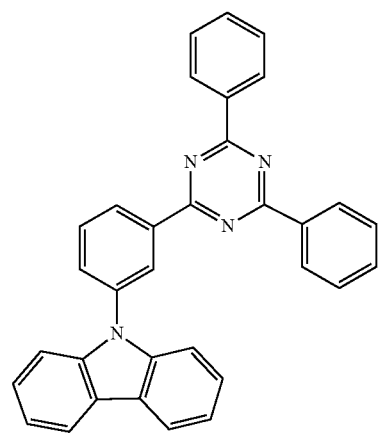
H37
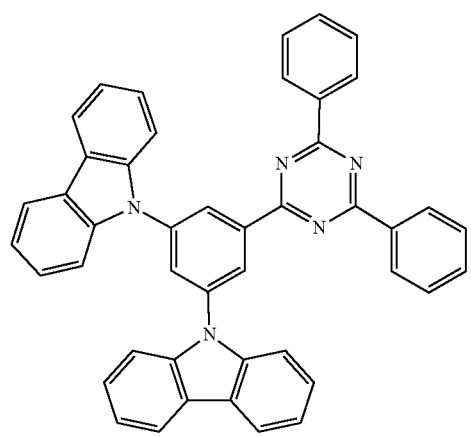
H38
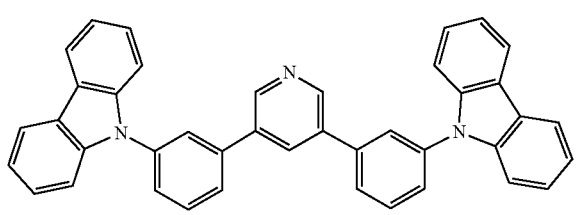
H39
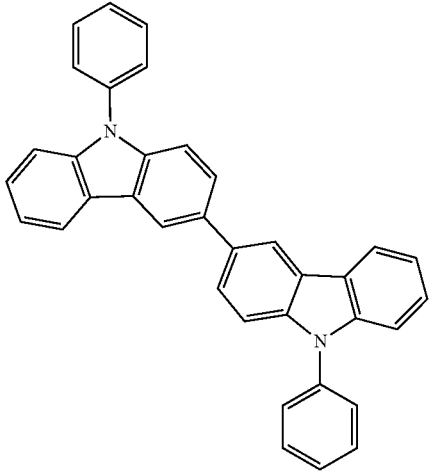
H40
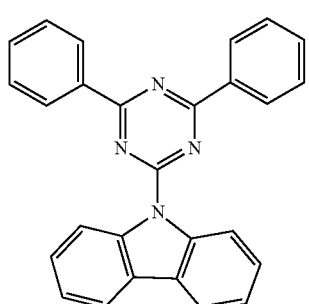
H41
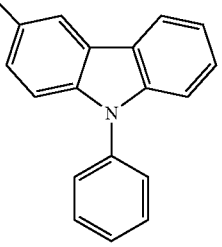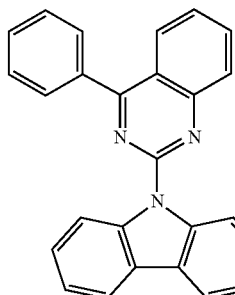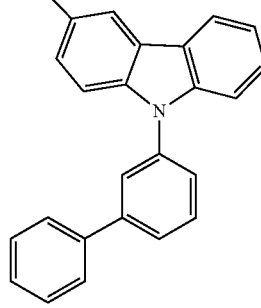

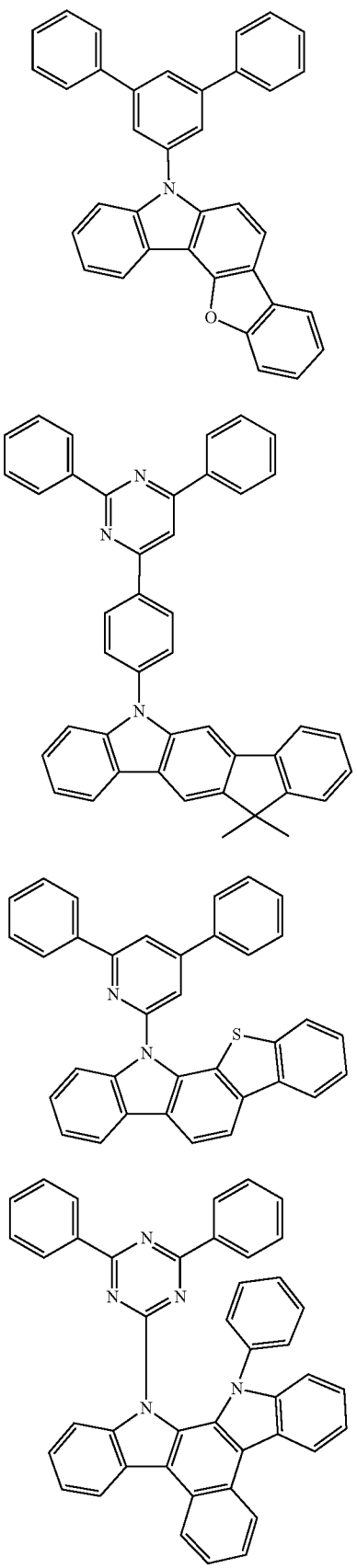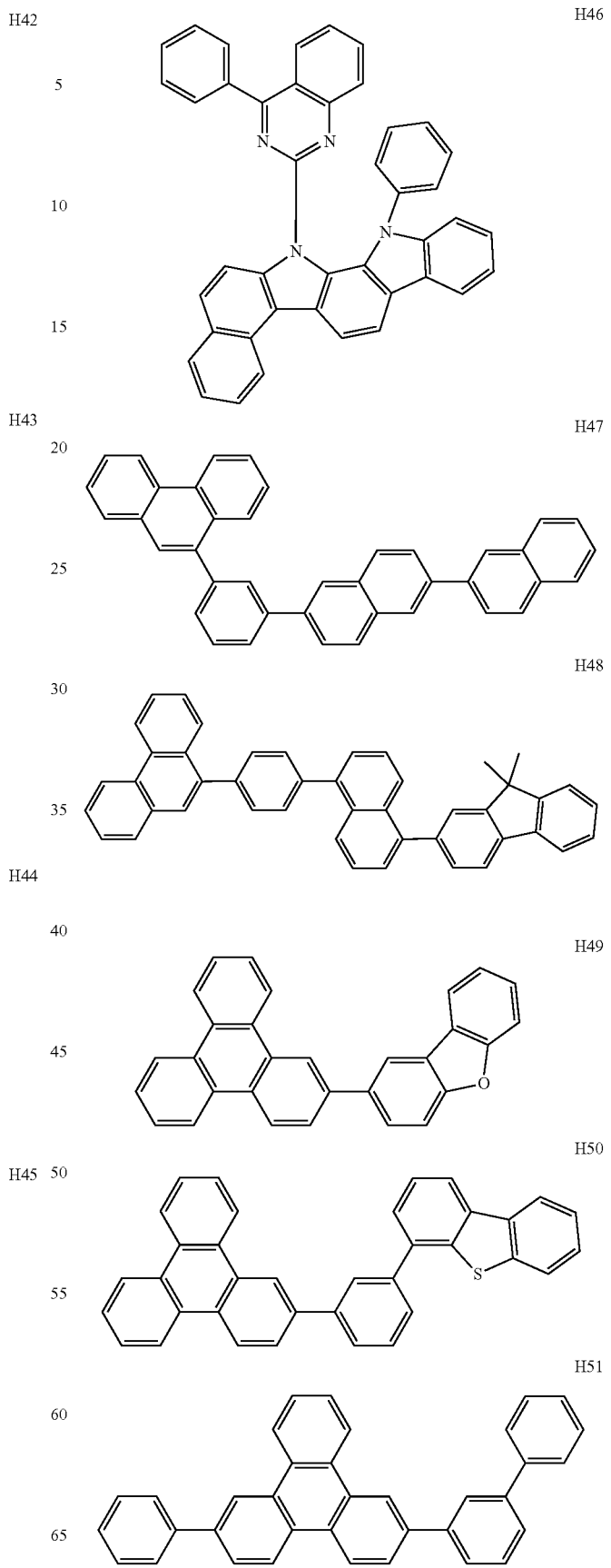

H52

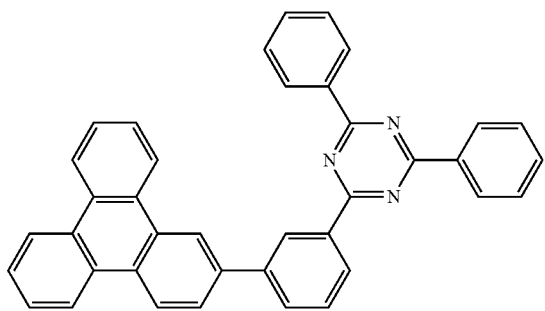

H53

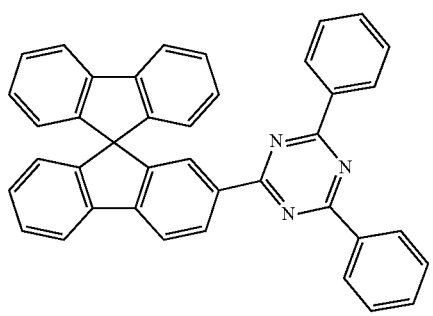

H54

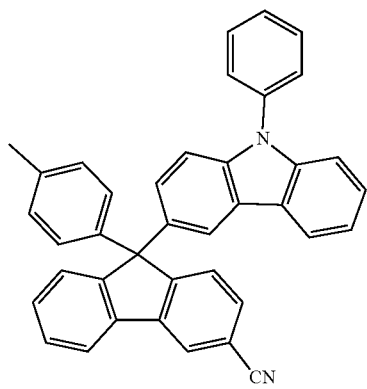

H55

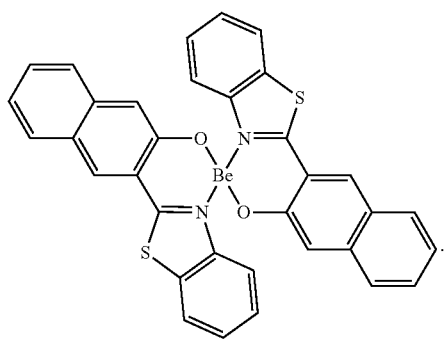

Phosphorescent Dopant Included in the Emission Layer 150

The phosphorescent dopant may include an organometallic complex represented by Formula 401 below:

$$M(L_{401})_{xc1}(L_{402})_{xc2} \quad \text{Formula 401}$$

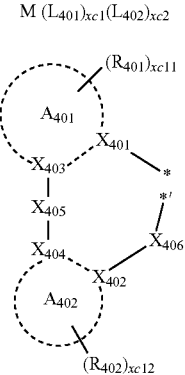

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be a ligand represented by Formula 402, and xc1 may be 1, 2, or 3, wherein when xc1 is two or more, two or more $L_{401}$(s) may be identical to or different from each other, $L_{402}$ may be an organic ligand, and xc2 may be an integer from 0 to 4, wherein when xc2 may be two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, A401 and A402 may each independently be a $C_5$-$C_{60}$ carbocyclic group or a $C_1$-$C_{60}$ heterocyclic group, $X_{405}$ may be a single bond, *—O—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*' or *=C=*', wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N(Q$_{401}$)(Q$_{402}$), —B(Q$_{401}$)(Q$_{402}$), —C(=O)(Q$_{401}$), —S(=O)$_2$(Q$_{401}$), and —P(=O)(Q$_{401}$)(Q$_{402}$), and Q$_{401}$ to Q$_{403}$ may each independently be selected from a C$_1$-C$_{10}$ alkyl group, a C$_1$-C$_{10}$ alkoxy group, a C$_6$-C$_{20}$ aryl group, and a C$_1$-C$_{20}$ heteroaryl group, xc11 and xc12 may each independently be an integer from 0 to 3, and

* and *' in Formula 402 each indicate a binding site to M in Formula 401.

In one embodiment, A401 and A402 in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) X$_{401}$ may be nitrogen and X$_{402}$ may be carbon, or ii) X$_{401}$ and X$_{402}$ may each be nitrogen at the same time.

In one or more embodiments, R$_{401}$ and R$_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantly group, a norbornanyl group, and a norbornenyl group;

a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantly group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si(Q$_{401}$)(Q$_{402}$)(Q$_{403}$), —N(Q$_{401}$)(Q$_{402}$), —B(Q$_{401}$)(Q$_{402}$), —C(=O)(Q$_{401}$), —S(=O)$_2$(Q$_{401}$), and —P(=O)(Q$_{401}$)(Q$_{402}$), wherein Q$_{401}$ to Q$_{403}$ may each independently be selected from a C$_1$-C$_{10}$ alkyl group, a C$_1$-C$_{10}$ alkoxy group, a phenyl group, a biphenyl group, and a naphthyl group, but embodiments of the present disclosure are not limited thereto.

In one or more embodiments, when xc1 in Formula 401 is two or more, two A401(s) in two or more L$_{401}$(s) may optionally be linked to each other via X$_{407}$, which is a linking group, and/or two A402(s) may optionally be linked to each other via X$_{408}$, which is a linking group (see e.g., Compounds PD1 to PD4 and PD7). X$_{407}$ and X$_{408}$ may each independently be a single bond, *—C(=O)—*', *—N(Q$_{413}$)-*', *—C(Q$_{413}$)(Q$_{414}$)-*' or *—C(Q$_{413}$)=C(Q$_{414}$)-*' (where Q$_{413}$ and Q$_{414}$ may each independently be hydrogen, deuterium, a C$_1$-C$_{20}$ alkyl group, a C$_1$-C$_{20}$ alkoxy group, a phenyl group, a biphenyl group, a terphenyl group, or a naphthyl group), but embodiments of the present disclosure are not limited thereto.

L$_{402}$ in Formula 401 may be a monovalent, divalent, or trivalent organic ligand. For example, L$_{402}$ may be selected from halogen, diketone (for example, acetylacetonate), carboxylic acid (for example, picolinate), —C(=O), isonitrile, —CN, and phosphorus (for example, phosphine, and/or phosphite), but embodiments of the present disclosure are not limited thereto.

In one or more embodiments, the phosphorescent dopant may be selected from, for example, Compounds PD1 to PD25, but embodiments of the present disclosure are not limited thereto:

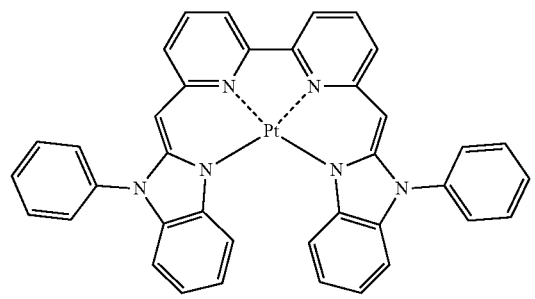

PD1

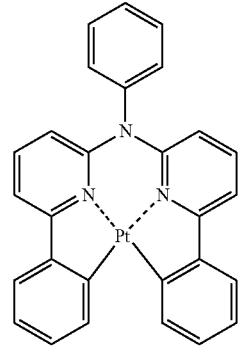

PD2

-continued
PD3
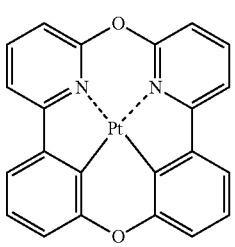
PD4
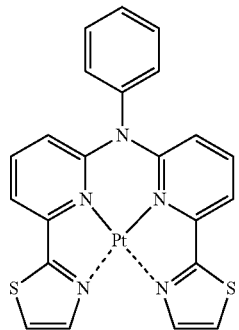
PD5
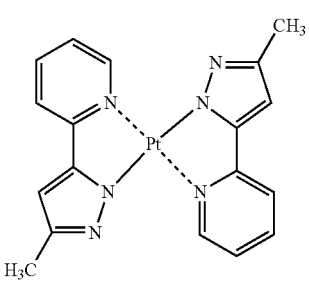
PD6
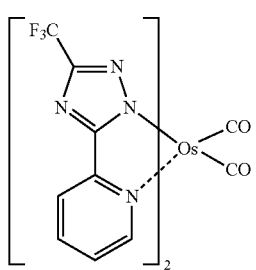
PD7
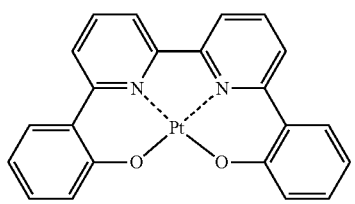
PD8
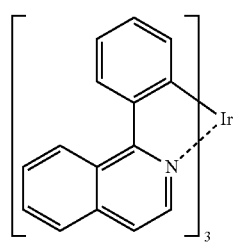
-continued
PD9
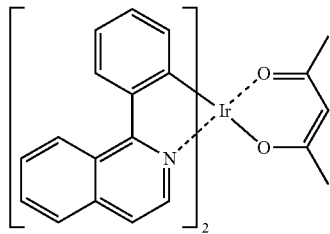
PD10
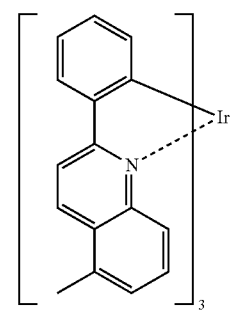
PD11
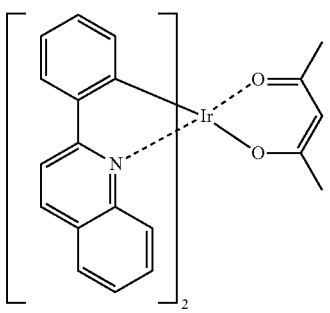
PD12
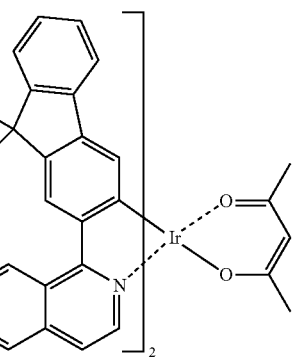
PD13
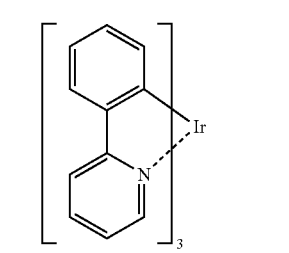

PD14 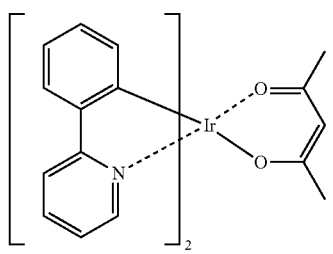
PD15 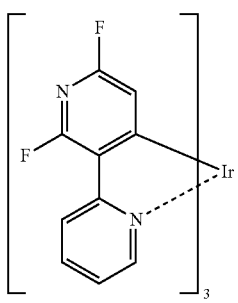
PD16 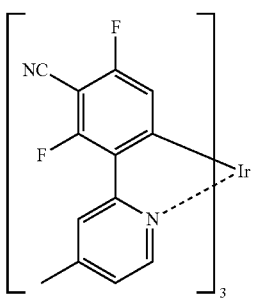
PD17 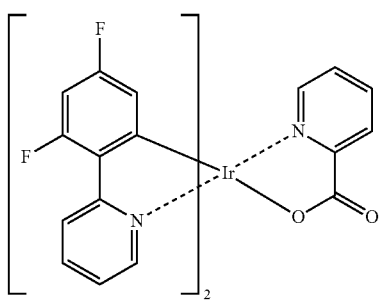
PD18 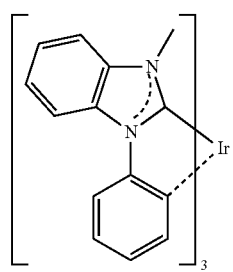
PD19 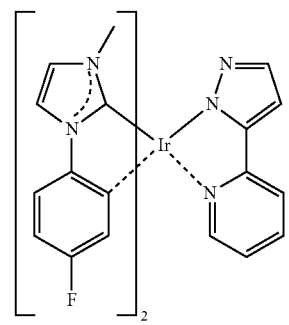
PD20 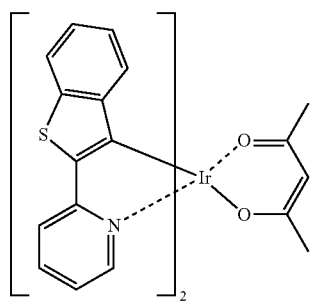
PD21 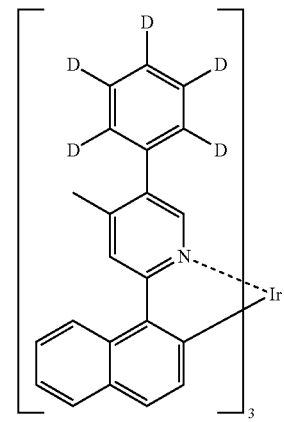
PD22 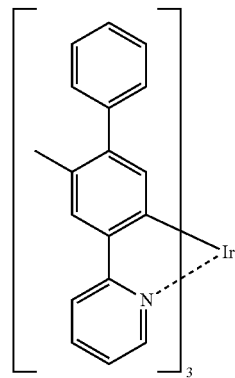

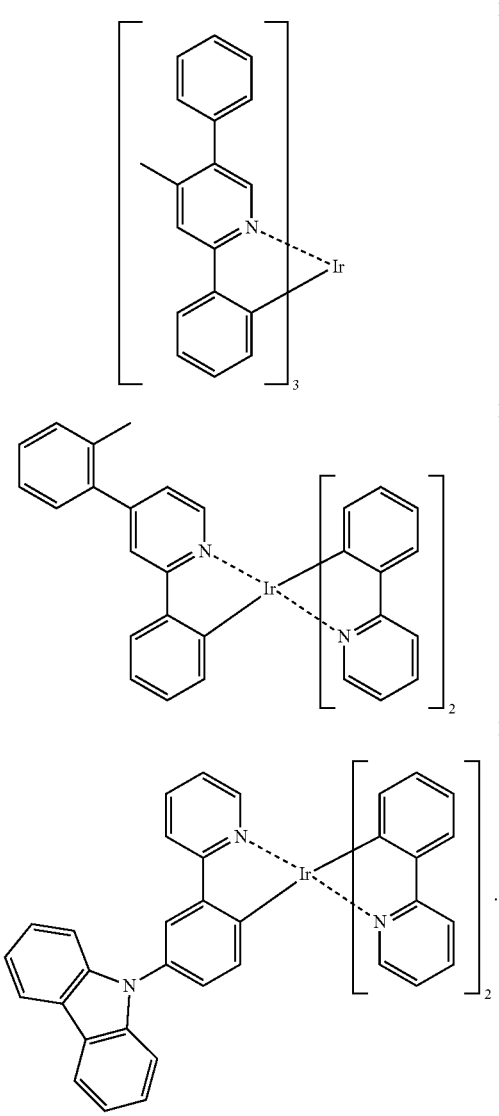

PD23

PD24

PD25

Fluorescent Dopant in Emission Layer 150

The fluorescent dopant may include an arylamine compound or a styrylamine compound.

The fluorescent dopant may include a compound represented by Formula 501 below.

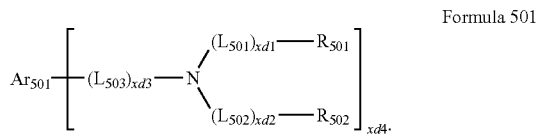

Formula 501

In Formula 501,

Ar$_{501}$ may be a substituted or unsubstituted $C_5$-$C_{60}$ carbocyclic group or a substituted or unsubstituted $C_1$-$C_{60}$ heterocyclic group, L$_{501}$ to L$_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, R$_{501}$ and R$_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In one embodiment, Ar$_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, L$_{501}$ to L$_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

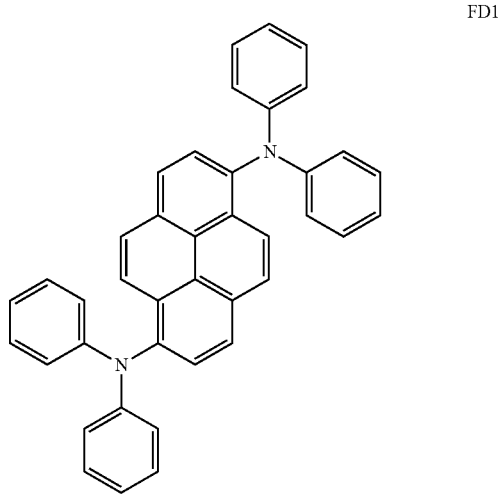

FD1

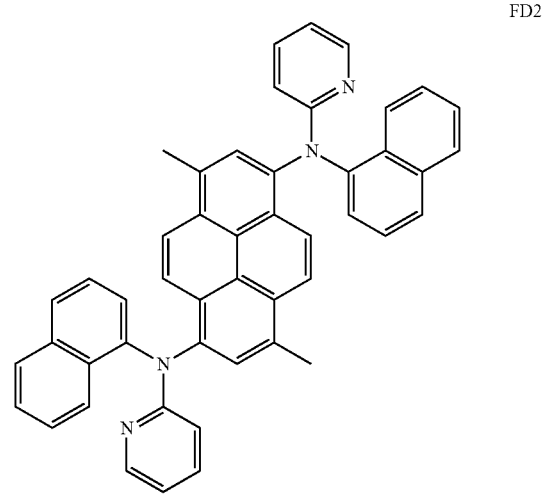

FD2

-continued
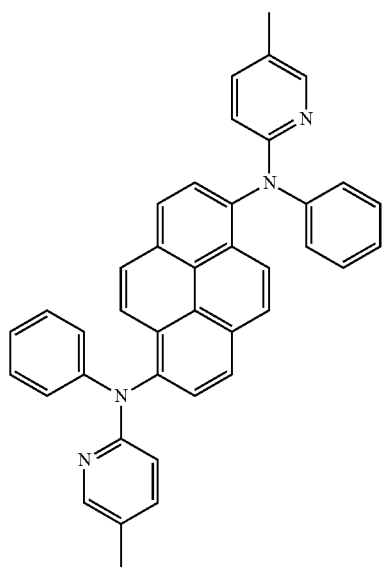
FD3
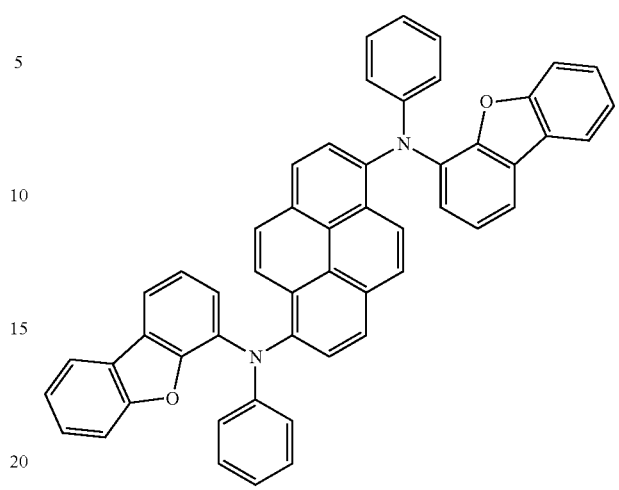
FD5
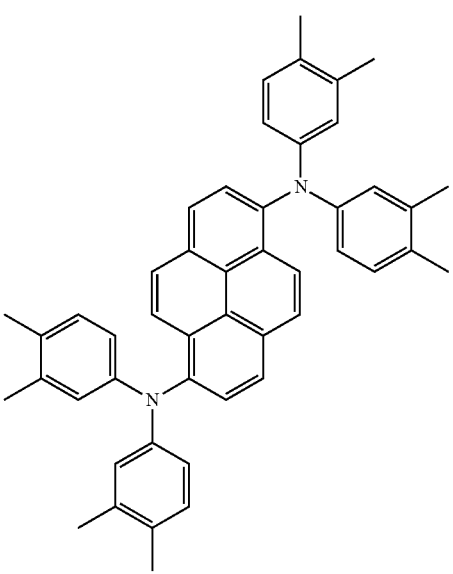
FD6
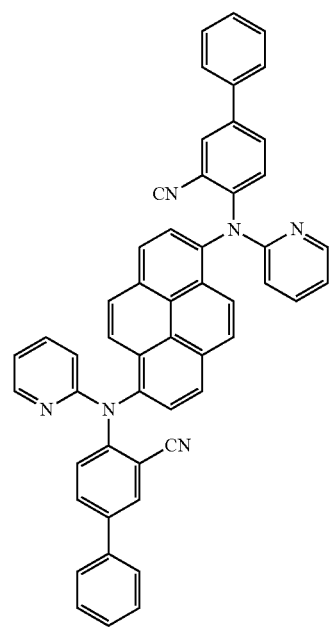
FD4
FD7

FD8
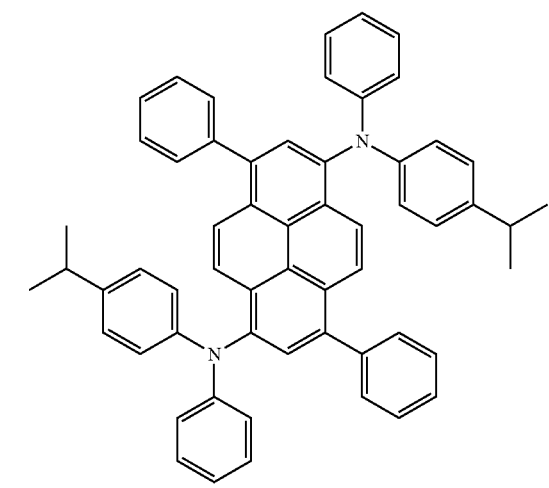
FD9
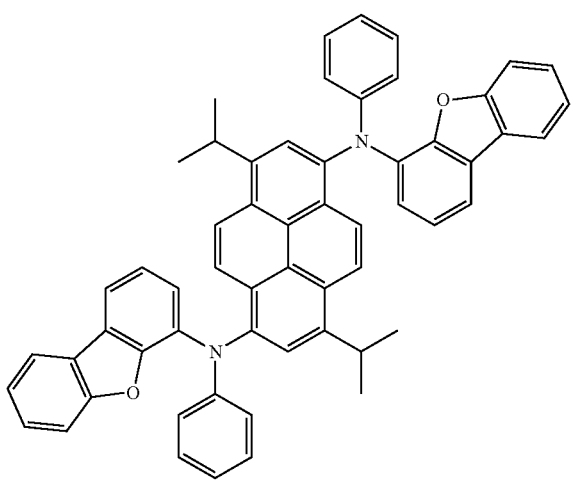
FD10
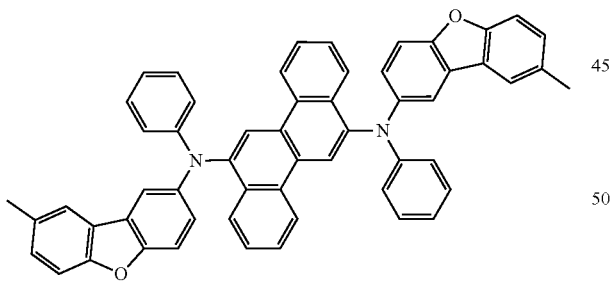
FD11
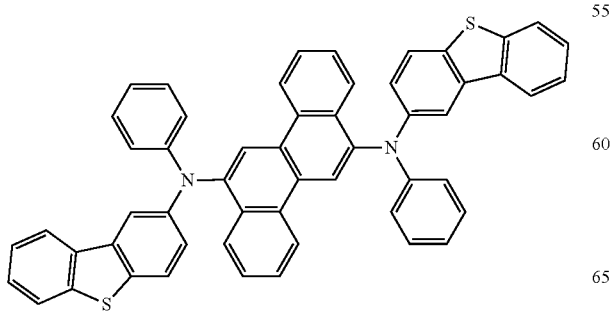
FD12
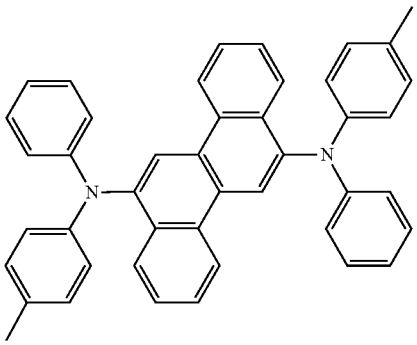
FD13
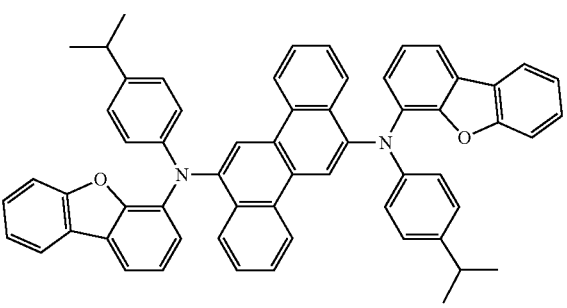
FD14
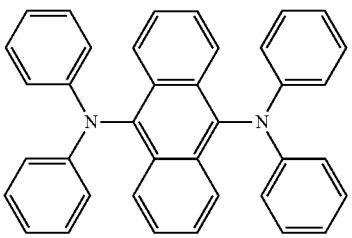
FD15
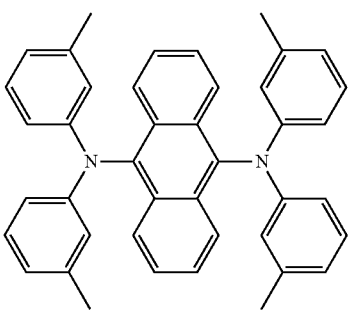
FD16
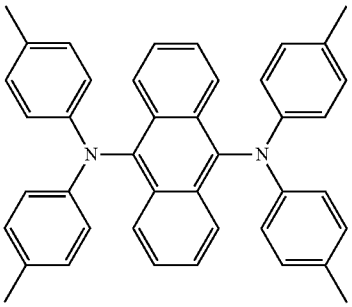

-continued
FD17
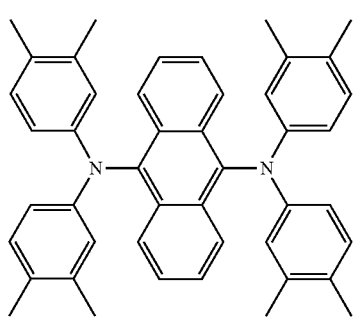
FD18
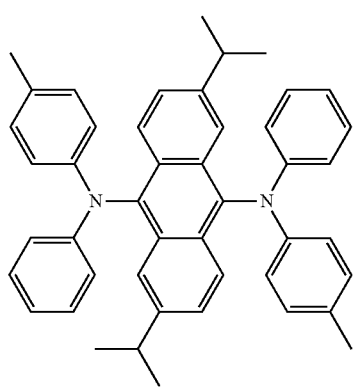
FD19
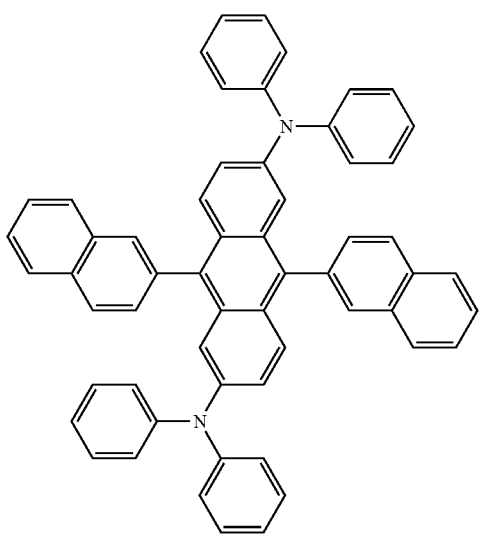
-continued
FD20
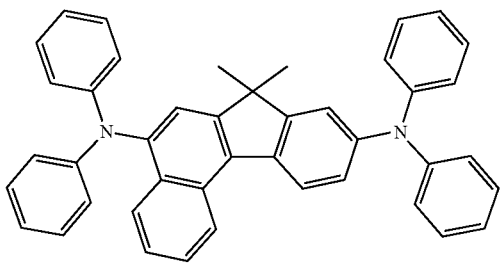
FD21
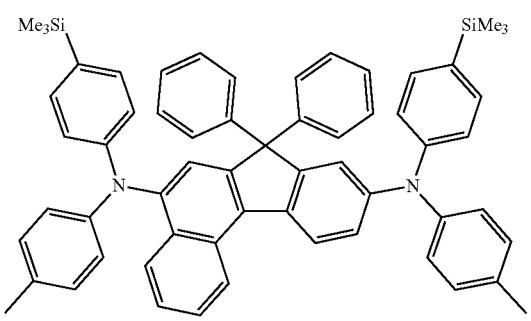
FD22
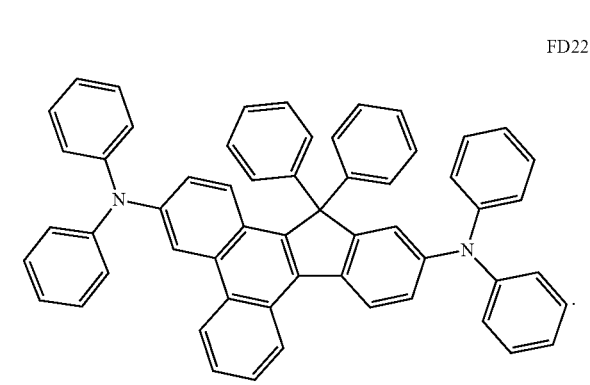
In one or more embodiments, the fluorescent dopant may be selected from the following compounds, but embodiments of the present disclosure are not limited thereto.
DPVBi
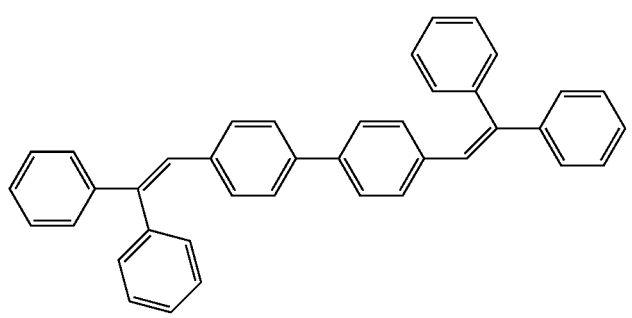

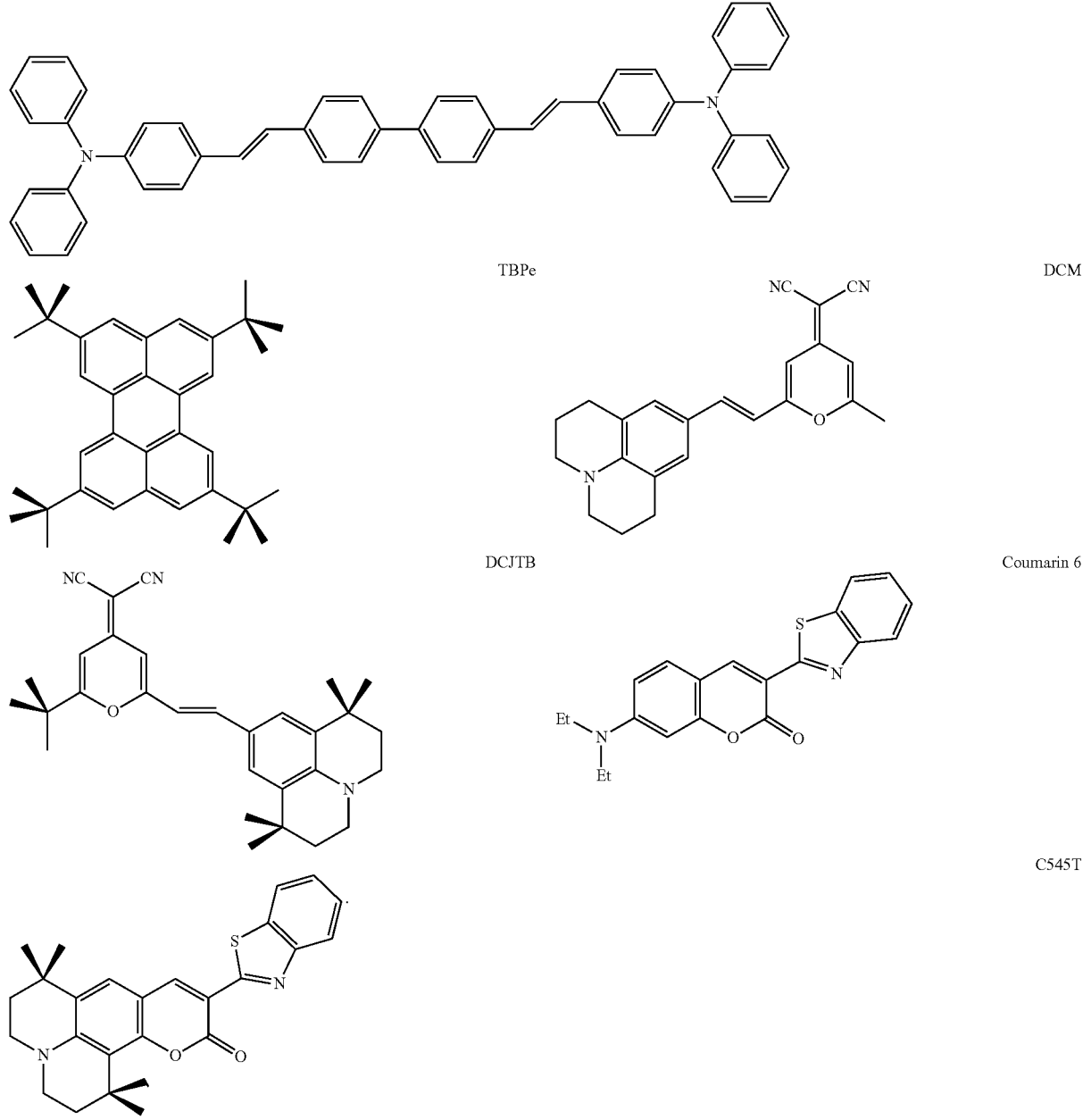

In one or more embodiments, the fluorescent dopant may be a TADF emitter that can emit thermally activated delayed fluorescence light.

For example, the fluorescent dopant may satisfy Equation 5.

$$\Delta E_{st} = S1 - T1 \leq 0.5 \text{ eV,} \quad \text{Equation 5}$$

wherein, in the Equation above,

S1 is the lowest excitation singlet energy level of the fluorescent dopant, and

T1 is the lowest excitation triplet energy level of the fluorescent dopant.

When Equation 5 is satisfied, thermally activated delayed fluorescence may be suitably emitted even at room temperature.

For example, the condition of $\Delta E_{st} \leq 0.3$ eV may be satisfied, but embodiments of the present disclosure are not limited thereto.

Quantum Dot

The emission layer 150 included in the organic light-emitting device of present disclosure may include a quantum dot.

The quantum dot is a particle having a crystal structure of several to several tens of nanometers, and includes hundreds to thousands of atoms.

Because the quantum dot is very small in size, a quantum confinement effect may occur. The quantum confinement effect refers to a phenomenon in which a band gap of an object becomes large when the object becomes smaller than a nanometer size. Accordingly, when light having a wavelength having an energy intensity that is greater than the band gap of the quantum dot is irradiated to the quantum dot, the quantum dot is excited by absorbing the light, and emits light having a set or specific wavelength as it transitions to the ground state. In this case, the wavelength of the emitted light has a value corresponding to the band gap.

The core of the quantum dot may include a Group II-VI compound, a Group III-VI compound, a Group III-V compound, a Group IV-VI compound, a Group IV element, a Group IV compound, a Group I-III-VI compound, or a combination thereof.

The Group II-VI compound may be selected from a binary compound selected from CdS, CdSe, CdTe, ZnS, ZnSe, ZnTe, ZnO, HgS, HgSe, HgTe, MgSe, MgS, and any mixture thereof; a ternary compound selected from CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, any mixture thereof; and a quaternary compound selected from CdZnSeS, CdZnSeTe, CdZnSTe, CdHgSeS, CdHgSeTe, CdHgSTe, HgZnSeS, HgZnSeTe, HgZnSTe, and any mixture thereof.

The Group III-VI compound may include: a binary compound, such as $In_2S_3$ and/or $In_2Se$; a ternary compound, such as $InGaS_3$ and/or $InGaSe_3$; or any combination thereof.

For example, the Group III-V compound may be selected from: a binary compound selected from GaN, GaP, GaAs, GaSb, AlN, AlP, AlAs, AlSb, InN, InP, InAs, InSb, and any mixture thereof; a ternary compound selected from GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, GaAlNP, and any mixture thereof; and a quaternary compound selected from GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and any mixture thereof, but embodiments of the present disclosure are not limited thereto. The Group III-V semiconductor compound may further include Group II metal (for example, the compound may be InZnP, etc.).

The Group IV-VI compound may be selected from: a binary compound selected from SnS, SnSe, SnTe, PbS, PbSe, PbTe, and any mixture thereof; a ternary compound selected from SnSeS, SnSeTe, SnSTe, PbSeS, PbSeTe, PbSTe, SnPbS, SnPbSe, SnPbTe, and any mixture thereof; and a quaternary compound selected from SnPbSSe, SnPbSeTe, SnPbSTe, and any mixture thereof. The IV group element may be selected from Si, Ge, and any mixture thereof. The Group IV compound may be a binary compound selected from SiC, SiGe, and any mixture thereof.

The binary compound, the ternary compound, or the quaternary compound may each independently exist in particles at uniform concentration, or may exist in the same particle in a state in which a concentration distribution is partially different. In addition, the binary compound, the ternary compound, or the quaternary compound may each independently have a core-shell structure in which one quantum dot surrounds another quantum dot. An interface between the core and the shell may have a concentration gradient in which the concentration of atoms existing in the shell decreases toward the center.

In one or more embodiments, the quantum dot may have a core-shell structure including a core with the above-described nanoparticles and a shell surrounding the core. The shell of the quantum dot may serve as a protective layer for maintaining semiconductor characteristics by preventing or reducing chemical degeneration of the core, and/or may serve as a charging layer for imparting electrophoretic characteristics to the quantum dot. The shell may be a single layer or a multilayer. An interface between the core and the shell may have a concentration gradient in which the concentration of atoms existing in the shell decreases toward the center. Examples of the shell of the quantum dot may include a metal oxide, a non-metal oxide, a semiconductor compound, or any combination thereof.

Examples of the metal oxide and non-metal oxide include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO, and a ternary compound such as $MgAl_2O_4$, $CoFe_2O_4$, $NiFe_2O_4$, and/or $CoMn_2O_4$, but embodiments of the present disclosure are not limited thereto.

In addition, examples of the semiconductor compound include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, and the like, but embodiments of the present disclosure are not limited thereto.

A full width of half maximum (FWHM) of an emission wavelength spectrum of the quantum dot may be about 45 nm or less, for example, about 40 nm or less, for example, about 30 nm or less. In addition, light emitted through such quantum dot is irradiated in omnidirection, thereby improving a wide viewing angle.

The quantum dot may any suitable quantum dot in the art, and is not particularly limited. For example, a spherical, pyramidal, multi-arm, and/or cubic nanoparticle, nanotube, nanowire, nanofiber, and/or nanoplate particle may be used as the quatum dot.

The quantum dot may adjust the color of emitted light according to the particle size. Therefore, the quantum dot may various emission colors such as blue, red, or green.

Electron Transport Region in Organic Layer

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one π electron-depleted nitrogen-containing ring.

The "π electron-depleted nitrogen-containing ring" may refer to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups, each having at least one *—N=*' moiety, are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-deficient nitrogen-containing ring include an imidazole ring, a pyrazole ring, a thiazole ring, an isothiazole ring, an oxazole ring, an isoxazole ring, a pyridine ring, a pyrazine ring, a pyrimidine ring, a pyridazine ring, an indazole ring, a purine ring, a quinoline ring, an isoquinoline ring, a benzoquinoline ring, a phthalazine ring, a naphthyridine ring, a quinoxaline ring, a quinazoline ring, a cinnoline ring, a phenanthridine ring, an acridine ring, a phenanthroline ring, a phenazine ring, a benzimidazole ring, an isobenzothiazole ring, a benzoxazole ring, an isobenzoxazole ring, a triazole ring, a tetrazole ring, an oxadiazole ring, a triazine ring, a thiadiazole ring, an imidazopyridine ring, an imidazopyrimidine ring, and an azacarbazole ring, but are not limited thereto.

For example, the electron transport region may include a compound represented by Formula 601 below:

Formula 601

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$(s) in the number of xe11 and $R_{601}$(s) in the number of xe21 may include the π electron-deficient nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or more, two or more $Ar_{601}$(s) may be linked to each other via a single bond.

In one or more embodiments, $Ar_{601}$ in Formula 601 may be an anthracene group.

In one or more embodiments, the compound represented by Formula 601 may be represented by Formula 601-1 below:

Formula 601-1

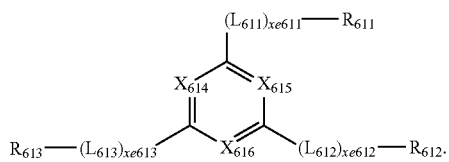

In Formula 601-1,
$X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N,
$L_{611}$ to $L_{613}$ may each independently be the same as described in connection with $L_{601}$,
xe611 to xe613 may each independently be the same as described in connection with xe1,
$R_{611}$ to $R_{613}$ may each independently be the same as described in connection with $R_{601}$, and
$R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:
a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and
a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group,
but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be selected from:
a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S($=$O)$_2$(Q$_{601}$) and —P($=$O)(Q$_{601}$)(Q$_{602}$), wherein Q$_{601}$ and Q$_{602}$ are the same as described above.

The electron transport region may include at least one compound selected from Compounds ET1 to ET36, but embodiments of the present disclosure are not limited thereto:

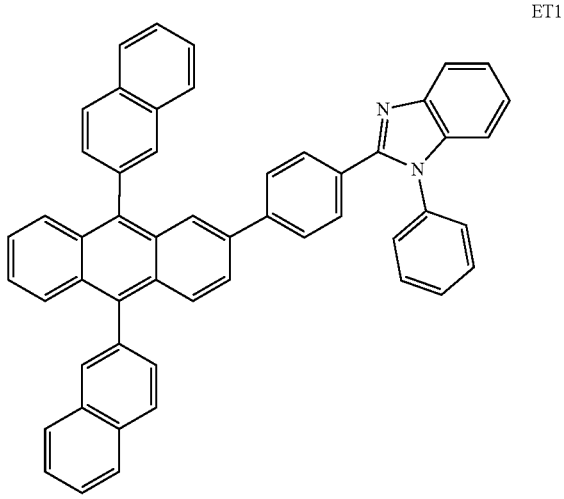

ET1

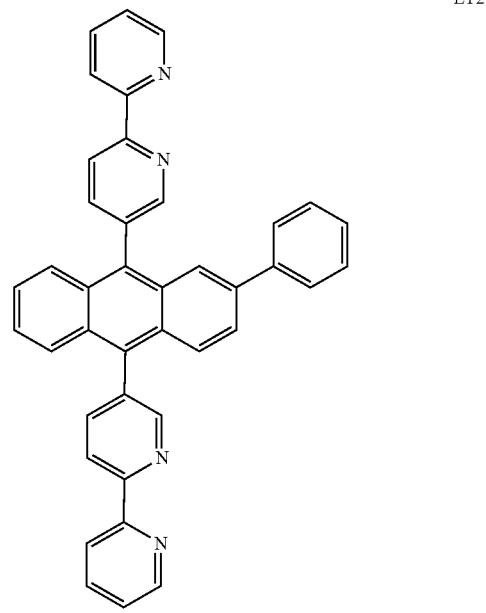

ET2

-continued
ET3
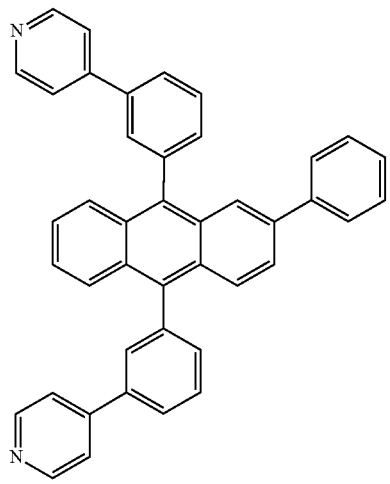
ET4
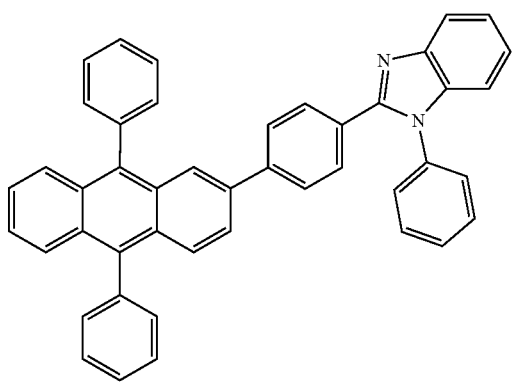
ET5
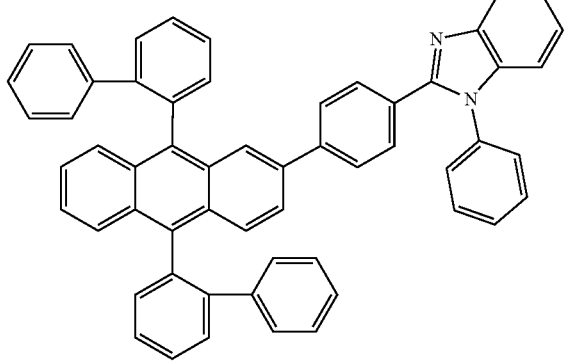
-continued
ET6
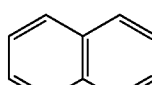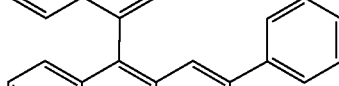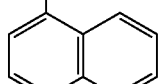
ET7
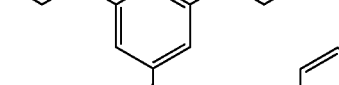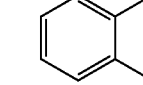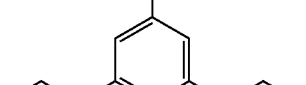
ET8
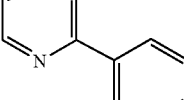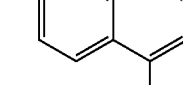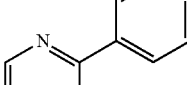

-continued
ET9
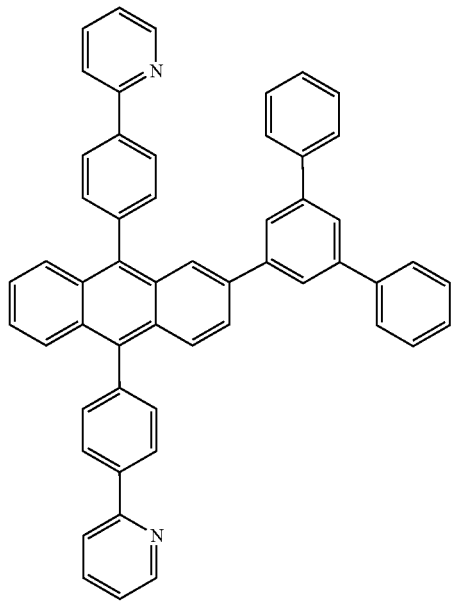
ET10
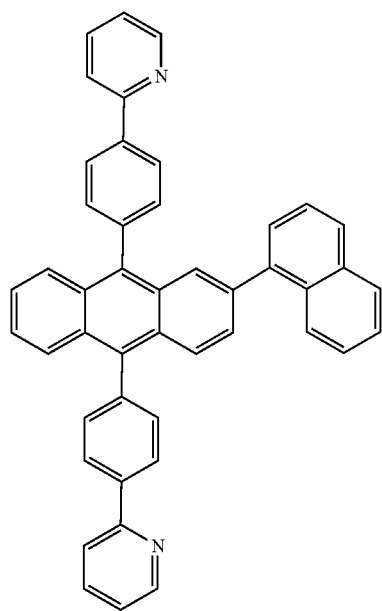
ET11
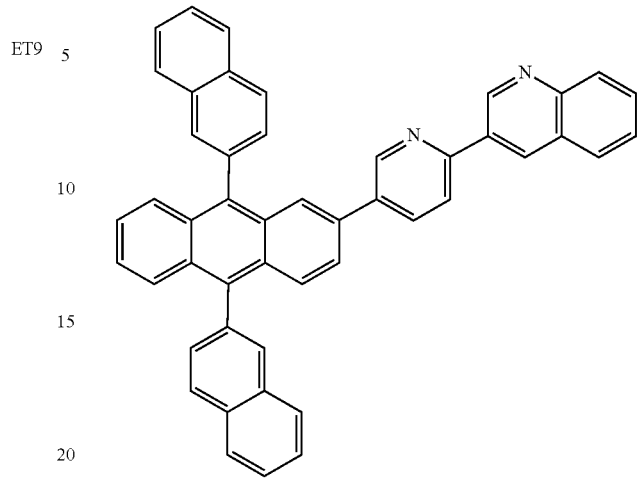
ET12
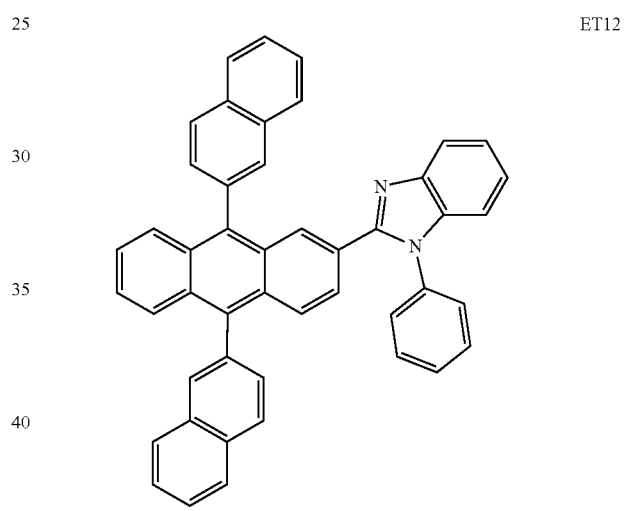
ET13
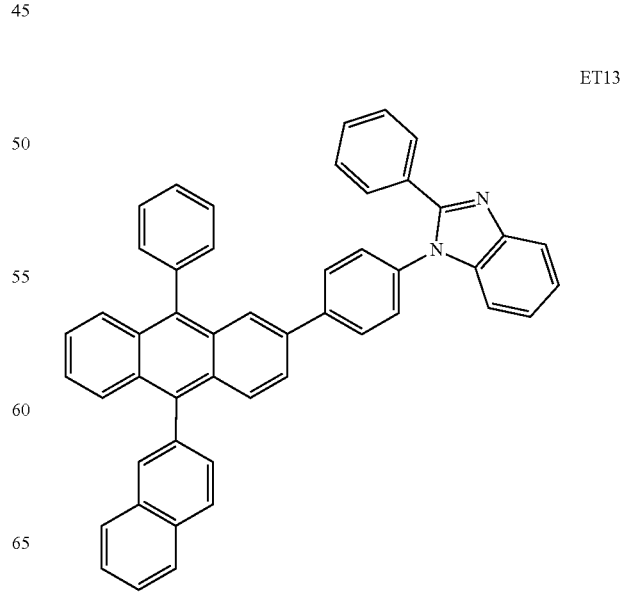

ET14
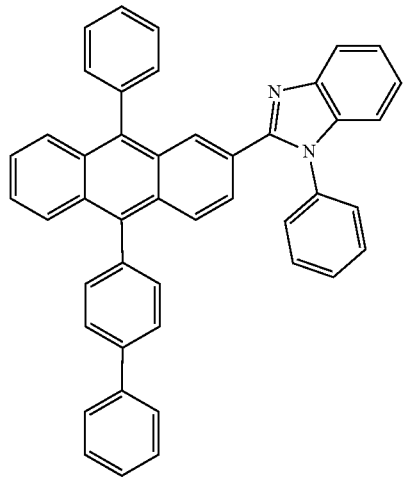
ET15
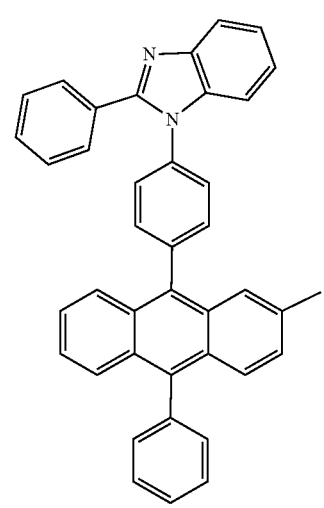
ET16
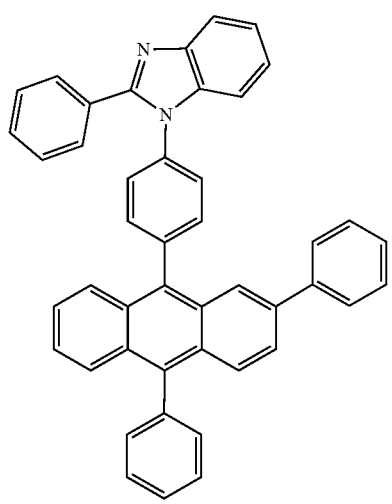
ET17
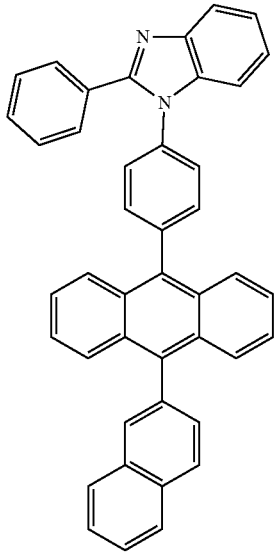
ET18
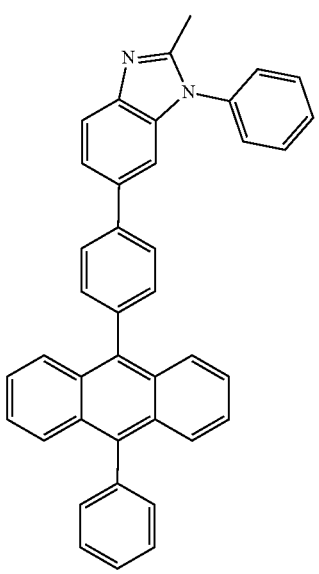
ET19
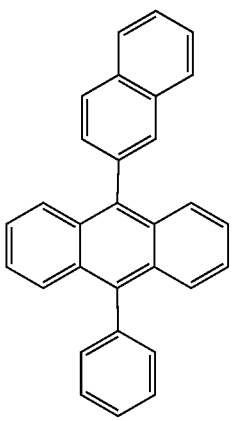

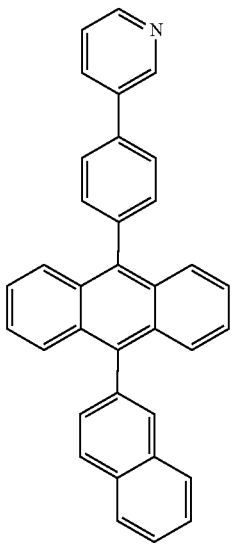
ET20
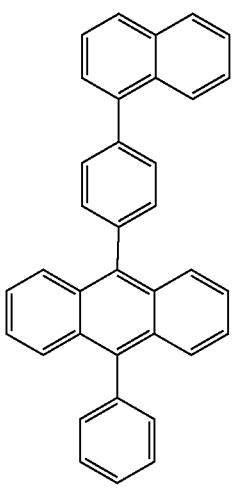
ET21
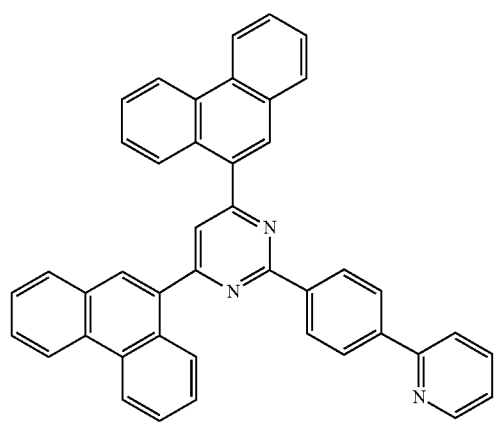
ET22
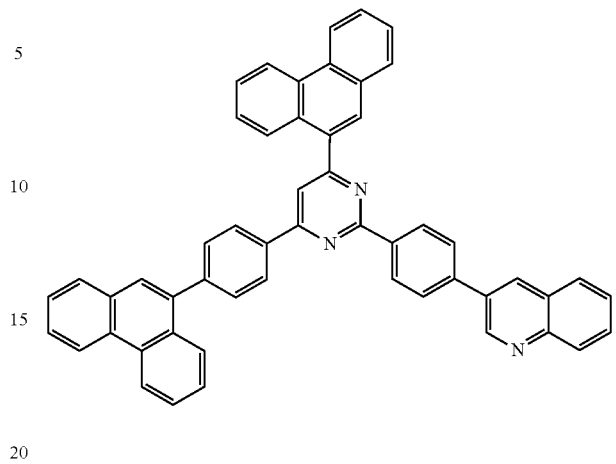
ET23
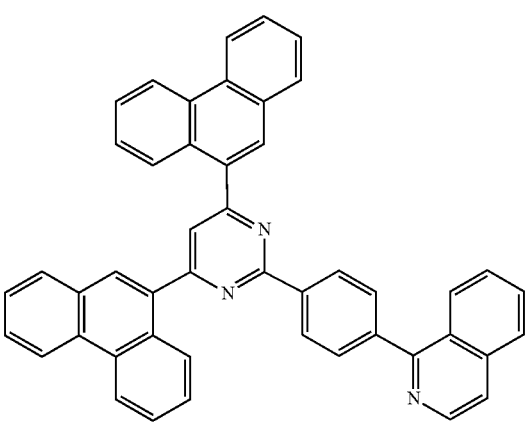
ET24
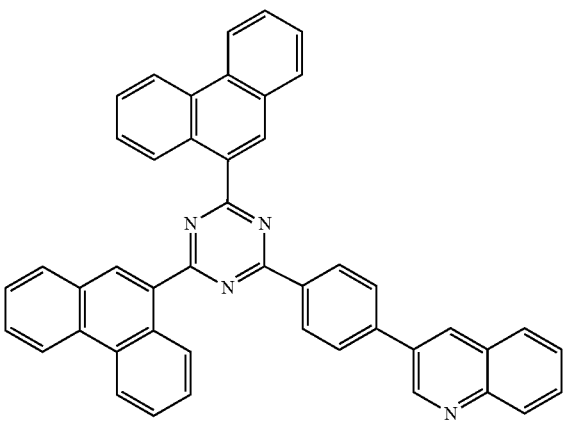
ET25

ET26
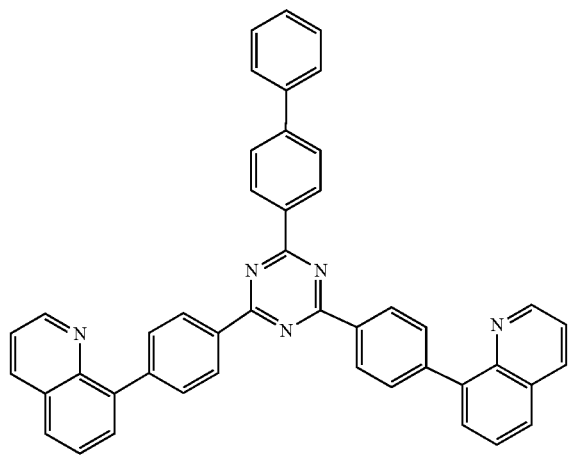
ET27
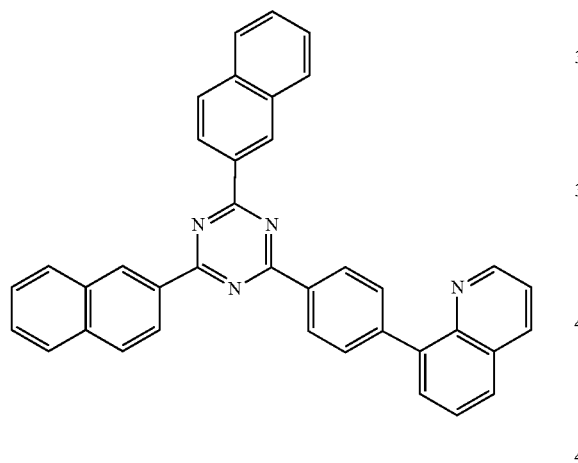
ET28
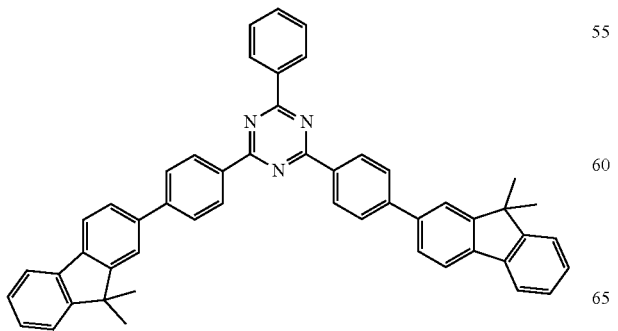
ET29
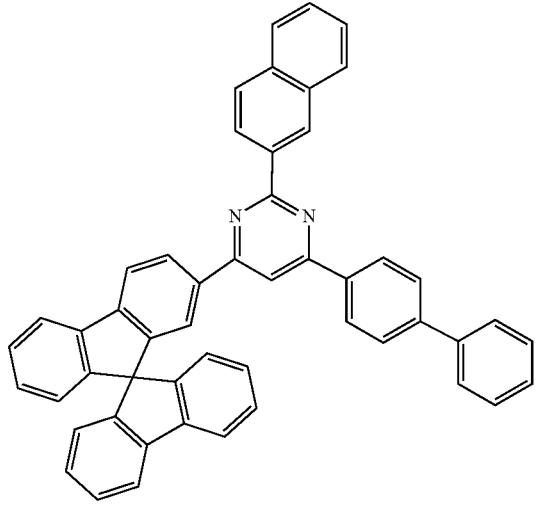
ET30
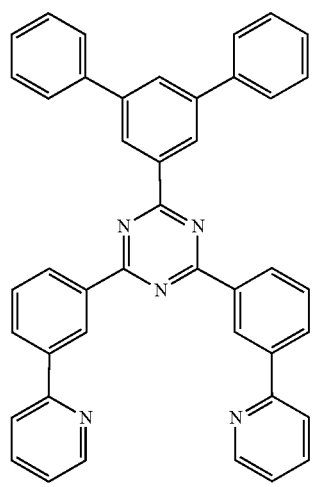
ET31
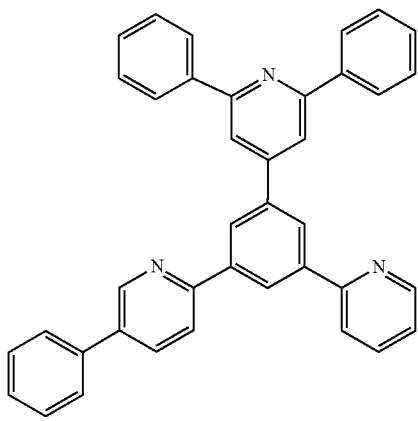

ET32
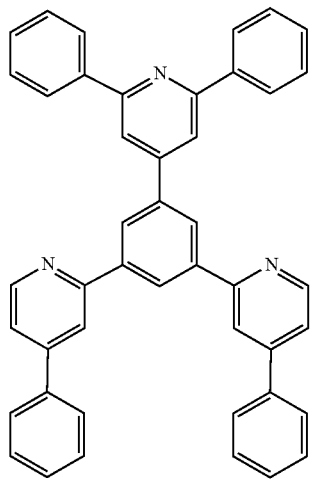
ET35
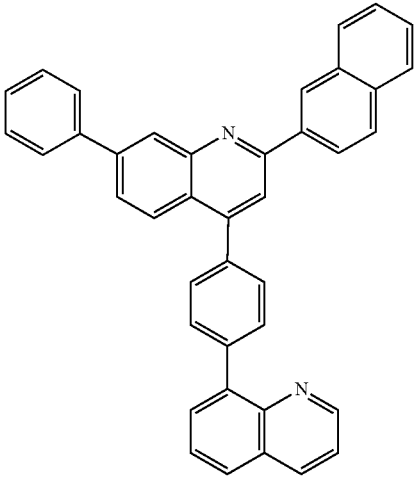
ET33
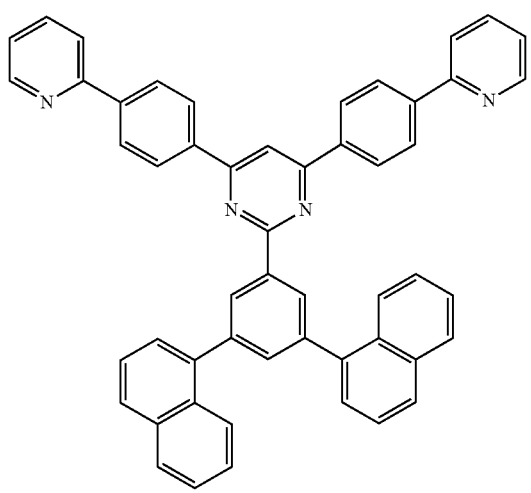
ET36
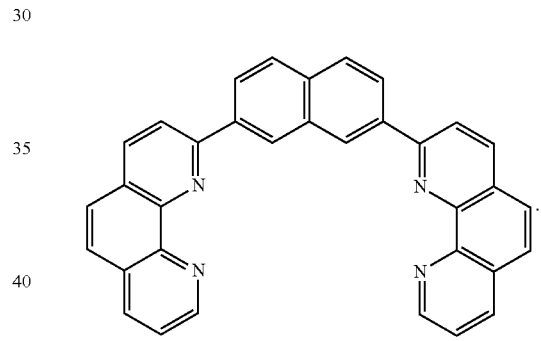
In one or more embodiments, the electron transport region may include at least one compound selected from 2,9-dimethyl-4,7-diphenyl-1,10-phenanthroline (BCP), 4,7-diphenyl-1,10-phenanthroline (Bphen), Alq3, BAlq, 3-(biphenyl-4-yl)-5-(4-tert-butylphenyl)-4-phenyl-4H-1,2,4-triazole (TAZ), and NTAZ.
ET34
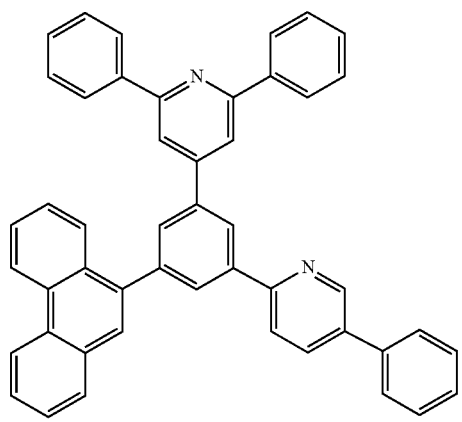
Alq3
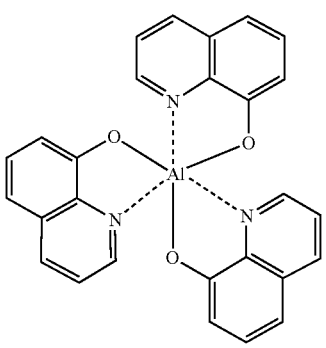

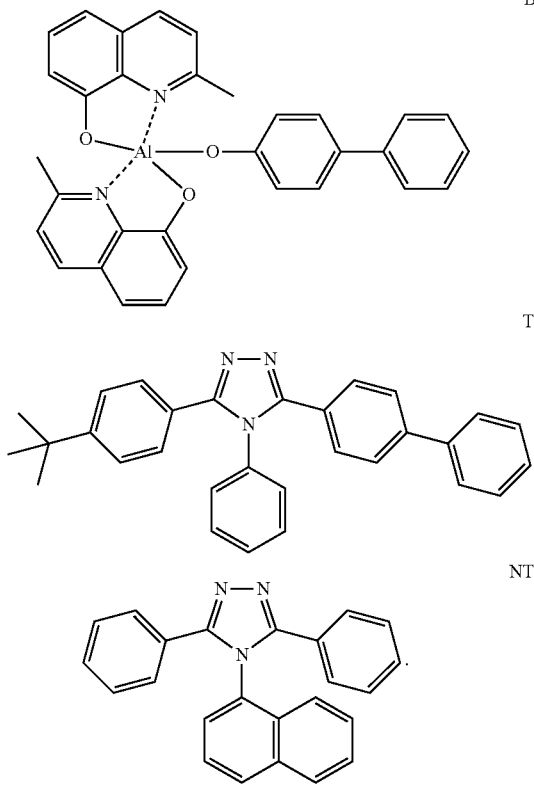

Balq

TAZ

NTAZ

Thicknesses of the buffer layer, the hole blocking layer, and the electron control layer may each independently be in a range of about 20 Å to about 1,000 Å, for example, about 30 Å to about 300 Å. When the thicknesses of the buffer layer, the hole blocking layer, and the electron control layer are each independently within any of these ranges, excellent (or improved) hole blocking characteristics and/or excellent (or improved) electron control characteristics may be obtained without a substantial increase in driving voltage.

A thickness of the electron transport layer may be in a range of about 100 Å to about 1,000 Å, for example, about 150 Å to about 500 Å. When the thickness of the electron transport layer is within any of the ranges described above, the electron transport layer may have satisfactory (or suitable) electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) and/or Compound ET-D2:

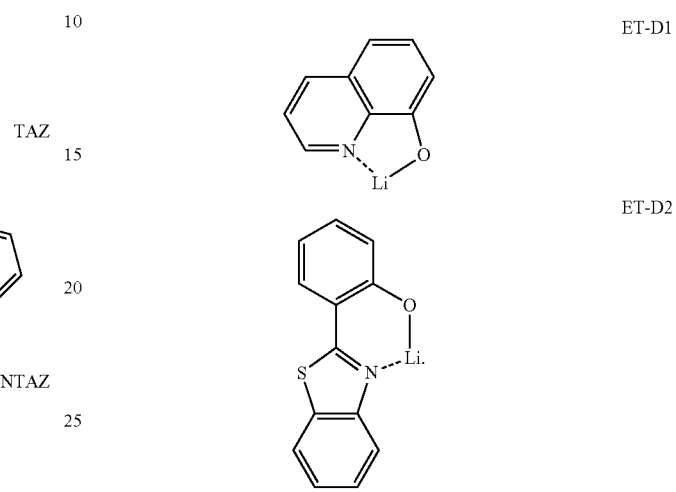

The electron transport region may include an electron injection layer that facilitates electron injection from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, and/or iodides) of the alkali metal, the alkaline earth-metal, and the rare earth metal, respectively.

The alkali metal compound may be selected from alkali metal oxides, such as $Li_2O$, $Cs_2O$, and/or $K_2O$, and alkali metal halides, such as LiF, NaF, CsF, KF, LiI, NaI, CsI, and/or KI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), and/or $Ba_xCa_{1-x}O$ (0<x<1).

In one embodiment, the alkaline earth-metal compound may be selected from BaO, SrO, and CaO, but embodiments of the present disclosure are not limited thereto.

The rare earth metal compound may be selected from $YbF_3$, $ScF_3$, $Sc_2O_3$, $Y_2O_3$, $Ce_2O_3$, $GdF_3$ and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may respectively include an ion of alkali metal, alkaline earth-metal, and rare earth metal as described above, and a ligand coordinated with a metal ion of the alkali metal complex, the alkaline earth-metal complex, or the rare earth metal complex may each independently be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may include (e.g., may consist of) an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within any of the ranges described above, the electron injection layer may have satisfactory (or suitable) electron injection characteristics without a substantial increase in driving voltage.

Second Electrode 190

The second electrode 190 is located on an organic layer having such a structure. The second electrode 190 may be a cathode, which is an electron injection electrode, and in this regard, a material for forming the second electrode 190 may be selected from a metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure or a multi-layered structure including two or more layers.

The organic light-emitting device 10 may further include a capping layer positioned in a direction in which light is emitted.

The capping layer may increase external luminescence efficiency according to the principle of constructive interference.

The capping layer may be an organic capping layer including (e.g., consisting of) an organic material, an inorganic capping layer including (e.g., consisting of) an inorganic material, or a composite capping layer including an organic material and an inorganic material.

The capping layer may include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and the amine-based compound may each independently be optionally substituted with a substituent containing at least one element selected from O, N, S, Se, Si, F, Cl, Br, and I. In one embodiment, the capping layer may include an amine-based compound.

In one or more embodiments, the capping layer may include a compound represented by Formula 201 or a compound represented by Formula 202.

In one or more embodiments, the capping layer may include a compound selected from Compounds HT28 to HT33 and Compounds CP1 to CP5 below, but embodiments of the present disclosure are not limited thereto:

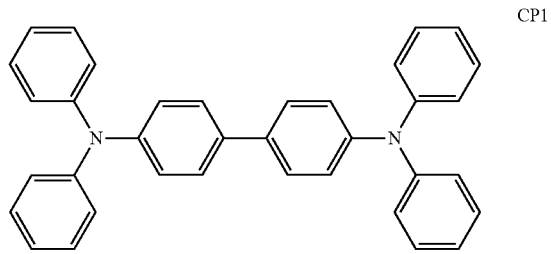

CP1

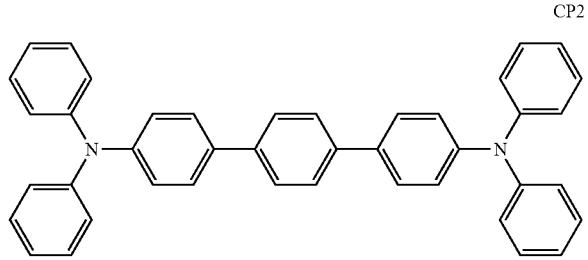

CP2

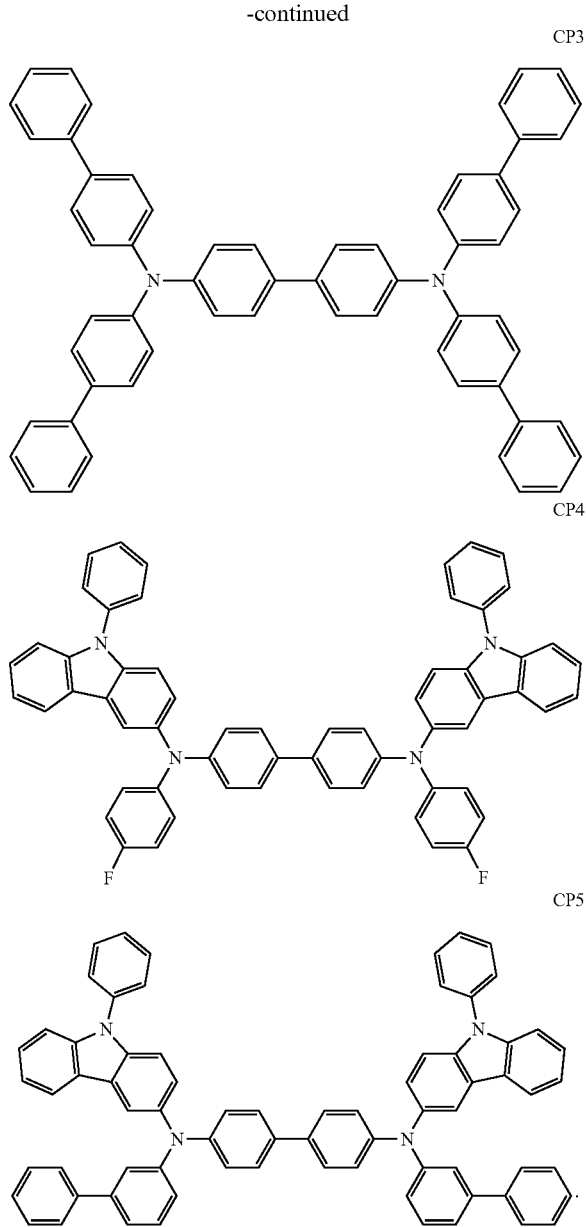

Hereinbefore, the organic light-emitting device has been described with reference to the drawing, but embodiments of the present disclosure are not limited thereto.

Layers constituting the hole transport region, the emission layer, and layers constituting the electron transport region may each independently be formed in a certain region by using one or more suitable methods selected from vacuum deposition, spin coating, casting, Langmuir-Blodgett (LB) deposition, ink-jet printing, laser-printing, and laser-induced thermal imaging.

When any of the layers constituting the hole transport region, the emission layer, and the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, by taking into account a material to be included in a layer to be formed, and the structure of a layer to be formed.

When any of the layers constituting the hole transport region, the emission layer, and the electron transport region are formed by spin coating, the spin coating may be performed at a coating speed of about 2,000 rpm to about 5,000 rpm and at a heat treatment temperature of about 80° C. to 200° C., by taking into account a material to be included in a layer to be formed, and the structure of a layer to be formed.

Apparatus

The organic light-emitting device may be included in various suitable apparatuses.

Another embodiment of the present disclosure provides an apparatus including the organic light-emitting device.

For example, the apparatus may be a light-emitting apparatus, an authentication apparatus, and/or an electronic apparatus, but embodiments of the present disclosure are not limited thereto.

The light-emitting apparatus may be used as various suitable displays, light sources, and/or the like.

The authentication apparatus may be, for example, a biometric authentication apparatus for authenticating an individual by using biometric information of a biometric body (for example, a finger tip, a pupil, and/or the like).

The authentication apparatus may further include, in addition to the organic light-emitting device, a biometric information collector.

The electronic apparatus may be applied to personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram (ECG) displays, ultrasonic diagnostic devices, and/or endoscope displays), fish finders, various measuring instruments, meters (for example, meters for a vehicle, an aircraft, and/or a vessel), projectors, and/or the like, but embodiments of the present disclosure are not limited thereto.

In one embodiment, the apparatus may further include, in addition to the organic light-emitting device, a thin-film transistor. Here, the thin-film transistor may include a source electrode, an activation layer, and a drain electrode, wherein the first electrode of the organic light-emitting device may be in electrical contact with one selected from the source electrode and the drain electrode of the thin-film transistor.

General Definition of Substituents

The term "$C_1$-$C_{60}$ alkyl group" as used herein refers to a linear or branched aliphatic saturated hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle and/or at either terminus of the $C_2$-$C_{60}$ alkyl group, and non-limiting examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle and/or at either terminus of the $C_2$-$C_{60}$ alkyl group, and non-limiting examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom and 1 to 10 carbon atoms as the remaining ring-forming atoms, and non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term $C_3$-$C_{10}$ cycloalkenyl group used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, as the remaining ring-forming atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. The term "$C_6$-$C_{60}$ arylene group" used herein refers to a divalent group having the same structure as the $C_6$-$C_{60}$ aryl group. When the $C_6$-$C_{60}$ aryl group and the $C_6$-$C_{60}$ arylene group each independently include two or more rings, the respective two or more rings may be fused to each other.

The term "$C_1$-$C_{60}$ heteroaryl group" as used herein refers to a monovalent group having a carbocyclic aromatic system that has at least one heteroatom selected from N, O, Si, P, and S as a ring-forming atom, in addition to 1 to 60 carbon atoms as the remaining ring-forming atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. The term "$C_1$-$C_{60}$ heteroarylene group" as used herein refers to a divalent group having the same structure as the $C_1$-$C_{60}$ heteroaryl group. When the $C_1$-$C_{60}$ heteroaryl group and the $C_1$-$C_{60}$ heteroarylene group each independently include two or more rings, the respective two or more rings may be condensed (e.g., fused) with each other.

The term "$C_6$-$C_{60}$ aryloxy group" as used herein refers to a monovalent group represented by —$OA_{102}$ (wherein A102 is the $C_6$-$C_{60}$ aryl group), and the term "$C_6$-$C_{60}$ arylthio group" as used herein refers to a monovalent group represented by —$SA_{103}$ (wherein A103 is the $C_6$-$C_{60}$ aryl group).

The term "monovalent non-aromatic condensed polycyclic group" as used herein refers to a monovalent group having two or more rings condensed with each other, only carbon atoms as ring-forming atoms (e.g., 8 to 60 carbon atoms), and no aromaticity in its entire molecular structure (e.g., the molecular structure as a whole is non-aromatic). A non-limiting example of the monovalent non-aromatic condensed polycyclic group is a 9,10-dihydroanthracenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, at least one heteroatom selected from N, O, Si, P, and S, other than carbon atoms (e.g., 1 to 60 carbon atoms), as a ring-forming atom, and no aromaticity in its entire molecular structure (e.g., the molecular structure as a whole is non-aromatic). A non-limiting example of the monovalent non-aromatic condensed heteropolycyclic group is a 9,9-dihydroacridinyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group that includes only carbon atoms as ring-forming atoms and includes 5 to 60 ring-forming carbon atoms. The $C_5$-$C_{60}$ carbocyclic group may be an aromatic carbocyclic group or a non-aromatic carbocyclic group. The $C_5$-$C_{60}$ carbocyclic group may be a ring (such as benzene), a monovalent group (such as a phenyl group), or a divalent group (such as a phenylene group). In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_5$-$C_{60}$ carbocyclic group, except that as one or more ring-forming atoms, at least one heteroatom selected from N, O, Si, P, and S is used in addition to carbon atoms (the number of carbon atoms may be in a range of 1 to 60).

In the present specification, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein refers to a phenyl group, the term "Me" as used herein refers to a methyl group, the term "Et" as used herein refers to an ethyl group, the term "ter-Bu" or "But" as used herein refers to a tert-butyl group, the term "OMe" as used herein refers to a methoxy group, and "D" refers to deuterium.

The term "biphenyl group" as used herein refers to "a phenyl group substituted with a phenyl group". For example, the "biphenyl group" may be a substituted phenyl group having a $C_6$-$C_{60}$ aryl group as a substituent.

The term "terphenyl group" as used herein refers to "a phenyl group substituted with a biphenyl group". For example, the "terphenyl group" may be a substituted phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a light-emitting device according to embodiments will be described in more detail with reference to Examples.

EXAMPLES

Evaluation Example 1: Measurement of HOMO Energy Level

HOMO energy levels of Compounds C101, C202, C302, C401, C501, X1 and X2 used in Examples 1 and 2 and Comparative Examples 1 to 6 were measured by using photoelectron spectrometer AC-2 (manufactured by Riken Keiki Co. Ltd.), and results thereof are shown in Table 1.

TABLE 1

| Compound | HOMO energy level (eV) |
|---|---|
| C101 | −5.1 eV |
| C202 | −5.3 eV |
| C302 | −5.4 eV |
| C401 | −5.5 eV |
| C501 | −5.6 eV |
| X1 | −5.9 eV |
| X2 | −7.2 eV |

185 186
C101
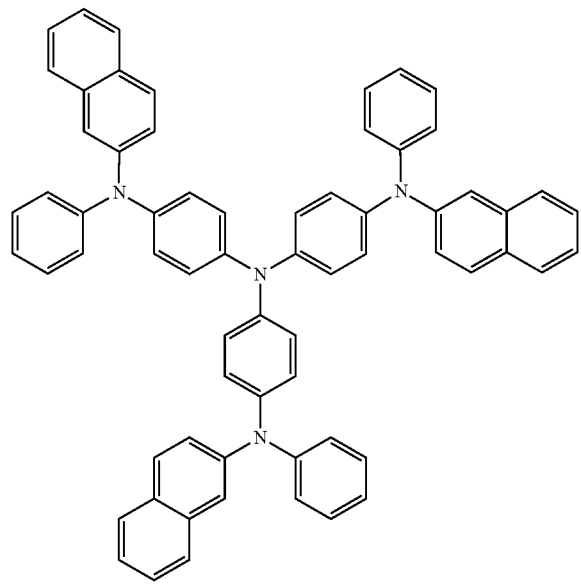
C202
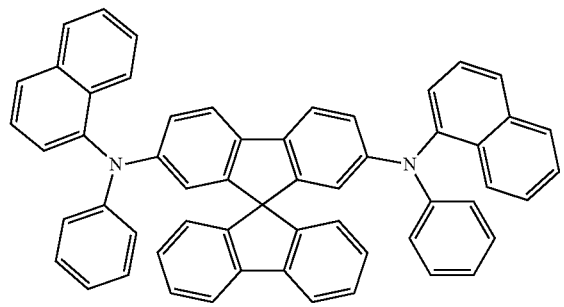
C302
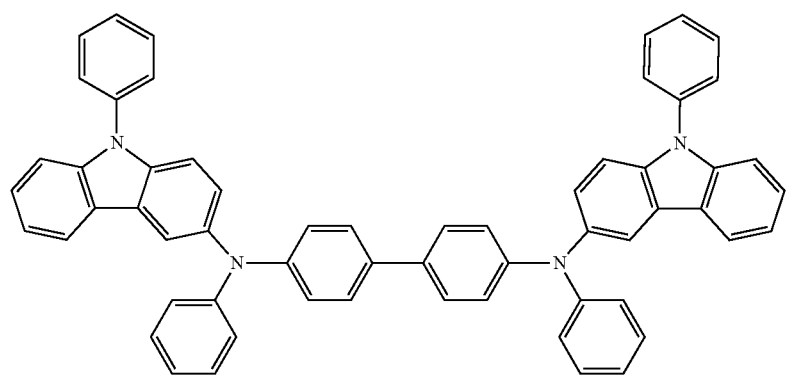
C401
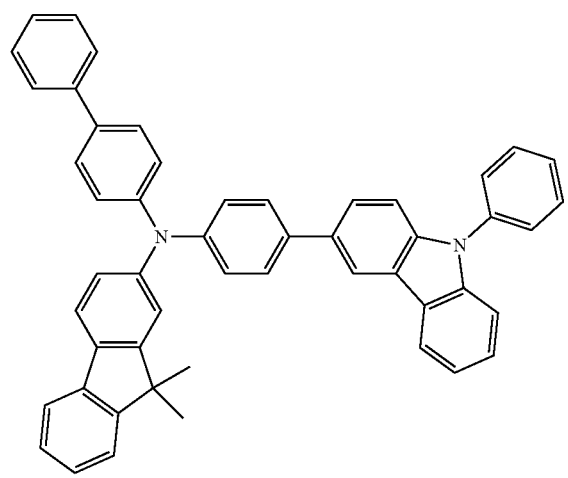
C501
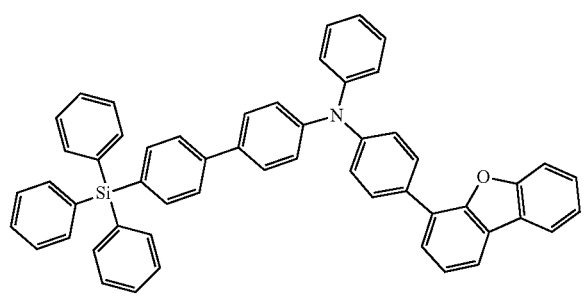

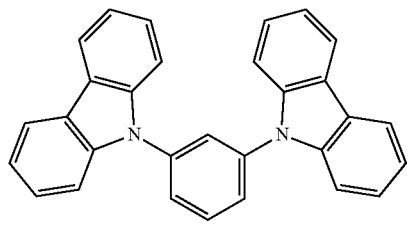

-continued

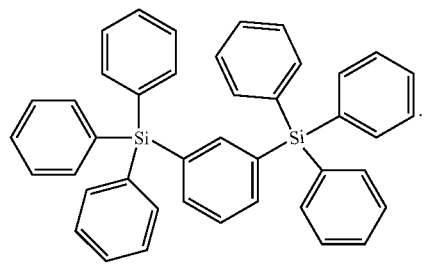

In Table 1, Compounds C101, C202, C302, C401 and C501 satisfy all of Equations 1 to 4 of the present disclosure, whereas Compounds X1, X2 (where X1 and X2 are comparative compounds) and C501 do not satisfy the energy relationship of Equations 1 to 4.

Example 1

A Corning 15 Ω/cm² (1,200 Å) ITO glass substrate (anode) was cut to a size of 50 mm×50 mm×0.5 mm, sonicated with isopropyl alcohol and pure water each for 15 minutes, and then cleaned by ultraviolet rays irradiation and exposure to ozone for 30 minutes. Then, the ITO glass substrate was provided to a vacuum deposition apparatus.

C202 and HATCN were co-deposited on the ITO glass substrate at the weight ratio of 90:10 to form a first hole injection layer having a thickness of 200 Å thickness, and then, C202 was vacuum-deposited on the first hole injection layer to form a first hole transport layer having a thickness of 400 Å, thereby completing the formation of a first hole transport stack.

C401 and HATCN were co-deposited on the first hole transport stack at the weight ratio of 90:10 to form a second hole injection layer having a thickness of 200 Å, and then, C401 was vacuum-deposited on the second hole injection layer to form a second hole transport layer having a thickness of 400 Å, thereby completing the formation of a second hole transport stack.

C501 was vacuum-deposited on the second hole transport stack to form an electron blocking layer having a thickness of 100 Å.

CBP (as a host) and 4CzIPN (as a dopant) were co-deposited on the electron blocking layer at the weight ratio of 80:20 to form an emission layer having a thickness of 300 Å.

TPBi was vacuum-deposited on the emission layer to form a hole blocking layer having a thickness of 100 Å.

Alq3 was vacuum-deposited on the hole blocking layer to form an electron transport layer having a thickness of 300 Å. Liq was vacuum-deposited on the electron transport layer to form an electron injection layer having a thickness of 10 Å, and Al was vacuum-deposited on the electron injection layer to form a cathode having a thickness of 2000 Å, thereby completing the manufacture of an organic light-emitting device.

Example 2

An organic light-emitting device was manufactured in substantially the same manner as in Example 1 except that, in forming the first hole injection layer, C101 was used instead of C202 and HATCN, and in forming the second hole injection layer, C302 was used instead of C401 and HATCN.

Comparative Example 1

An organic light-emitting device was manufactured in substantially the same manner as in Example 1, except that the second hole transport stack was not formed on the first hole transport stack.

Comparative Example 2

An organic light-emitting device was manufactured in substantially the same manner as in Example 2, except that the second hole transport stack was not formed on the first hole transport stack.

Comparative Example 3

An organic light-emitting device was manufactured in substantially the same manner as in Example 1, except that the second hole injection layer of the second hole transport stack was not formed.

Comparative Example 4

An organic light-emitting device was manufactured in substantially the same manner as in Example 1, except that the second hole transport layer of the second hole transport stack was not formed.

Comparative Example 5

An organic light-emitting device was manufactured in substantially the same manner as in Example 1, except that, in forming the first hole injection layer and the first hole transport layer, Compound X1 was used instead of C202, and in forming the second hole injection layer and the second hole transport layer, Compound X2 was used instead of C401.

Comparative Example 6

An organic light-emitting device was manufactured in substantially the same manner as in Example 1, except that the hole transport region was formed to have the stack structure of m-MTDATA (35 nm)/1% F4-TCNQ-doped NPB (50 nm)/HAT-CN (20 nm)/NPB (20 nm) from the anode.

Evaluation Example 2

The efficiency (cd/A) at a current density of 10 mA/cm² and the lifespan (LT90) of the organic light-emitting devices manufactured according to Examples 1 and 2 and Comparative Examples 1 to 6 were measured. The results thereof are shown in Table 2. The driving voltage and current density of the organic light-emitting devices were measured using a source meter (manufactured by Keithley Instrument Inc., 2400 series).

The current efficiency and lifespan shown in Table 2 were represented as a relative value (%) relative to when the current efficiency and lifespan of the organic light-emitting device manufactured according to Comparative Example 1 was 100%.

TABLE 2

|  | Current efficiency (Relative value, %) | Lifespan (Relative value, %) |
|---|---|---|
| Example 1 | 105% | 165% |
| Example 2 | 102% | 150% |
| Comparative Example 1 | 100% | 100% |
| Comparative Example 2 | 101% | 98% |
| Comparative Example 3 | 98% | 102% |
| Comparative Example 4 | 94% | 92% |
| Comparative Example 5 | 54% | 61% |
| Comparative Example 6 | 84% | 89% |

From Table 2, it can be seen that the organic light-emitting devices of Examples 1 and 2 had higher efficiency and longer lifespan than the organic light-emitting devices of Comparative Examples 1 to 6.

The organic light-emitting devices according to embodiments of the present disclosure have high efficiency and a long lifespan.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the drawing, it will be understood by those of ordinary skill in the art that various changes in form and details may be made therein without departing from the spirit and scope of the present disclosure as defined by the following claims and their equivalents.

What is claimed is:

1. An organic light-emitting device comprising:

a first electrode;

a second electrode facing the first electrode; and an organic layer between the first electrode and the second electrode, the organic layer comprising an emission layer and a hole transport region between the first electrode and the emission layer, wherein the hole transport region comprises a first hole transport stack, a second hole transport stack between the first hole transport stack and the emission layer, and an electron blocking layer between the second hole transport stack and the emission layer, the first hole transport stack comprises a first hole injection layer and a first hole transport layer, the second hole transport stack comprises a second hole injection layer and a second hole transport layer, the first hole injection layer is between the first electrode and the first hole transport layer, the second hole injection layer is between the first hole transport layer and the second hole transport layer, the first hole injection layer comprises a first compound, the first hole transport layer comprises a second compound, the second hole injection layer comprises a third compound, the second hole transport layer comprises a fourth compound, the electron blocking layer comprises a fifth compound, the first compound, the second compound, the third compound, the fourth compound, and the fifth compound all are different from one another, and the organic light-emitting device satisfies Equations 1 to 4:

$$HOMO(HTM1) \geq HOMO(HTM2) \quad \text{Equation 1}$$

$$HOMO(HTM3) \geq HOMO(HTM4) \quad \text{Equation 2}$$

$$HOMO(HTM1) - HOMO(HTM2) \leq 0.5 \text{ eV} \quad \text{Equation 3}$$

$$HOMO(HTM3) - HOMO(HTM4) \leq 0.5 \text{ eV}, \quad \text{Equation 4}$$

wherein in Equations 1 to 4, the HOMO(HTM1) is a lower energy level from among the HOMO energy level (eV) of the first compound and the HOMO energy level (eV) of the second compound, the HOMO(HTM2) is a higher energy level from among the HOMO energy level (eV) of the third compound and the HOMO energy level (eV) of the fourth compound, the HOMO(HTM3) is a lower energy level from among the HOMO energy level (eV) of the third compound and the HOMO energy level (eV) of the fourth compound, and the HOMO(HTM4) is the HOMO energy level (eV) of the fifth compound, wherein the fifth compound is a compound represented by Formula 5:

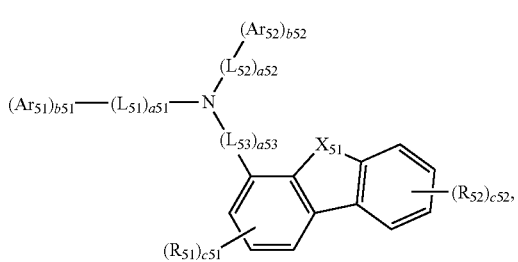

Formula 5 wherein, in Formula 5, $X_{51}$ is O or S, $L_{51}$ to $L_{53}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a51 to a53 are each independently an integer from 0 to 3, and $Ar_{51}$ and $Ar_{52}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), where $Q_1$ to $Q_3$ are each an unsubstituted phenyl group, and wherein at least one selected from among $Ar_{51}$ and $Ar_{52}$ is —Si($Q_1$) ($Q_2$) ($Q_3$), b51 and b52 are each independently an integer from 1 to 5, $R_{51}$ and $R_{52}$ are each independently selected from hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, c51 is an integer from 1 to 3, and c52 is an integer from 1 to 4.

2. The organic light-emitting device of claim 1, wherein the first hole transport layer is at an interface between the first hole injection layer and the second hole injection layer.

3. The organic light-emitting device of claim 1, wherein the second hole injection layer is at an interface between the first hole transport layer and the second hole transport layer.

4. The organic light-emitting device of claim 1, wherein the electron blocking layer is at an interface between the second hole transport layer and the emission layer.

5. The organic light-emitting device of claim 1, wherein
the first hole injection layer consists of the first compound, and
the second hole injection layer consists of the third compound.

6. The organic light-emitting device of claim 1, wherein
HOMO(C1) is greater than or equal to HOMO(C2), and
HOMO(C3) is greater than or equal to HOMO(C4), and
wherein HOMO(C1), HOMO(C2), HOMO(C3), and HOMO(C4) indicate the HOMO energy levels (eV) of the first compound, the second compound, the third compound, and the fourth compound, respectively.

7. The organic light-emitting device of claim 1, wherein the first hole injection layer and the second hole injection layer each further comprise a p-dopant.

8. The organic light-emitting device of claim 7, wherein the p-dopant is a charge-generating material having a lowest unoccupied molecular orbital (LUMO) energy level of less than −3.5 eV.

9. The organic light-emitting device of claim 1, wherein a thickness of the first hole injection layer and a thickness of the second hole injection layer are each independently in a range from about 10 Å to about 500 Å.

10. The organic light-emitting device of claim 1, wherein a thickness of the first hole transport layer and a thickness of the second hole transport layer are each independently in a range from about 100 Å to about 1500 Å.

11. The organic light-emitting device of claim 1, wherein the first compound and the third compound are each independently selected from compounds represented by Formulae 1-1 to 1-4 and Formula 2:

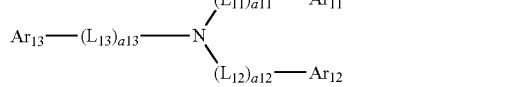

Formula 1-1

Formula 1-2

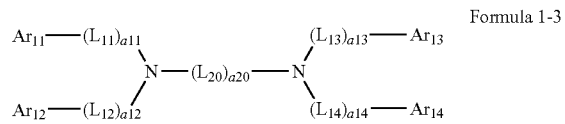

Formula 1-3

-continued

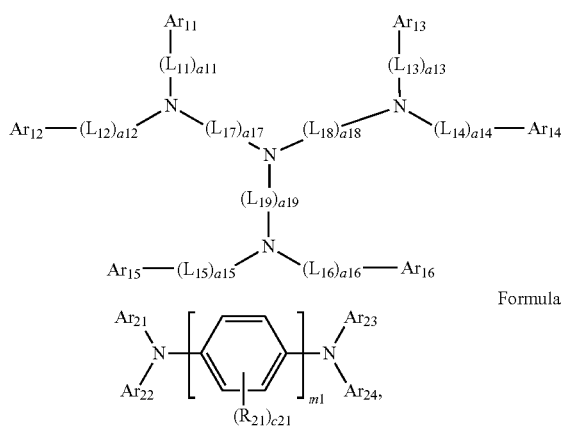
Formula 1-4

Formula 2 wherein, in Formulae 1-1 to 1-4, $A_1$ is a $C_5$-$C_{60}$ carbocyclic group or a $C_1$-$C_{60}$ heterocyclic group, each independently unsubstituted or substituted with at least one $R_1$, $L_1$ and $L_{11}$ to $L_{19}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{20}$ is selected from *—O—*', *—S—*', *—N($Q_{201}$)—*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 and a11 to a19 are each independently an integer from 0 to 3, a20 is an integer from 1 to 10, $Ar_1$, $Ar_{11}$ to $Ar_{16}$ and $Q_{201}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 is an integer from 1 to 5, n1 is an integer from 0 to 5, and in Formula 2, m1 is an integer from 1 to 5, $Ar_{21}$ to $Ar_{24}$ are each independently selected from a group represented by Formula 2A, a group represented by Formula 2B, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one of $Ar_{21}$ to $Ar_{24}$ is selected from groups represented by Formulae 2A and 2B,

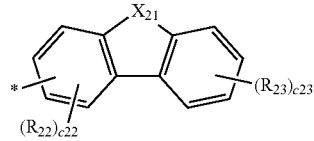
Formula 2A

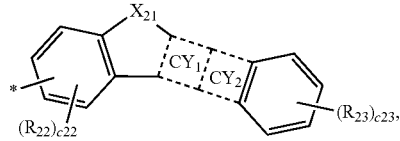
Formula 2B wherein, in Formulae 2A and 2B, $X_{21}$ is selected from $C(R_{24})(R_{25})$, $Si(R_{24})(R_{25})$, $N(R_{24})$, O, and S, $CY_1$ ring is a condensed benzene ring that is substituted with at least one $R_a$, $CY_1$ ring is condensed with a neighboring $X_{21}$-containing 5-membered ring and a neighboring $CY_2$ ring, $CY_2$ ring is a 5-membered ring represented by

$X_{22}$ is selected from $C(R_{26})(R_{27})$, $Si(R_{26})(R_{27})$, $N(R_{26})$, O, and S, wherein, in Formulae 1-1 to 1-4, 2, 2A, and 2B, $R_1$, $R_a$, and $R_{21}$ to $R_{27}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, c21 and c23 are each independently an integer from 1 to 4, c22 is an integer from 1 to 3, and $Q_1$ to $Q_3$ are each independently selected from hydrogen, deuterium, $-F$, $-Cl$, $-Br$, $-I$, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

12. The organic light-emitting device of claim 1, wherein the second compound and the fourth compound are each independently selected from compounds represented by Formulae 1-1 to 1-3:

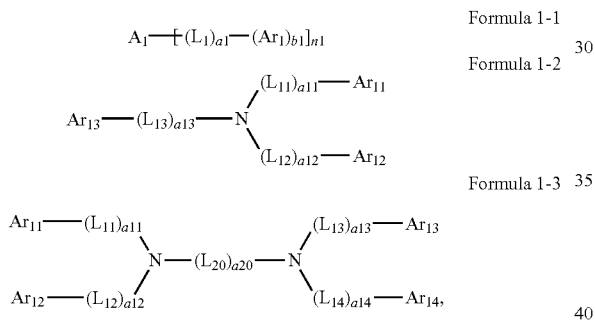

wherein, in Formulae 1-1 to 1-3, $A_1$ is a $C_5$-$C_{60}$ carbocyclic group or a $C_1$-$C_{60}$ heterocyclic group, each independently unsubstituted or substituted with at least one $R_1$, $R_1$ is selected from hydrogen, deuterium, $-F$, $-Cl$, $-Br$, $-I$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $L_1$ and $L_{11}$ to $L_{19}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{20}$ is selected from *—O—*', *—S—,*', *—N($Q_{201}$)—*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 and a11 to a14 are each independently an integer from 0 to 3, a20 is an integer from 1 to 10, $Ar_1$, $Ar_{11}$ to $Ar_{14}$ and $Q_{201}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 is an integer from 1 to 5, and n1 is an integer from 0 to 5.

13. The organic light-emitting device of claim 1, wherein the organic layer further comprises an electron transport region between the emission layer and the second electrode, and the electron transport region comprises at least one selected from an electron injection layer, an electron transport layer, a hole blocking layer, and a buffer layer.

14. The organic light-emitting device of claim 13, wherein the electron transport region comprises the hole blocking layer.

15. The organic light-emitting device of claim 13, wherein the electron transport region comprises the electron transport layer and the hole blocking layer, and the hole blocking layer is at an interface between the emission layer and the electron transport layer.

16. The organic light-emitting device of claim 1, wherein the emission layer comprises a host and a dopant, and an amount of the host in the emission layer is greater than an amount of the dopant in the emission layer.

17. The organic light-emitting device of claim 16, wherein the dopant comprises at least one selected from a fluorescent dopant, a phosphorescent dopant, and a delayed fluorescent dopant.

18. An apparatus comprising:
a thin-film transistor comprising a source electrode, a drain electrode, and an activation layer, and
the organic light-emitting device of claim 1, wherein the first electrode of the organic light-emitting device is electrically coupled with one selected from the source electrode and the drain electrode of the thin-film transistor.

* * * * *